United States Patent
Lazarev et al.

(10) Patent No.: US 10,707,019 B2
(45) Date of Patent: Jul. 7, 2020

(54) ELECTRO-POLARIZABLE COMPOUND AND CAPACITOR

(71) Applicant: CAPACITOR SCIENCES INCORPORATED, Menlo Park, CA (US)

(72) Inventors: Pavel Ivan Lazarev, Menlo Park, CA (US); Paul T. Furuta, Menlo Park, CA (US); Barry K. Sharp, Menlo Park, CA (US); Yan Li, Menlo Park, CA (US)

(73) Assignee: CAPACITOR SCIENCE INCORPORATED, Menlo Park, CA (US)

( * ) Notice: Subject to any disclaimer, the term of this patent is extended or adjusted under 35 U.S.C. 154(b) by 0 days.

(21) Appl. No.: 15/982,482

(22) Filed: May 17, 2018

(65) Prior Publication Data

US 2019/0139705 A1    May 9, 2019

Related U.S. Application Data

(62) Division of application No. 15/090,509, filed on Apr. 4, 2016, now Pat. No. 9,978,517.

(51) Int. Cl.
| | |
|---|---|
| *H01G 4/14* | (2006.01) |
| *C07D 471/22* | (2006.01) |
| *C07B 47/00* | (2006.01) |
| *H01G 4/18* | (2006.01) |
| *H01G 4/32* | (2006.01) |
| *C09B 5/62* | (2006.01) |
| *C09K 19/60* | (2006.01) |
| *C09B 5/00* | (2006.01) |
| *C09B 69/00* | (2006.01) |
| *C09B 57/08* | (2006.01) |
| *C09B 47/00* | (2006.01) |
| *C09B 47/04* | (2006.01) |

(52) U.S. Cl.
CPC ............. *H01G 4/14* (2013.01); *C07D 471/22* (2013.01); *C09B 5/008* (2013.01); *C09B 5/62* (2013.01); *C09B 47/00* (2013.01); *C09B 47/04* (2013.01); *C09B 57/08* (2013.01); *C09B 69/00* (2013.01); *C09K 19/606* (2013.01); *H01G 4/18* (2013.01); *H01G 4/32* (2013.01); *Y02T 10/7022* (2013.01)

(58) Field of Classification Search
CPC ... H01G 4/14; H01G 4/18; H01G 4/32; C07D 471/22; C09B 5/008; C09B 5/62; C09B 47/00; C09B 47/04; C09B 19/606
See application file for complete search history.

(56) References Cited

U.S. PATENT DOCUMENTS

| | | | |
|---|---|---|---|
| 3,407,394 | A | 10/1968 | Hartke |
| 4,549,034 | A | 10/1985 | Sato et al. |
| 4,694,377 | A | 9/1987 | MacDougall et al. |
| 4,702,562 | A | 10/1987 | Scheuble et al. |
| 4,894,186 | A | 1/1990 | Gordon et al. |
| 5,141,837 | A | 8/1992 | Nguyen et al. |
| 5,187,639 | A | 2/1993 | Ogawa et al. |
| 5,248,774 | A | 9/1993 | Dietz et al. |
| 5,312,896 | A | 5/1994 | Bhardwaj et al. |
| 5,384,521 | A | 1/1995 | Coe |
| 5,395,556 | A | 3/1995 | Drost et al. |

(Continued)

FOREIGN PATENT DOCUMENTS

| | | |
|---|---|---|
| CA | 2074848 A1 | 2/1998 |
| CN | 1582506 A | 2/2005 |

(Continued)

OTHER PUBLICATIONS

Notice of Allowance for U.S. Appl. No. 14/931,757, dated Oct. 31, 2017.

(Continued)

*Primary Examiner* — Timothy R Rozof
(74) *Attorney, Agent, or Firm* — BCF LLP

(57) ABSTRACT

An electro-polarizable compound has the following general formula:

(I)

where Core1 is an aromatic polycyclic conjugated molecule having two-dimensional flat form and self-assembling by pi-pi stacking in a column-like supramolecule, which is tetrapirolic macro-cyclic fragment, R1 is an dopant group connected to Core1, m is number of R1 which is equal to 1, 2, 3 or 4, R2 is a substituent comprising one or more ionic groups, p is number of R2 which is equal to 0, 1, 2, 3 or 4. The fragment marked NLE containing the Core1 with at least one R1 has a nonlinear effect of polarization. Core2 is an electro-conductive oligomer self-assembling by pi-pi stacking in a column-like supramolecule, n is number of Core2 which is equal to 2, or 4, R3 is a substituent comprising one or more ionic groups, s is number of R3 which is equal to 0, 1, 2, 3 or 4. R4 is a non-polar resistive substituent, k is a number of R4 which is equal to 0, 1, 2, 3, 4, 5, 6, 7 or 8.

19 Claims, 1 Drawing Sheet

(56) References Cited

U.S. PATENT DOCUMENTS

| | | |
|---|---|---|
| 5,466,807 A | 11/1995 | Dietz et al. |
| 5,514,799 A | 5/1996 | Varanasi et al. |
| 5,581,437 A | 12/1996 | Sebillotte et al. |
| 5,583,359 A | 12/1996 | Ng et al. |
| 5,597,661 A | 1/1997 | Takeuchi et al. |
| 5,679,763 A | 10/1997 | Jen et al. |
| 5,742,471 A | 4/1998 | Barbee et al. |
| 5,840,906 A | 11/1998 | Zoltewicz et al. |
| 5,880,951 A | 3/1999 | Inaba |
| 6,025,094 A | 2/2000 | Visco et al. |
| 6,282,081 B1 | 8/2001 | Takabayashi et al. |
| 6,294,593 B1 | 9/2001 | Jeng et al. |
| 6,341,056 B1 | 1/2002 | Allman et al. |
| 6,391,104 B1 | 5/2002 | Schulz |
| 6,426,861 B1 | 7/2002 | Munshi |
| 6,501,093 B1 | 12/2002 | Marks |
| 6,519,136 B1 | 2/2003 | Chu et al. |
| 6,617,830 B2 | 9/2003 | Nozu et al. |
| 6,798,642 B2 | 9/2004 | Decker et al. |
| 7,025,900 B2 | 4/2006 | Sidorenko et al. |
| 7,033,406 B2 | 4/2006 | Weir et al. |
| 7,211,824 B2 | 5/2007 | Lazarev |
| 7,342,755 B1 | 3/2008 | Horvat et al. |
| 7,460,352 B2 | 12/2008 | Jamison et al. |
| 7,466,536 B1 | 12/2008 | Weir et al. |
| 7,498,689 B2 | 3/2009 | Mitani et al. |
| 7,579,709 B2 | 8/2009 | Goetz et al. |
| 7,625,497 B2 | 12/2009 | Iverson et al. |
| 7,678,907 B2 | 3/2010 | Koenemann et al. |
| 7,750,505 B2 | 7/2010 | Ichikawa |
| 7,795,431 B2 | 9/2010 | Pschirer et al. |
| 7,808,771 B2 | 10/2010 | Nguyen et al. |
| 7,837,902 B2 | 11/2010 | Hsu et al. |
| 7,893,265 B2 | 2/2011 | Facchetti et al. |
| 7,910,736 B2 | 3/2011 | Koenemann et al. |
| 7,947,199 B2 | 5/2011 | Wessling |
| 7,990,679 B2 | 8/2011 | Ehrenberg et al. |
| 8,143,853 B2 | 3/2012 | Jestin et al. |
| 8,222,074 B2 | 7/2012 | Lazarev |
| 8,231,809 B2 | 7/2012 | Pschirer et al. |
| 8,236,998 B2 | 8/2012 | Nagata et al. |
| 8,344,142 B2 | 1/2013 | Marder et al. |
| 8,372,527 B2 | 2/2013 | Morishita et al. |
| 8,404,844 B2 | 3/2013 | Kastler et al. |
| 8,527,126 B2 | 9/2013 | Yamamoto et al. |
| 8,552,179 B2 | 10/2013 | Lazarev |
| 8,766,566 B2 | 7/2014 | Baba et al. |
| 8,818,601 B1 | 8/2014 | V et al. |
| 8,831,805 B2 | 9/2014 | Izumi et al. |
| 8,895,118 B2 | 11/2014 | Geivandov et al. |
| 8,929,054 B2 | 1/2015 | Felten et al. |
| 8,938,160 B2 | 1/2015 | Wang |
| 9,056,676 B1 | 6/2015 | Wang |
| 9,293,260 B2 | 3/2016 | Schmid et al. |
| 9,589,727 B2 | 3/2017 | Lazarev |
| 9,899,150 B2 | 2/2018 | Lazarev et al. |
| 9,916,931 B2 | 3/2018 | Lazarev |
| 9,978,517 B2 | 5/2018 | Lazarev et al. |
| 10,153,087 B2 | 12/2018 | Lazarev et al. |
| 2002/0027220 A1 | 3/2002 | Wang et al. |
| 2002/0048140 A1 | 4/2002 | Gallay et al. |
| 2003/0026063 A1 | 2/2003 | Munshi |
| 2003/0102502 A1 | 6/2003 | Togashi |
| 2003/0103319 A1 | 6/2003 | Kumar et al. |
| 2003/0105365 A1 | 6/2003 | Smith et al. |
| 2003/0142461 A1 | 7/2003 | Decker et al. |
| 2003/0160595 A1 | 8/2003 | Provanzana et al. |
| 2003/0219647 A1 | 11/2003 | Wariishi |
| 2004/0173873 A1 | 9/2004 | Kumar et al. |
| 2004/0222413 A1 | 11/2004 | Hsu et al. |
| 2004/0223291 A1 | 11/2004 | Naito et al. |
| 2005/0118083 A1 | 6/2005 | Tabuchi |
| 2006/0120014 A1 | 6/2006 | Nakamura et al. |
| 2006/0120020 A1 | 6/2006 | Dowgiallo |
| 2007/0001258 A1 | 1/2007 | Aihara |
| 2007/0003781 A1 | 1/2007 | Rochemont |
| 2007/0108940 A1 | 5/2007 | Sainomoto et al. |
| 2007/0159767 A1 | 7/2007 | Jamison et al. |
| 2007/0181973 A1 | 8/2007 | Hung et al. |
| 2008/0002329 A1 | 1/2008 | Pohm et al. |
| 2008/0150484 A1 | 6/2008 | Kimball et al. |
| 2008/0266750 A1 | 10/2008 | Wu et al. |
| 2008/0283283 A1 | 11/2008 | Abe et al. |
| 2009/0040685 A1 | 2/2009 | Hiemer et al. |
| 2009/0184355 A1 | 7/2009 | Brederlow et al. |
| 2010/0011656 A1 | 1/2010 | Gessner et al. |
| 2010/0038629 A1 | 2/2010 | Lazarev |
| 2010/0085521 A1 | 4/2010 | Kasianova et al. |
| 2010/0172066 A1 | 7/2010 | Baer et al. |
| 2010/0178728 A1 | 7/2010 | Zheng et al. |
| 2010/0183919 A1 | 7/2010 | Holme et al. |
| 2010/0193777 A1 | 8/2010 | Takahashi et al. |
| 2010/0214719 A1 | 8/2010 | Kim et al. |
| 2010/0233491 A1 | 9/2010 | Nokel et al. |
| 2010/0255381 A1 | 10/2010 | Holme et al. |
| 2010/0269731 A1 | 10/2010 | Jespersen et al. |
| 2010/0309606 A1 | 12/2010 | Allers et al. |
| 2010/0309696 A1 | 12/2010 | Guillot et al. |
| 2010/0315043 A1 | 12/2010 | Chau |
| 2011/0006393 A1 | 1/2011 | Cui |
| 2011/0042649 A1 | 2/2011 | Duvall et al. |
| 2011/0079733 A1 | 4/2011 | Langhals et al. |
| 2011/0079773 A1 | 4/2011 | Wasielewski et al. |
| 2011/0110015 A1 | 5/2011 | Zhang et al. |
| 2011/0149393 A1 | 6/2011 | Nokel et al. |
| 2011/0228442 A1 | 9/2011 | Zhang et al. |
| 2012/0008251 A1 | 1/2012 | Yu et al. |
| 2012/0033342 A1 | 2/2012 | Ito et al. |
| 2012/0053288 A1 | 3/2012 | Morishita et al. |
| 2012/0056600 A1 | 3/2012 | Nevin |
| 2012/0059307 A1 | 3/2012 | Harris et al. |
| 2012/0113380 A1 | 5/2012 | Geivandov et al. |
| 2012/0122274 A1 | 5/2012 | Lazarev |
| 2012/0244330 A1 | 9/2012 | Sun et al. |
| 2012/0268862 A1 | 10/2012 | Song et al. |
| 2012/0274145 A1 | 11/2012 | Taddeo |
| 2012/0302489 A1 | 11/2012 | Rodrigues et al. |
| 2013/0056720 A1 | 3/2013 | Kim et al. |
| 2013/0187475 A1 | 7/2013 | Vendik et al. |
| 2013/0194716 A1 | 8/2013 | Holme et al. |
| 2013/0215535 A1 | 8/2013 | Bellomo |
| 2013/0224473 A1 | 8/2013 | Tassell et al. |
| 2013/0314839 A1 | 11/2013 | Terashima et al. |
| 2013/0342967 A1 | 12/2013 | Lai et al. |
| 2014/0035100 A1 | 2/2014 | Cho |
| 2014/0036410 A1 | 2/2014 | Okamatsu et al. |
| 2014/0098458 A1 | 4/2014 | Almadhoun et al. |
| 2014/0158340 A1 | 6/2014 | Dixler et al. |
| 2014/0169104 A1 | 6/2014 | Kan et al. |
| 2014/0185260 A1 | 7/2014 | Chen et al. |
| 2014/0268490 A1 | 9/2014 | Tsai et al. |
| 2014/0316387 A1 | 10/2014 | Harris et al. |
| 2014/0347787 A1 | 11/2014 | Fathi et al. |
| 2015/0008671 A1 | 1/2015 | Rentero et al. |
| 2015/0008735 A1 | 1/2015 | Mizoguchi |
| 2015/0158392 A1 | 6/2015 | Zhao |
| 2015/0162131 A1 | 6/2015 | Felten et al. |
| 2015/0235769 A1 | 8/2015 | Carver et al. |
| 2015/0249401 A1 | 9/2015 | Eriksen et al. |
| 2015/0302990 A1 | 10/2015 | Ghosh et al. |
| 2016/0001662 A1 | 1/2016 | Miller et al. |
| 2016/0020026 A1 | 1/2016 | Lazarev |
| 2016/0020027 A1 | 1/2016 | Lazarev |
| 2016/0254092 A1 | 9/2016 | Lazarev et al. |
| 2016/0314901 A1 | 10/2016 | Lazarev |
| 2016/0340368 A1 | 11/2016 | Lazarev |
| 2016/0379757 A1 | 12/2016 | Robinson et al. |
| 2017/0117097 A1 | 4/2017 | Furuta et al. |
| 2017/0133167 A1 | 5/2017 | Keller et al. |
| 2017/0232853 A1 | 8/2017 | Lazarev et al. |
| 2017/0233528 A1 | 8/2017 | Sharp et al. |
| 2017/0236641 A1 | 8/2017 | Furuta et al. |
| 2017/0236642 A1 | 8/2017 | Furuta et al. |
| 2017/0236648 A1 | 8/2017 | Lazarev et al. |

(56) References Cited

U.S. PATENT DOCUMENTS

| | | |
|---|---|---|
| 2017/0237271 A1 | 8/2017 | Kelly-Morgan et al. |
| 2017/0237274 A1 | 8/2017 | Lazarev et al. |
| 2017/0287637 A1 | 10/2017 | Lazarev et al. |
| 2017/0287638 A1 | 10/2017 | Lazarev et al. |
| 2017/0301467 A1 | 10/2017 | Lazarev et al. |
| 2018/0033554 A1 | 2/2018 | Li et al. |
| 2018/0061582 A1 | 3/2018 | Furuta et al. |
| 2018/0122143 A1 | 5/2018 | Ellwood |
| 2018/0126857 A1 | 5/2018 | Kelly-Morgan |
| 2018/0137978 A1 | 5/2018 | Hein et al. |
| 2018/0137984 A1 | 5/2018 | Furuta et al. |
| 2018/0158616 A1 | 6/2018 | Lazarev et al. |

FOREIGN PATENT DOCUMENTS

| | | | |
|---|---|---|---|
| CN | 100449661 | | 1/2009 |
| CN | 1748271 | B | 6/2010 |
| CN | 102426918 | A | 4/2012 |
| CN | 103261370 | A | 8/2013 |
| CN | 203118781 | U | 8/2013 |
| CN | 203377785 | U | 1/2014 |
| CN | 103755703 | A | 4/2014 |
| CN | 103986224 | A | 8/2014 |
| CN | 103258656 | B | 8/2015 |
| DE | 1130099 | * | 5/1962 |
| DE | 10203918 | A1 | 8/2003 |
| DE | 102010012949 | A1 | 9/2011 |
| DE | 102011101304 | A1 | 11/2012 |
| DE | 102012016438 | A1 | 2/2014 |
| EP | 0493716 | A1 | 7/1992 |
| EP | 0585999 | A1 | 3/1994 |
| EP | 0602654 | A1 | 6/1994 |
| EP | 0729056 | A1 | 8/1996 |
| EP | 0791849 | A1 | 8/1997 |
| EP | 0986080 | A3 | 1/2004 |
| EP | 0865142 | B1 | 5/2008 |
| EP | 2062944 | A1 | 5/2009 |
| EP | 2108673 | A1 | 10/2009 |
| EP | 2415543 | A1 | 2/2012 |
| EP | 1486590 | B1 | 12/2013 |
| EP | 2759480 | A1 | 7/2014 |
| EP | 1990682 | B1 | 1/2015 |
| GB | 547853 | A | 9/1942 |
| GB | 923148 | A | 4/1963 |
| GB | 2084585 | B | 11/1983 |
| JP | S6386731 | A | 4/1988 |
| JP | H03253014 | A | 11/1991 |
| JP | 2786298 | B2 | 8/1998 |
| JP | 2000100484 | A | 4/2000 |
| JP | 2001093778 | A | 4/2001 |
| JP | 2007287829 | A | 11/2007 |
| JP | 2010106225 | A | 5/2010 |
| JP | 2010160989 | A | 7/2010 |
| JP | 2011029442 | A | 2/2011 |
| JP | 2014139296 | A | 7/2014 |
| RU | 2199450 | C1 | 2/2003 |
| RU | 2512880 | C2 | 4/2014 |
| WO | 1990009616 | A1 | 8/1990 |
| WO | 0139305 | A1 | 5/2001 |
| WO | 2002026774 | A2 | 4/2002 |
| WO | 2007078916 | A2 | 7/2007 |
| WO | 2008038047 | A2 | 4/2008 |
| WO | 2009144205 | A1 | 12/2009 |
| WO | 2009158553 | A2 | 12/2009 |
| WO | 2011056903 | A1 | 5/2011 |
| WO | 2011137137 | A1 | 11/2011 |
| WO | 2012012672 | A2 | 1/2012 |
| WO | 2012084536 | A1 | 6/2012 |
| WO | 2012122312 | A1 | 9/2012 |
| WO | 2012142460 | A1 | 10/2012 |
| WO | 2012162500 | A2 | 11/2012 |
| WO | 2013009772 | A1 | 1/2013 |
| WO | 2013085467 | A1 | 6/2013 |
| WO | 2014009686 | A1 | 1/2014 |
| WO | 2015003725 | A1 | 1/2015 |
| WO | 2015175522 | A1 | 11/2015 |
| WO | 2015175558 | A2 | 11/2015 |

OTHER PUBLICATIONS

Notice of Allowance for U.S. Appl. No. 15/053,943, dated Aug. 14, 2017.

Notice of Allowance for U.S. Appl. No. 15/090,509, dated Jan. 24, 2018.

Notice of Allowance for U.S. Appl. No. 14/710,491, dated Oct. 24, 2016.

Office Action dated Dec. 13, 2017 for Taiwan Patent Application No. 106104499.

Office Action dated Dec. 13, 2017 for Taiwan Patent Application No. 106104500.

Office Action dated Jan. 25, 2018 for Chinese patent application No. 20158005146.4.

Office Action dated Oct. 19, 2017 for Taiwan patent Application No. 106104501.

Optical Society of America, Kuzyk et al, "Theory of Molecular Nonlinear Optics", pp. 5, 4-82, Department of Physics and Astronomy, Washington State University, Pullman, Washington 99164-2814, USA, Mar. 26, 2013.

Philosophical Transactions of the Royal Society, Simon, "Charge storage mechanism in nanoporous carbons and its consequence for electrical double layer capacitors" pp. 3457-3467; Drexel University, Philadelphia, PA 19104, 2010.

Pubchem Open Chemistry Database, Compound Summary for CID 91001799. Mar. 17, 2015. pp. 1-10.

R. J. Baker and B. P. Johnson, "stacking power MOSFETs for use in high speed instrumentation", Department of Electrical Engineering, University of Nevada, Reno, Reno. Nevada 89557-0030; pp. 5799-5801 Aug. 3, 1992.

Roger D. Hartman and Herbert A. Pohl, "Hyper-electronic Polarization in Macromolecular Solids", Journal of Polymer Science: Part A-1, vol. 6, pp. 1135-1152 (1968).

RSC Publishing, Akl et al., "Molecular materials for switchable nonlinear optics in the solid state, based on ruthenium-nitrosyl complexes", pp. 3518-3527, Porto Alegre, Brazil; May 24, 2013.

Search Report and Written Opinion dated Feb. 7, 2018 for Singapore Patent Application No. 11201609435W.

Taiwan Office Action for TW Application No. 106104501, dated Oct. 19, 2017.

Trevethan, Thomas et al. "Organic Molecules Reconstruct Nanostructures on Ionic Surfaces." Small (2011), vol. 7, No. 9, pp. 1264-1270.

U.S. Appl. No. 14/719,072, to Pavel Ivan Lazarev, filed May 21, 2015.

U.S. Appl. No. 14/752,600, to Matthew R. Robinson, et al., filed Jun. 26, 2015.

U.S. Appl. No. 14/919,337, to Paul T. Furuta, et al., filed Oct. 21, 2015.

U.S. Appl. No. 14/931,757, to Pavel Ivan Lazarev, et al., filed Nov. 3, 2015.

U.S. Appl. No. 15/043,186, to Paul T. Furuta, et al., filed Feb. 12, 2016.

U.S. Appl. No. 15/043,209, to Paul T. Furuta, et al., filed Feb. 12, 2016.

U.S. Appl. No. 15/043,247, to Barry K. Sharp, et al., filed Feb. 12, 2016.

U.S. Appl. No. 15/043,315, to Ian S.G. Kelly-Morgan, filed Feb. 12, 2014.

U.S. Appl. No. 15/043,315, to Ivan S.G. Kelley-Morgan, filed Feb. 12, 2016.

U.S. Appl. No. 15/053,943, to Pavel Ivan Lazarev, et al., filed Mar. 14, 2016.

U.S. Appl. No. 15/090,509, to Pavel Ivan Lazarev, et al., filed Mar. 4, 2016.

U.S. Appl. No. 62/121,328, to Pavel Ivan Lazarev et al., filed Feb. 26, 2015.

(56) References Cited

OTHER PUBLICATIONS

U.S. Appl. No. 62/294,949, to Pavel Ivan Lazarev, et al., filed Feb. 12, 2016.
U.S. Appl. No. 62/294,955, to Pavel Ivan Lazarev, et al., filed Feb. 12, 2016.
U.S. Appl. No. 62/294,964, to Pavel Ivan Lazarev, et al., filed Feb. 12, 2016.
U.S. Appl. No. 62/318,134, to Pavel Ivan Lazarev, et al., filed Mar. 4, 2016.
Updated Notice of Allowance for U.S. Appl. No. 14/710,480, dated Jan. 17, 2018.
Warmerdam, T. W. et al. "Discotic Liquid Crystals. Physical Parameters of some 2, 3, 7, 8, 12, 13-hexa(alkanoyloxy) truxenes: Observation of a Reentrant Isotropic Phase in a Pure Disk-like mesogen." Liquid Crystals (1988), vol. 3, No. 8, pp. 1087-1104.
Yue Wang, et. al., "Morphological and Dimensional Control via Hierarchical Assembly of Doped Oligoaniline Single Crystals", J. Am. Chem. Soc. 2012, 134, pp. 9251-9262.
Extended European Search Report dated Aug. 8, 2018 for European Patent Application No. 16756391.5.
Extended European Search Report dated Sep. 24, 2018 for European Patent Application No. 15856609.1.
Extended European Search Report dated Sep. 26, 2018 for European Patent Application No. 16797411.2.
Final Office Action for U.S. Appl. No. 15/043,247, dated Oct. 24, 2018.
Final Office Action for U.S. Appl. No. 15/043,315, dated Jun. 7, 2018.
Final Office Action for U.S. Appl. No. 15/449,587, dated Oct. 10, 2018.
Final Office Action for U.S. Appl. No. 15/710,587, dated Nov. 6, 2018.
M. Jurow et al, "Porphyrins as molectular electronic components of functional devices", Coordination Chemistry Reviews, Elsevier Science, Amsterdam NL, vol. 254, No. 19-20, Oct. 1, 2010, pp. 2297-2310.
Non-Final Office Action for U.S. Appl. No. 15/043,247, dated Feb. 19, 2019.
Non-Final Office Action for U.S. Appl. No. 15/043,247, dated Jun. 7, 2018.
Non-Final Office Action for U.S. Appl. No. 15/430,339, dated Jul. 11, 2018.
Non-Final Office Action for U.S. Appl. No. 15/430,307, dated Jul. 16, 2018.
Non-Final Office Action for U.S. Appl. No. 15/449,587, dated May 21, 2018.
Non-Final Office Action for U.S. Appl. No. 15/710,587, dated Jul. 3, 2018.
Non-Final Office Action for U.S. Appl. No. 15/782,752, dated Sep. 21, 2018.
Non-Final Office Action for U.S. Appl. No. 15/801,240, dated Oct. 19, 2018.
Non-Final Office Action for U.S. Appl. No. 15/805,016, dated Jun. 4, 2018.
Non-Final Office Action for U.S. Appl. No. 15/870,504, dated Feb. 27, 2019.
Non-Final/Final Office Action for U.S. Appl. No. 15/430,391, dated Jul. 20, 2018.
Notice of Allowance for U.S. Appl. No. 15/043,315, dated Feb. 21, 2019.
Notice of Allowance for U.S. Appl. No. 15/043,315, dated Jan. 15, 2019.
Notice of Allowance for U.S. Appl. No. 15/090,509, dated Apr. 9, 2018.
Notice of Allowance for U.S. Appl. No. 15/163,595, dated Jul. 30, 2018.
Notice of Allowance for U.S. Appl. No. 15/368,171, dated Apr. 10, 2019.
Notice of Allowance for U.S. Appl. No. 15/449,524, dated Feb. 21, 2019.
Notice of Allowance for U.S. Appl. No. 15/710,587, dated Jan. 24, 2019.
Notice of Allowance for U.S. Appl. No. 15/782,752, dated Feb. 25, 2019.
Notice of Allowance for U.S. Appl. No. 15/801,240, dated Feb. 11, 2019.
Office Action dated May 18, 2018 for Chinese Patent Application for Invention No. 201580025110.
Office Action dated Jan. 29, 2019 for Japanese Patent Application No. 2017-512654.
Supplementary Notice of Allowance for U.S. Appl. No. 14/752,600, dated Dec. 4, 2017.
Taiwanese Office Action for 886103 Application No. 106142206, dated Jul. 5, 2018.
International Search Report and Written Opinion dated Jul. 12, 2016 for International Application No. PCT/US2016/019641, to Pavel Ivan Lazarev, filed Feb. 25, 2016.
International Search Report and Written Opinion dated Jun. 7, 2017 for International Application No. PCT/US2017/24589, to Pavel Ivan Lazarev, filed Jun. 7, 2017.
International Search Report and Written Opinion dated Oct. 20, 2016 International Application No. PCT/US2016/039395, to Matthew R. Robinson, et al., filed Jun. 24, 2016.
International Search Report and Written Opinion dated Sep. 1, 2016 for International Application No. PCT/US2016/033628, to Pavel Ivan Lazarev, filed Sep. 1, 2016.
International Union of Pure and Applied Chemistry Polymer Divison Stejskal et al., "Polyaniline: Thin Films and Colloidal Dispersions (IUPAC Technical Report)", vol. 77, No. 5, pp. 815-826, Russian Academy of Sciences, St. Petersburg 199004, Russia; 2005.
Isoda, Kyosuke et al. "Truxene-Based Columnar Liquid Crystals: Self-Assembled Structures and Electro-Active Properties." Chemistry—An Asian Journal (2009), vol. 4, No. 10, pp. 1619-1625.
JACS Articles, Kang et. al., "Ultralarge Hyperpolarizability Twisted π-Electron System Electro-Optic Chromophores: Synthesis, Solid-State and Solution-Phase Structural Characteristics, Electronic Structures, Linear and Nonlinear Optical Properties, and Computational Studies", pp. 3267-3286; Perugia, Italy Feb. 20, 2007.
Jaroslav Stejskal and Irina Sapurina, "Polyaniline: Thin Films and Colloidal Dispersions (IUPAC Technical Report)", Pure and Applied Chemistry, vol. 77, No. 5, pp. 815-826 (2005).
Johnson, Kieth E. "What's an Ionic Liquid?" The Electrochemical Society Interface, Published Spring 2007, pp. 38-41, Accessed Aug. 28, 2017.
Kontrakt Technology Limited, Alla Sakharova, PhD., "Cryscade Solar Limited: Intellectual Property Portfolio summary", pp. 1-3, Cryscade Solar Limited; Apr. 9, 2015.
Li, Li-Li et al. "Synthesis and Mesomorphism of Ether-ester Mixed Tail C3-symmetrical Truxene discotic liquid crystals." Liquid Crystals(2010), vol. 37, No. 5, pp. 499-506.
Liang, Mao et al. "Synthesis and Photovoltaic Performance of Two Triarylamine Organic Dyes Based on Truxene." Yinyong Huaxue (2011) vol. 28 No. 12, pp. 1387-1392.
Lu, Meng et al. "Organic Dyes Incorporating Bis-hexapropyltruxeneamino Moiety for efficient Dye-sensitized Solar Cells." Journal of Physical Chemistry C (2011) vol. 115, No. 1, pp. 274-281.
Maddalena, Francesco "Why are Ionic Liquids, Liquids?" http://www.quora.com/why-are-ionic-liquids-liquids?, Published Jan. 26, 2017, Accessed Aug. 28, 2017.
Manukian, BK. 216. IR.-spektroskopische Untersuchungen in der Imidazol-Reihe. Helvetica Chimica Acta. 1965, vol. 48, p. 2001.
Microelectronics Research and Communications Institute, Founders et al., "High-Voltage Switching Circuit for Nanometer Scale CMOS Technologies", pp. 1-4, University of Idaho, Moscow, ID 83843 USA, Apr. 30, 2007.
Molecular Diversity Preservation International, Barber, et al. "Polymer Composite and Nanocomposite Dielectric Materials for Pulse Power Energy Storage" pp. 1-32; 29 University of South Carolina, Columbia, SC 29208 Oct. 2009.
Nagabrahmandachari et al. "Synthesis and Spectral Analysis of Tin Tetracarboxylates and Phosphinates" Indian Journal of Chemistry—Section A, 1995, vol. 34A, pp. 658-660.

(56) References Cited

OTHER PUBLICATIONS

Ni, Hai-Lang et al. "Truxene Discotic Liquid Crystals with Two Different Ring Substituents: Synthesis, Metamorphosis and High Charged Carrier Mobility ." Liquid Crystals, vol. 40, No. 3, pp. 411-420.
Non-Final Action for U.S. Appl. No. 15/043,186, dated Feb. 14, 2018.
Non-Final Office Action dated Jun. 13, 2017 for U.S. Appl. No. 15/163,595.
Non-Final Office Action for U.S. Appl. No. 14/719,072, dated Aug. 2, 2017.
Non-Final Office Action for U.S. Appl. No. 15/043,247, dated Jun. 22, 2017.
Non-Final Office Action for U.S. Appl. No. 15/043,315, dated Dec. 26 2017.
Non-Final Office Action for U.S. Appl. No. 15/053,943, dated Apr. 19, 2017.
Non-Final Office Action for U.S. Appl. No. 15/090,509, dated Jun. 22, 2017.
Non-Final Office Action for U.S. Appl. No. 15/163,595, dated Jan. 17, 2018.
Non-Final Office Action for U.S. Appl. No. 15/194,224, dated Sep. 27, 2017.
Non-Final Office Action for U.S. Appl. No. 14/710,480, dated May 8, 2017.
Non-Final Office Action for U.S. Appl. No. 14/752,600, dated Jan. 23, 2017.
Non-Final Office Action for U.S. Appl. No. 14/919,337, dated Jan. 4, 2017.
Non-Final Office Action for U.S. Appl. No. 15/043,186, dated Jun. 2, 2017.
Non-Final/Final Office Action for U.S. Appl. No. 15/043,247, dated Feb. 20, 2018.
Notice of Allowance for U.S. Appl. No. 14/710,480, dated Nov. 24, 2017.
Notice of Allowance for U.S. Appl. No. 14/710,480, dated Jan. 11, 2018.
Notice of Allowance for U.S. Appl. No. 14/710,480, dated Oct. 6, 2017.
Notice of Allowance for U.S. Appl. No. 14/719,072, dated Nov. 16, 2017.
Notice of Allowance for U.S. Appl. No. 14/752,600, dated Nov. 24, 2017.
Notice of Allowance for U.S. Appl. No. 14/752,600, dated Dec. 4, 2017.
Notice of Allowance for U.S. Appl. No. 14/752,600, dated Jul. 27, 2017.
Notice of Allowance for U.S. Appl. No. 14/919,337, dated Jul. 19, 2017.
Notice of Allowance for U.S. Appl. No. 14/919,337, dated Mar. 5, 2018.
Notice of Allowance for U.S. Appl. No. 14/919,337, dated Nov. 8, 2017.
Notice of Allowance for U.S. Appl. No. 14/931,757, dated Dec. 29, 2017.
Notice of Allowance for U.S. Appl. No. 14/931,757, dated Feb. 8, 2018.
Notice of Allowance for U.S. Appl. No. 14/931,757, dated Jul. 17, 2017.
Center for Dielectric Studies, Janosik, et al., "Ultra-High Energy Density Capacitors Through Improved Glass Technology", pp. 1-5 Center for Dielectric Studies Penn State University, dated 2004.
Chao-Hsien Ho et al., "High dielectric constant polyaniline/poly(acrylic acid) composites prepared by in situ polymerization", Synthetic Metals, Vol. 158, pp. 630-637 (2008).
Congressional Research Service, Paul W. Parfomak, "Energy Storage for Power Grids and Electric Transportation: A Technology Assessment", pp. 87-94; Members and Committees of Congress; Mar. 27, 2012.
Co-Pending U.S. Appl. No. 15/194,224, to Lazarev et al., filed Jun. 27, 2016.
Co-Pending U.S. Appl. No. 15/368,171, to Lazarev et al., filed Dec. 2, 2016.
Co-Pending U.S. Appl. No. 15/430,307, to Lazarev et al, filed Feb. 10, 2017.
Co-Pending U.S. Appl. No. 15/449,587, to Lazarev et al., filed Mar. 3, 2017.
Co-Pending U.S. Appl. No. 15/675,614, to Kelly-Morgan, filed Aug. 11, 2017.
Co-Pending U.S. Appl. No. 15/710,587, to Li et al, filed Sep. 20, 2017.
Co-Pending U.S. Appl. No. 15/469,126, to Lazarev et al, filed Mar. 24, 2017.
D C Tiwari, et al: "Temperature dependent studies of electric and dielectric properties of polythiophene based nano composite", Indian Journal of Pure & Applied PhysicsVol. 50, Jan. 2012. pp. 49-56.
Deily, Dielectric and Optical Characterization of Polar Polymeric Materials: Chromophore Entrained PMMA Thin Films, Thesis, 2008.
Department of Chemistry and Biochemistry, Hardy, et al. "Converting an Electrical Insulator into a Dielectric Capacitor: End-Capping Polystyrene with Oligoaniline"; pp. 799-807, Rensselaer Polytechnic Institute, Troy, New York 12180; Feb. 17, 2013.
Department of Chemistry, Ho et al., "High dielectric constant polyanilinelpoly(acrylic acid) composites prepared by in situ polymerization", pp. 630-637; National Taiwan University, Taipei, Taiwan, ROC, Apr. 15, 2008.
Deruiter, J. Resonance and Induction Tutorial. Auburn University-Principles of Drug Action 1 Course Material. Spring 2005, 19 pages.
Extended European Search Report . 15792494.5, dated Dec. 11, 2017.
Extended European Search Report for Application No. 15792405.1, dated Nov. 10, 2017.
Final Office Action dated Feb. 14, 2018 for U.S. Appl. No. 15/043,186.
Final Office Action dated May 2, 2017.
Final Office Action for U.S. Appl. No. 15/043,247, dated Oct. 4, 2017.
Final Office Action for U.S. Appl. No. 15/043,249, dated Feb. 6,2018.
Final Office Action for U.S. Appl. No. 15/194,224, dated Jan. 30, 2018.
Final Office Action for U.S. Appl. No. 14/919,337, dated May 1, 2017.
Handy, Scott T. "Ionic Liquids-Classes and Properties" Published Sep. 2011, Accessed Aug. 28, 2017, InTechweb.org.
Henna Ruuska et al., "A Density Functional Study on Dielectric Properties of Acrylic Acid Crafted Polypropylene", The Journal of Chemical Physics, vol. 134, p. 134904 (2011).
Hindawi Publishing Corporation, Chávez-Castillo et al, "Third-Order Nonlinear Optical Behavior of Novel Polythiophene Derivatives Functionalized with Disperse Red 19 Chromophore", pp. 1-11, International Journal of Polymer Science vol. 2015, Article ID 219361, Mar. 12, 2015.
Hindawi Publishing Corporation, González-Espasandín et al., "Fuel Cells: A Real Option for Unmanned Aerial Vehicles Propulsion", pp. 1-13, Torrej' on de Ardoz, 28850 Madrid, Spain Jan. 30, 2014.
Hindawi Publishing Corporation, Khalil Ahmed et al., "High dielectric constant polyaniline/poly(acrylic acid) composites prepared by in situ polymerization", pp. 630-637, University of the Punjab, New Campus, Lahore 54590, Oct. 17 2015.
Hsing-Yang Tsai et al, "1,6- and 1,7-Regioisomers of Asymmetric and Symmetric Perylene Bisimides: Synthesis, Characterization and Optical Properties" Molecules, 2014, vol. 19, pp. 327-341.
Hsing-Yang Tsai et al, "Synthesis and optical properties of novel asymmetric perylene bisimides", Journal of Luminescence, Vole 149, pp. 103-111 (2014).
Institute of Transportation Studies, Burke, et al. "Review of the Present and Future Applications of Supercapacitors in Electric and Hybrid Vehicles", pp. 2-23 UC Davis ITS; Dec. 2014.
International Application No. PCT/US/15/58890, to Pavel Ivan Lazarev, et al., filed Nov. 3, 2015.

(56) References Cited

OTHER PUBLICATIONS

International Search Report and Written Opinion dated Jul. 31, 2017 for International Patent Application PCT/US2017/024589.
International Search Report and Written Opinion for International Application No. PCT/US2015/030356, dated Jul. 28, 2015.
International Search Report and Written Opinion for International Application No. PCT/US2015/030415, dated Nov. 4, 2015.
International Search Report and Written Opinion for International Application No. PCT/US2015/058890, dated Feb. 25, 2016.
International Search Report and Written Opinion for International Application No. PCT/US2016/019641, dated Jul. 12, 2016.
International Search Report and Written Opinion for International Application No. PCT/US2016/033628, dated Sep. 1, 2016.
International Search Report and Written Opinion for International Application No. PCT/US2016/039395, dated Oct. 20, 2016.
International Search Report and Written Opinion for International Application No. PCT/US2016/039395, dated Jul. 1, 2016.
International Search Report and Written Opinion for International Application No. PCT/US2016/57765, dated Jan. 5, 2017.
International Search Report and Written Opinion for International Application No. PCT/US2017/016862, dated Aug. 14, 2017.
International Search Report and Written Opinion for International Application No. PCT/US2017/017146, dated May 11, 2017.
International Search Report and Written Opinion for International Application No. PCT/US2017/017150, dated May 18, 2017.
International Search Report and Written Opinion for International Application No. PCT/US2017/24150, dated Jun. 21, 2017.
International Search Report and Written Opinion for International Application No. PCT/US2017/24371, dated Aug. 2, 2017.
International Search Report and Written Opinion for International Application No. PCT/US2017/24600, dated Aug. 14, 2017.
International Search Report and Written Opinion dated Feb. 23, 2018 for International Patent Application No. PCT/US17/64252.
International Search Report and Written Opinion dated Feb. 25, 2016 for International Application No. PCT/US15/58890, to Pavel Ivan Lazarev, filed Nov. 3, 2015.

\* cited by examiner

ELECTRO-POLARIZABLE COMPOUND AND CAPACITOR

CLAIM OF PRIORITY

This application is a divisional of U.S. patent application Ser. No. 15/090,509 filed Apr. 4, 2016, the entire contents of which are incorporated herein by reference.

FIELD OF THE INVENTION

The present disclosure relates generally to passive components of electrical circuit and more particularly to an electro-polarizable compound and capacitor based on this material and intended for energy storage.

BACKGROUND

A capacitor is a passive electronic component that is used to store energy in the form of an electrostatic field, and comprises a pair of electrodes separated by a dielectric layer. When a potential difference exists between the two electrodes, an electric field is present in the dielectric layer. An ideal capacitor is characterized by a single constant value of capacitance, which is a ratio of the electric charge on each electrode to the potential difference between them. For high voltage applications, much larger capacitors have to be used.

One important characteristic of a dielectric material is its breakdown field. The breakdown field corresponds to the value of electric field strength at which the material suffers a catastrophic failure and conducts electricity between the electrodes. For most capacitor geometries, the electric field in the dielectric can be approximated by the voltage between the two electrodes divided by the spacing between the electrodes, which is usually the thickness of the dielectric layer. Since the thickness is usually constant it is more common to refer to a breakdown voltage, rather than a breakdown field. There are a number of factors that can dramatically reduce the breakdown voltage. In particular, the geometry of the conductive electrodes is important factor affecting breakdown voltage for capacitor applications. In particular, sharp edges or points hugely increase the electric field strength locally and can lead to a local breakdown. Once a local breakdown starts at any point, the breakdown will quickly "trace" through the dielectric layer until it reaches the opposite electrode and causes a short circuit.

Breakdown of the dielectric layer usually occurs as follows. Intensity of an electric field becomes high enough to "pull" electrons from atoms of the dielectric material and makes them conduct an electric current from one electrode to another. Presence of impurities in the dielectric or imperfections of the crystal structure can result in an avalanche breakdown as observed in semiconductor devices.

Another important characteristic of a dielectric material is its dielectric permittivity. Different types of dielectric materials are used for capacitors and include ceramics, polymer film, paper, and electrolytic capacitors of different kinds. The most widely used polymer film materials are polypropylene and polyester. Increasing dielectric permittivity allows for increasing volumetric energy density, which makes it an important technical task. The article "Synthesis and spectroscopic characterization of an alkoxysilane dye containing C. I. Disperse Red 1" (Yuanjing Cui, Minquan Wang, Lujian Chen, Guodong Qian, Dyes and Pigments, 62 (2004) pp. 43-47) describe the synthesis of an alkoxysilane dye (ICTES-DR1) which was copolymerized by sol-gel processing to yield organic-inorganic hybrid materials for use as second-order nonlinear optical (NLO) effect. C. I. Disperse Red 1 (DR1) was attached to Si atoms by a carbamate linkage to provide the functionalized silane via the nucleophilic addition reaction of 3-isocyanatopropyl triethoxysilane (ICTES) with DR1 using triethylamine as catalyst. The authors found that triethylamine and dibutyltin dilaurate were almost equally effective as catalysts. The physical properties and structure of ICTES-DR1 were characterized using elemental analysis, mass spectra, 1H-NMR, FTIR, UV-visible spectra and differential scanning calorimetry (DSC). ICTES-DR1 displays excellent solubility in common organic solvents.

Second-order nonlinear optical (NLO) effects of organic molecules have been extensively investigated for their advantages over inorganic crystals. Properties studied, for example, include their large optical non-linearity, ultra fast response speed, high damage thresholds and low absorption loss, etc. Particularly, organic thin films with excellent optical properties have tremendous potential in integrated optics such as optical switching, data manipulation and information processing. Among organic NLO molecules, azo-dye chromophores have been a special interest to many investigators because of their relatively large molecular hyper-polarizability (b) due to delocalization of the p-electronic clouds. They were most frequently either incorporated as a guest in the polymeric matrix (guest-host polymers) or grafted into the polymeric matrix (functionalized polymers) over the past decade.

Chromophoric orientation is obtained by applying a static electric field or by optical poling. Whatever the poling process, poled-order decay is an irreversible process which tends to annihilate the NLO response of the materials and this process is accelerated at higher temperature. For device applications, the most probable candidate must exhibit inherent properties that include: (i) high thermal stability to withstand heating during poling; (ii) high glass transition temperature ($T_g$) to lock the chromophores in their acentric order after poling.

Most of the polymers, however, have either low $T_g$ or poor thermal stability which makes them unsuitable for direct use. To overcome these problems, one attractive approach is incorporating the nonlinear optical active chromophore into a polymerizable silane by covalent bond to yield an alkoxysilane dye which can be copolymerized via sol-gel processing to form organic-inorganic hybrid materials. The hydrolysis and condensation of functionalized silicon alkoxydes can yield a rigid amorphous three-dimensional network which leads to slower relaxation of NLO chromophores. Therefore, sol-gel hybrid nonlinear optical materials have received significant attention and exhibited the desired properties. In this strategy, the design and synthesis of new network-forming alkoxysilane dye are of paramount importance and detailed investigation of them will offer great promise in the fabrication of new materials for second-order nonlinear optics that will eventually meet the basic requirements in building photonic devices.

In the article "Design and Characterization of Molecular Nonlinear Optical Switches" (Frederic Castet et al., ACCOUNTS OF CHEMICAL RESEARCH, pp. 2656-2665, (2013), Vol. 46, No. 11), Castet et al. illustrate the similarities of the experimental and theoretical tools to design and characterize highly efficient NLO switches but also the difficulties in comparing them. After providing a critical overview of the different theoretical approaches used for evaluating the first hyperpolarizabilities, Castet et al. reported two case studies in which theoretical simulations have provided guidelines to design NLO switches with improved efficiencies. The first example presents the joint theoretical/experimental characterization of a new family of multi-addressable NLO switches based on benzazolo-oxazolidine derivatives. The second focuses on the photoinduced commutation in merocyanine-spiropyran systems, where the significant NLO contrast could be exploited for metal cation identification in a new generation of multiusage sensing devices. Finally, Castet et al. illustrated the impact of environment on the NLO switching properties, with examples based on the keto-enol equilibrium in anil derivatives. Through these representative examples, Castet et al. demonstrated that the rational design of molecular NLO switches, which combines experimental and theoretical approaches, has reached maturity. Future challenges consist in extending the investigated objects to supramolecular architectures involving several NLO-responsive units, in order to exploit their cooperative effects for enhancing the NLO responses and contrasts.

Two copolymers of 3-alkylthiophene (alkyl=hexyl, octyl) and a thiophene functionalized with disperse red 19 (TDR19) as chromophore side chain were synthesized by oxidative polymerization by Marilú Chávez-Castillo et al. ("Third-Order Nonlinear Optical Behavior of Novel Polythiophene Derivatives Functionalized with Disperse Red 19 Chromophore", Hindawi Publishing Corporation International Journal of Polymer Science, Volume 2015, Article ID 219361, 10 pages, which may be downloaded from the internet at the following URL:http://dx.doi.org/10.1155/2015/219361). The synthetic procedure was easy to perform, cost-effective, and highly versatile. The molecular structure, molecular weight distribution, film morphology, and optical and thermal properties of these polythiophene derivatives were determined by NMR, FT-IR, UV-Vis GPC, DSC-TGA, and AFM. The third-order nonlinear optical response of these materials was performed with nanosecond and femtosecond laser pulses by using the third-harmonic generation (THG) and Z-scan techniques at infrared wavelengths of 1300 and 800 nm, respectively. From these experiments it was observed that although the TRD19 incorporation into the side chain of the copolymers was lower than 5%, it was sufficient to increase their nonlinear response in solid state. For instance, the third-order nonlinear electric susceptibility of solid thin films made of these copolymers exhibited an increment of nearly 60% when TDR19 incorporation increased from 3% to 5%. In solution, the copolymers exhibited similar two-photon absorption cross sections $\sigma_{2PA}$ with a maximum value of 8545GM and 233GM (1GM=$10^{-50}$ cm$^4$ s) per repeated monomeric unit.

As is generally understood by those skilled in the art, electric susceptibility refers to a dimensionless proportionality constant that indicates the degree of polarization of a dielectric material in response to an applied electric field. The greater the electric susceptibility, the greater the ability of a material to polarize in response to the field and thereby reduce the total electric field inside the material (and store energy). It is in this way that the electric susceptibility influences the electric permittivity of the material and thus influences many other phenomena in that medium, from the capacitance of capacitors. Electric susceptibility is defined as the constant of proportionality (which may be a) relating an electric field E to the induced dielectric polarization density P such that:

$$P = \varepsilon_0 \chi_e E$$

Where

P is the polarization density, $\varepsilon_0$ is the permittivity of free space, $\chi_e$ is the electric susceptibility for the material, and E is the electric field.

The standard definition of nonlinear susceptibilities in SI units is via a Taylor expansion of the polarization's reaction to electric field:

$$P = P_0 + \varepsilon_0 \chi^{(1)} + \varepsilon_0 \chi^{(2)} E^2 + \varepsilon_0 \chi^{(3)} E^3 + \ldots$$

The first susceptibility term, $\chi^{(1)}$ corresponds to the linear susceptibility described above. While this first term is dimensionless, the subsequent nonlinear susceptibilities $\chi^{(n)}$ have units of (m/V)$^{n-1}$ in SI units. The built-in polarizability $P_0$ is zero, except for ferroelectric materials. The nonlinear susceptibilities can be generalized to anisotropic materials (where each susceptibility $\chi^{(1)}$ becomes an n+1-rank tensor). The nonlinear susceptibilities are important in nonlinear optics.

The theory of molecular nonlinear optics based on a sum-over-states (SOS) model was reviewed by Mark G. Kuzyk et al., "Theory of Molecular Nonlinear Optics", Advances in Optics and Photonics 5, 4-82 (2013) doi: 10.1364/AOP 0.5.000004 (hereinafter Kuzyk), which is incorporated herein by reference. The interaction of radiation with a single wtp-isolated molecule was treated by first-order perturbation theory, and expressions were derived for the linear ($\alpha_{ij}$) polarizability and nonlinear ($\beta_{ijk}$, $\gamma_{ijkl}$) molecular hyperpolarizabilities in terms of the properties of the molecular states and the electric dipole transition moments for light-induced transitions between them. Scale invariance was used to estimate fundamental limits for these polarizabilities. The crucial role of the spatial symmetry of both the single molecules and their ordering in dense media, and the transition from the single molecule to the dense medium case (susceptibilities $\chi^{(1)}_{ij}$, $\chi^{(2)}_{ijk}$, $\chi^{(3)}_{ijkl}$), is discussed. For example, for $\beta_{ijk}$, symmetry determines whether a molecule can support second-order nonlinear processes or not. For non-centrosymmetric molecules, examples of the frequency dispersion based on a two-level model (ground state and one excited state) are the simplest possible for $\beta_{ijk}$ and examples of the resulting frequency dispersion were given. The third-order susceptibility is too complicated to yield simple results in terms of symmetry properties. Kuzyk shows that whereas a two-level model suffices for non-centrosymmetric molecules, symmetric molecules require a minimum of three levels in order to describe effects such as two-photon absorption.

The promising class of (polypyridine-ruthenium)-nitrosyl complexes capable of high yield Ru—NO/Ru—ON isomerization has been targeted as a potential molecular device for the achievement of complete NLO switches in the solid state by Joelle Akl, Chelmia Billot et al., "Molecular materials for switchable nonlinear optics in the solid state, based on ruthenium-nitrosyl complexes", New J. Chem., 2013, 37, 3518-3527, which is incorporated herein by reference. A computational investigation conducted at the PBEO/6-31+G** DFT level for benchmark systems of general formula [R-terpyridine-Ru $^{II}$Cl$_2$ (NO)](PF$_6$) (R being a substituent with various donating or withdrawing capabilities) lead to the suggestion that an isomerization could produce a convincing NLO switch (large value of the $\beta_{ON}/\beta_{OFF}$ ratio) for R substituents of weak donating capabilities. Four new molecules were obtained in order to test the synthetic feasibility of this class of materials with R=4'-p-bromophenyl, 4'-p-methoxyphenyl, 4'-p-diethylaminophenyl, and 4'-p-nitrophenyl. The different cis-(Cl,Cl) and trans-(Cl,Cl) isomers can be separated by HPLC, and identified by NMR and X-ray crystallographic studies.

Single crystals of doped aniline oligomers can be produced via a simple solution-based self-assembly method (see Yue Wang et al., "Morphological and Dimensional Control via Hierarchical Assembly of Doped Oligoaniline Single Crystals", J. Am. Chem. Soc. 2012, v. 134, pp. 9251-9262, which is incorporated herein by reference). Detailed mechanistic studies reveal that crystals of different morphologies and dimensions can be produced by a "bottom-up" hierarchical assembly where structures such as one-dimensional (1-D) nanofibers can be aggregated into higher order architectures. A large variety of crystalline nanostructures including 1-D nanofibers and nanowires, 2-D nanoribbons and nanosheets, 3-D nanoplates, stacked sheets, nanoflowers, porous networks, hollow spheres, and twisted coils can be obtained by controlling the nucleation of the crystals and the non-covalent interactions between the doped oligomers. These nanoscale crystals exhibit enhanced conductivity compared to their bulk counterparts as well as interesting structure-property relationships such as shape-dependent crystallinity. Further, the morphology and dimension of these structures can be largely rationalized and predicted by monitoring molecule-solvent interactions via absorption studies. Using doped tetraaniline as a model system, the results and strategies presented by Yue Wang et al. provide insight into the general scheme of shape and size control for organic materials.

Hu Kang et al. detail the synthesis and chemical/physical characterization of a series of unconventional twisted π-electron system electro-optic (EO) chromophores ("Ultralarge Hyperpolarizability Twisted π-Electron System Electro-Optic Chromophores: Synthesis, Solid-State and Solution-Phase Structural Characteristics, Electronic Structures, Linear and Nonlinear Optical Properties, and Computational Studies", J. AM. CHEM. SOC. 2007, vol. 129, pp. 3267-3286), which is incorporated herein by reference. Crystallographic analysis of these chromophores reveals large ring-ring dihedral twist angles (80-89°) and a highly charge-separated zwitterionic structure dominating the ground state. NOE NMR measurements of the twist angle in solution confirm that the solid-state twisting persists essentially unchanged in solution. Optical, IR, and NMR spectroscopic studies in both the solution phase and solid state further substantiate that the solid-state structural characteristics persist in solution. The aggregation of these highly polar zwitterions is investigated using several experimental techniques, including concentration-dependent optical and fluorescence spectroscopy and pulsed field gradient spin-echo (PGSE) NMR spectroscopy in combination with solid-state data. These studies reveal clear evidence of the formation of centrosymmetric aggregates in concentrated solutions and in the solid state and provide quantitative information on the extent of aggregation. Solution-phase DC electric-field-induced second-harmonic generation (EFISH) measurements reveal unprecedented hyperpolarizabilities (nonresonant $\mu\beta$ as high as $-488\,000\times10^{48}$ esu at 1907 nm). Incorporation of these chromophores into guest-host poled polyvinylphenol films provides very large electro-optic coefficients ($r_{33}$) of ~330 pm/V at 1310 nm. The aggregation and structure-property effects on the observed linear/nonlinear optical properties were discussed. High-level computations based on state-averaged complete active space self-consistent field (SA-CASSCF) methods provide a new rationale for these exceptional hyperpolarizabilities and demonstrate significant solvation effects on hyperpolarizabilities, in good agreement with experiment. As such, this work suggests new paradigms for molecular hyperpolarizabilities and electro-optics.

Capacitors as energy storage device have well-known advantages versus electrochemical energy storage, e.g. a battery. Compared to batteries, capacitors are able to store energy with very high power density, i.e. charge/recharge rates, have long shelf life with little degradation, and can be charged and discharged (cycled) hundreds of thousands or millions of times. However, capacitors often do not store energy in small volume or weight as in case of a battery, or at low energy storage cost, which makes capacitors impractical for some applications, for example electric vehicles. Accordingly, it may be an advance in energy storage technology to provide capacitors of higher volumetric and mass energy storage density and lower cost.

SUMMARY

The present disclosure provides an electro-polarizable compound having the following general formula (I):

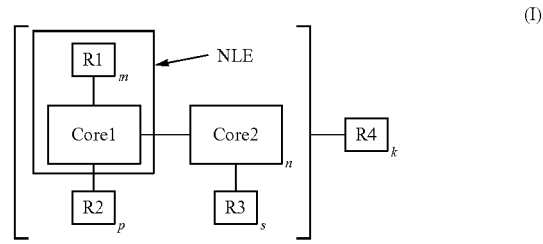

(I)

Where Core1 is an aromatic polycyclic conjugated molecule having two-dimensional flat form and self-assembling by pi-pi stacking in a column-like supramolecule, R1 is a dopant group connected to the aromatic polycyclic conjugated molecule (Core1), m is the number of dopant groups R1 which is equal to 1, 2, 3 or 4, R2 is a substituent comprising one or more ionic groups from a class of ionic compounds that are used in ionic liquids connected to the aromatic polycyclic conjugated molecule (Core1) directly or via a connecting group, p is number of ionic groups R2 which is equal to 0, 1, 2, 3 or 4. The fragment marked NLE containing the aromatic polycyclic conjugated molecule with at least one dopant of group has nonlinear effect of polarization. The Core2 is an electro-conductive oligomer self-assembling by pi-pi stacking in a column-like supramolecule, n is number of the electro-conductive oligomers which is equal to 0, 2, or 4, R3 is a substituent comprising one or more ionic groups from a class of ionic compounds that are used in ionic liquids connected to the electro-conductive oligomer (Core2) directly or via a connecting group, s is number of the ionic groups R3 which is equal to 0, 1, 2, 3 or 4. The R4 is a resistive substituent providing solubility of the organic compound in a solvent and electrically insulating the column-like supramolecules from each other, k is the number of R4 substituents, on said electro-polarizable compound, which is equal to 0, 1, 2, 3, 4, 5, 6, 7 or 8.

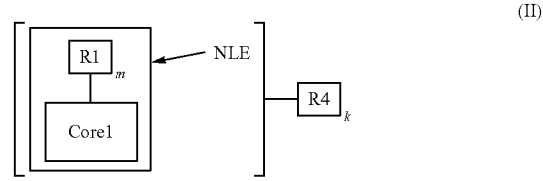

(II)

In one aspect, the present disclosure provides a solution comprising an organic solvent and at least one disclosed electro-polarizable compound.

In another aspect, the present disclosure provides a crystal metadielectric layer comprising a mixture of the electro-polarizable compounds as disclosed above. The nonlinearly polarizable fragments comprising an aromatic polycyclic conjugated molecule with at least one dopant group, optionally the electro-conductive oligomers, and the ionic groups which have electronic and/or ionic type of polarizability are placed into the resistive dielectric envelope formed by resistive substituents providing solubility of the organic compound in a solvent and electrically insulating the column-like supramolecules from each other.

In still another aspect, the present disclosure provides a meta-capacitor comprising two metal electrodes positioned parallel to each other and which can be rolled or flat and planar with said metadielectric layer between said electrodes, wherein the dielectric layer comprises one or more types of the disclosed electro-polarizable compounds. The nonlinearly polarizable fragments may include an aromatic polycyclic conjugated molecule with at least one dopant group. Optionally the electro-conductive oligomers, and the ionic groups which have electronic and/or ionic type of polarizability are placed into the resistive dielectric envelope formed by resistive substituents providing solubility of the organic compound in a solvent and electrically insulating the column-like supramolecules from each other.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1A:
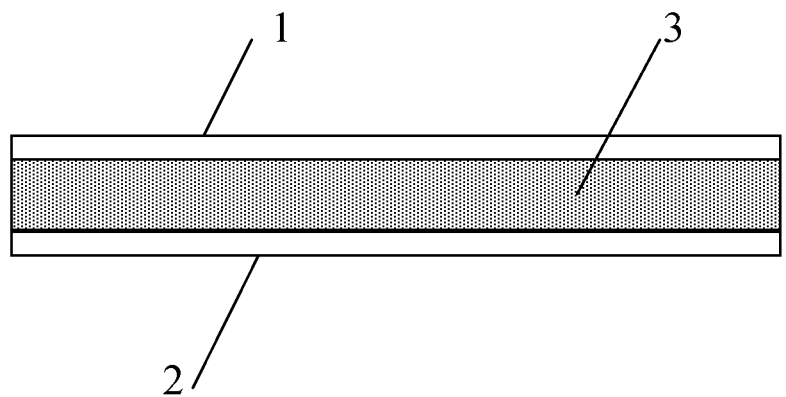
FIG. 1A schematically shows a capacitor with flat and planar electrodes in accordance with an aspect of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides an electro-polarizable compound. Existence of the electrophilic groups (acceptors) and the nucleophilic groups (donors) in the aromatic polycyclic conjugated molecule (Core1) promotes increase of electronic polarizability of these molecules. Under the influence of external electric field electrons are displaced from the nucleophilic groups (donors) to the electrophilic groups (acceptors) that lead to increase of an electronic polarizability of such molecules. Thus a distribution of electronic density in the molecules is non-uniform. Presence of the electro-conductive oligomers leads to increasing of polarization ability of the disclosed electro-polarizable compound because of electronic super conductivity of the electro-conductive oligomers. Ionic groups increase an ionic component of polarization of the disclosed electro-polarizable compound. The nonlinearly polarizable fragments comprising an aromatic polycyclic conjugated molecule with at least one dopant group, the electro-conductive oligomers and the ionic groups are placed into the resistive dielectric envelope formed by resistive substituents providing solubility of the organic compound in a solvent and electrically insulating the column-like supramolecules from each other. A non-centro-symmetric arrangement of the dopant group(s) can lead to a strong nonlinear response of the compound's electronic polarization in the presence of an electric field. The resistive substituents increase the electric strength of these electro-polarizable compounds and breakdown voltage of the dielectric layers made on their basis.

In one embodiment of the present disclosure, the aromatic polycyclic conjugated molecule (Core1) comprises rylene fragments. In another embodiment of the disclosed electro-polarizable compound, the rylene fragments are selected from structures from 1 to 12 as given in Table 1.

TABLE 1

Examples of the aromatic polycyclic conjugated molecule comprising rylene fragments

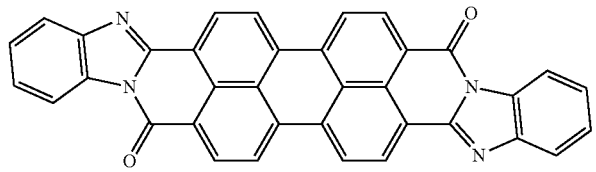 [SMILES: O=c1c2ccc3c4ccc5c6c(ccc(c7ccc(c2c37)c2nc3ccccc3n12)c46)c(=O)n1c2ccccc2nc51]

1

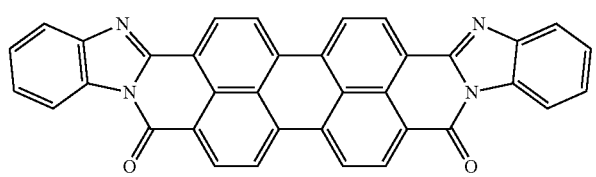 [SMILES: O=c1c2ccc3c4ccc5c(=O)n6c7ccccc7nc6c6ccc(c7ccc(c2c37)c2nc3ccccc3n12)c4c56]

2

TABLE 1-continued
Examples of the aromatic polycyclic conjugated molecule comprising rylene fragments
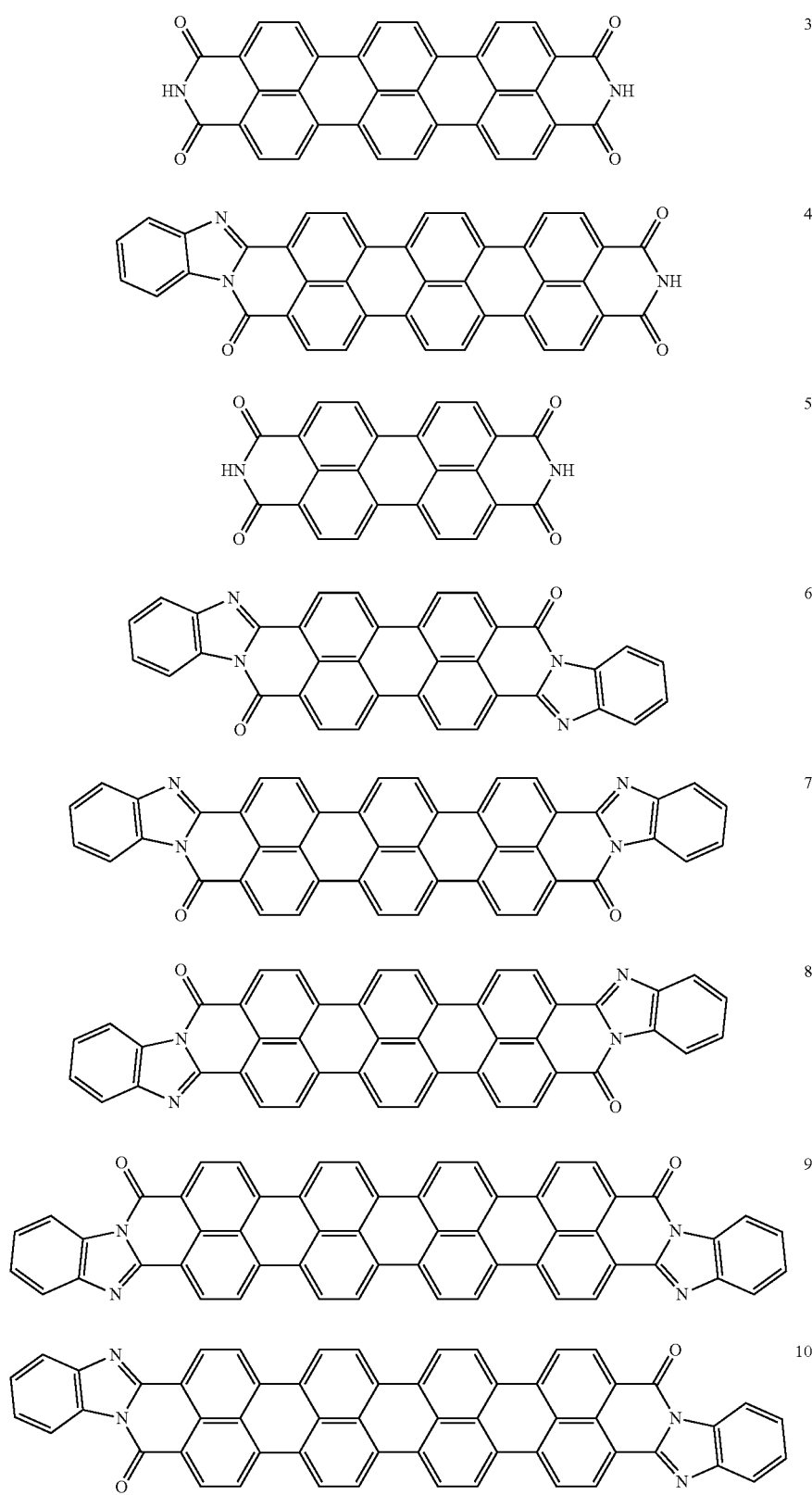

TABLE 1-continued

Examples of the aromatic polycyclic conjugated molecule comprising rylene fragments

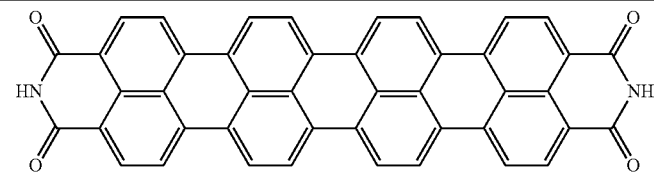
11

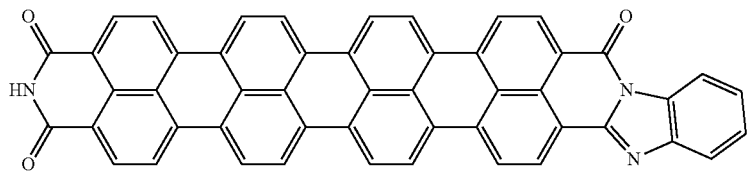 [SMILES: O=C1NC(=O)c2ccc3c4ccc5c6ccc7c8ccc9c%10c(ccc(c%11ccc(c%12ccc(c%13ccc1c2c%133)c4c%125)c6c%117)c8%10)c(=O)n1c2ccccc2nc91]
12

In yet another embodiment of the electro-polarizable compound, the aromatic polycyclic conjugated molecule (Core1) is tetrapirolic macro-cyclic fragment. In still another embodiment of the electro-polarizable compound, the tetrapirolic macro-cyclic fragments have a general structural formula from the group comprising structures 13-19 as given in Table 2, where M denotes an atom of metal or two protons (2H).

TABLE 2

Examples of the aromatic polycyclic conjugated molecule comprising tetrapirolic macro-cyclic fragment

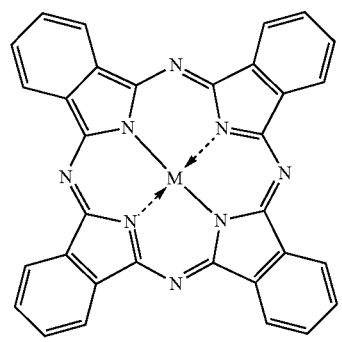
13

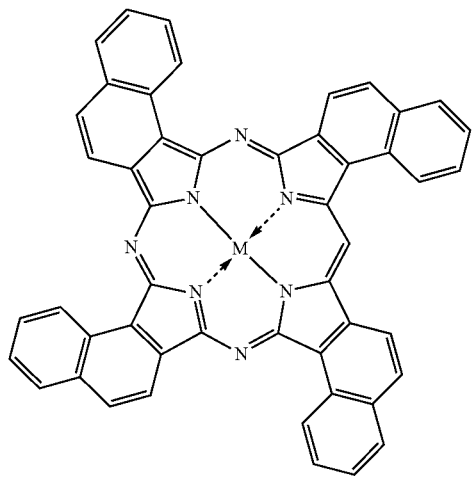
14

TABLE 2-continued

Examples of the aromatic polycyclic conjugated molecule comprising tetrapirolic macro-cyclic fragment

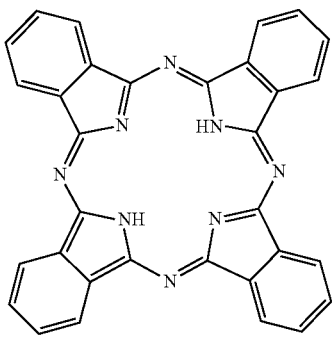 [SMILES: c1ccc2c(c1)-c1nc-2nc2[nH]c(nc3nc(nc4[nH]c(n1)c1ccccc41)-c1ccccc1-3)c1ccccc21]
15

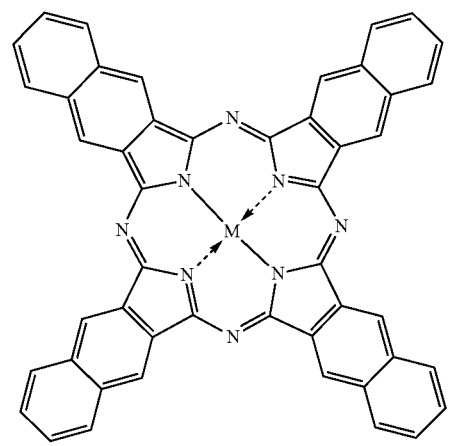
16

TABLE 2-continued

Examples of the aromatic polycyclic conjugated molecule comprising tetrapirolic macro-cyclic fragment

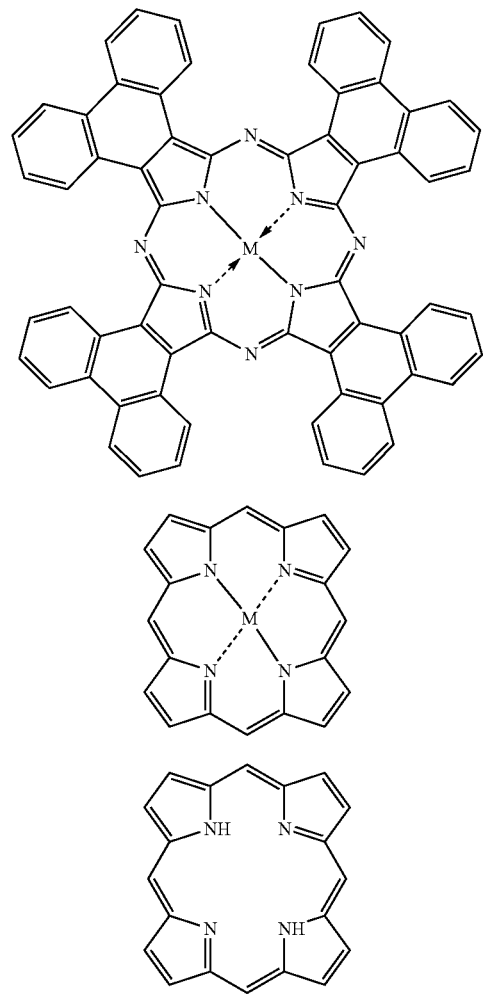

17

18

19

In one embodiment of the present disclosure, the dopant group (R1) is selected from nucleophilic groups (donors) and electrophilic groups (acceptors). The electrophilic groups (acceptors) are selected from —NO$_2$, —NH$_3^+$ and —NR$_3^+$ (quaternary nitrogen salts), counterion Cl$^-$ or Br$^-$, —CHO (aldehyde), —CRO (keto group), —SO$_3$H (sulfonic acids), —SO$_3$R (sulfonates), SO$_2$NH$_2$ (sulfonamides), —COOH (carboxylic acid), —COOR (esters, from carboxylic acid side), —COCl (carboxylic acid chlorides), —CONH$_2$ (amides, from carboxylic acid side), —CF$_3$, —CCl$_3$, —CN, wherein R is radical selected from the list comprising alkyl (methyl, ethyl, isopropyl, tert-butyl, neopentyl, cyclohexyl etc.), allyl (—CH$_2$—CH═CH$_2$), benzyl (—CH$_2$C$_6$H$_5$) groups, phenyl (+substituted phenyl) and other aryl (aromatic) groups. The nucleophilic groups (donors) are selected from —O$^-$ (phenoxides, like —ONa or —OK), —NH$_2$, —NHR, NR$_2$, —OH, OR (ethers), —NH-COR (amides, from amine side), —OCOR (esters, from alcohol side), alkyls, —C$_6$H$_5$, vinyls, wherein R is radical selected from the list comprising alkyl (methyl, ethyl, isopropyl, tert-butyl, neopentyl, cyclohexyl etc.), allyl (—CH2-CH═CH2), benzyl (—CH2C6H5) groups, phenyl (+substituted phenyl) and other aryl (aromatic) groups.

In another embodiment of the present disclosure, the electro-conductive oligomer (Core2) is selected from the structures 20 to 28 as given in Table 3, wherein I=2, 3, 4, 5, 6, 7, 8, 9, 10, 11 or 12, Z is ═O, ═S or ═NR5, and R5 is selected from the group consisting of unsubstituted or substituted C$_1$-C$_{18}$alkyl, unsubstituted or substituted C$_2$-C$_{18}$alkenyl, unsubstituted or substituted C$_2$-C$_{18}$alkynyl, and unsubstituted or substituted C$_4$-C$_{18}$aryl.

TABLE 3

Examples of the polycyclic organic compound comprising electro-conductive oligomer

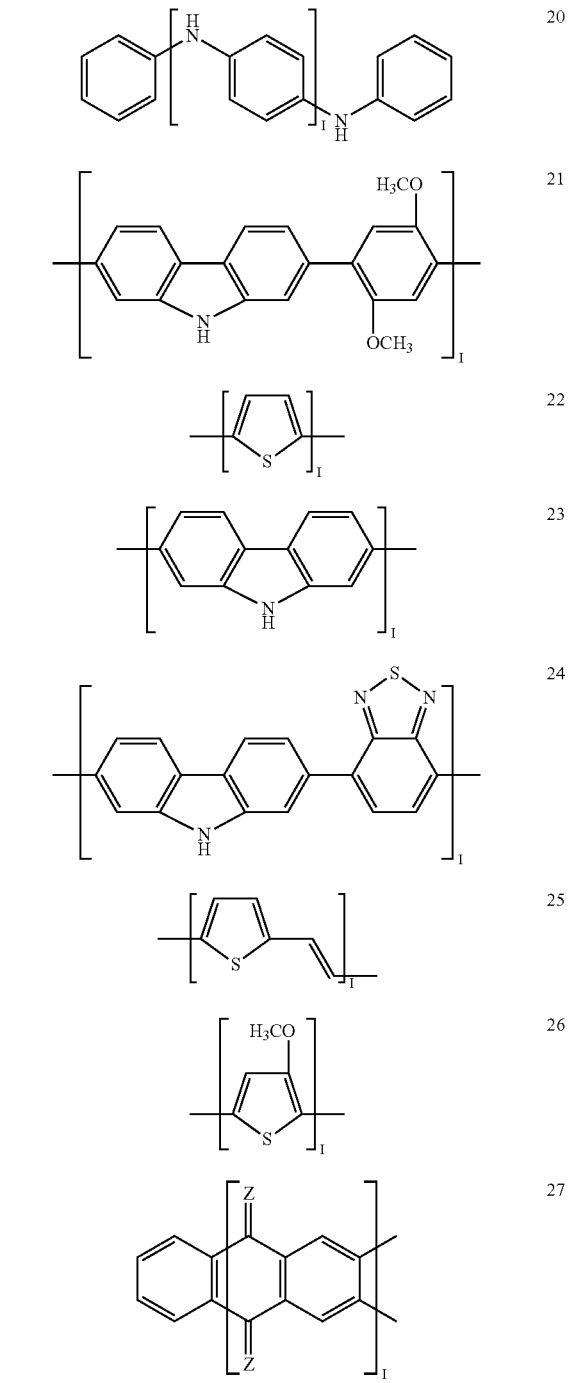

20

21

22

23

24

25

26

27

TABLE 3-continued

Examples of the polycyclic organic compound comprising electro-conductive oligomer

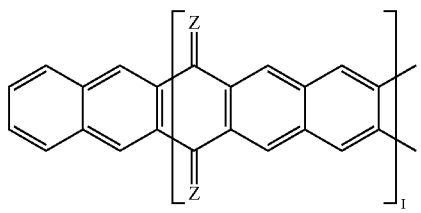
28

In yet another embodiment of the disclosed electro-polarizable compound, at least one ionic group R2 or R3 is independently selected from the list comprising $[NR_4]^+$, $[PR_4]^+$ as cation and $[-CO_2]^-$, $[-SO_3]^-$, $[-SR_5]^-$, $[-PO_3R]^-$, $[-PR_5]^-$ as anion, wherein R is selected from the list comprising H, alkyl, and fluorine. In still another embodiment of the disclosed electro-polarizable compound, at least one connecting group is selected from the list comprising the following structures: 29-39 given in Table 4, where W is hydrogen (H) or an alkyl group.

TABLE 4

Examples of the connecting group

| | |
|---|---|
| —O— | 29 |
|  | 30 |
|  | 31 |
| 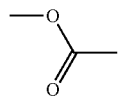 | 32 |
| 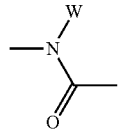 | 33 |
| 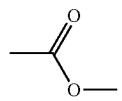 | 34 |
| 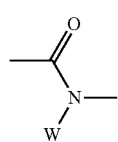 | 35 |
| 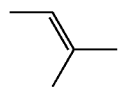 | 36 |
| 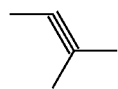 | 37 |

TABLE 4-continued

Examples of the connecting group

| | |
|---|---|
| 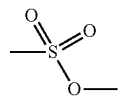 | 38 |
| 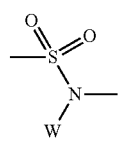 | 39 |

In one embodiment of the present disclosure, the at least one connecting group is selected from the group of $CH_2$, $CF_2$, $SiR_2O$, $CH_2CH_2O$, wherein R is selected from the list comprising H, alkyl, and fluorine. In another embodiment of the present disclosure, the at least one connecting group is selected from structures 40 to 45 as given in table 5.

TABLE 5

Examples of the connecting group

| | |
|---|---|
| 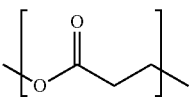 | 40 |
| 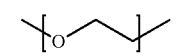 | 41 |
| 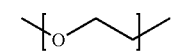 | 42 |
| 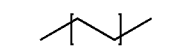 | 43 |
| 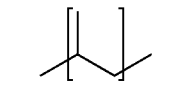 | 44 |
|  | 45 |

In yet another embodiment of the present disclosure, the resistive substituent R4 is selected from the group of alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, n-butyl, iso-butyl and tert-butyl groups, and the aryl group is selected from phenyl, benzyl and naphthyl groups or siloxane, and/or polyethyleneglycol as linear or branched chains. In still another embodiment of the present disclosure, the resistive substituent R4 is $C_XQ_{2X+1}$, where X≥1 and Q is hydrogen (H), fluorine (F), or chlorine (Cl).

In one embodiment of the electro-polarizable compound, the aromatic polycyclic conjugated molecule (Core1) and the dopant groups (R1) form a non-centrosymmetric molecular structure. In another embodiment of the electro-polarizable compound, the aromatic polycyclic conjugated molecule (Core1), the dopant groups (R1) and the resistive substituents (R4) form a non-centrosymmetric molecular structure.

In one embodiment of the present disclosure, the electro-polarizable compound has the following general formula (II):

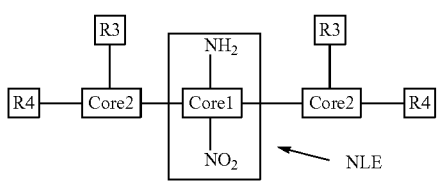
(II)

The aromatic polycyclic conjugated molecule (Core1) is rylene fragment having following structural formula:

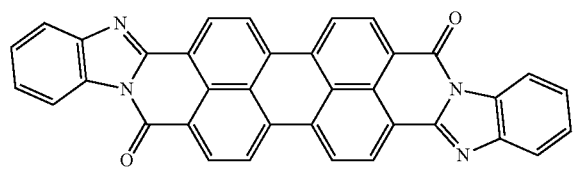

Two (m is equal to 2) dopant groups —NH$_2$ and —NO$_2$ are located on rylene phenyl rings and/or apex phenyl ring of Core1. The electro-conductive oligomer (Core2) has following structural formula wherein I=2, 3, 4, 5, 6, 7, 8, 9, 10, 11 or 12:

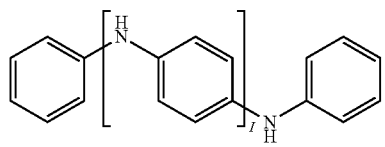

The number n of the electro-conductive oligomers is equal to 2 and the two Core2 are located in apex positions of the Core1, R3 is the ionic group [—SO$_3$]$^-$, the number s of the ionic groups R3 is equal to 2, the ionic groups are connected to the electro-conductive oligomer (Core2) via a connecting group having following structural formula:

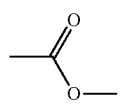

The group R4 is C$_{18}$H$_{37}$-resistive substituent located in side (lateral) position of the Core2.

In another embodiment of the present disclosure, the electro-polarizable compound has the following general formula (III):

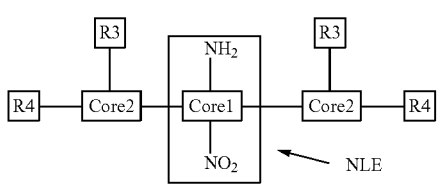
(III)

The aromatic polycyclic conjugated molecule (Core1) is a tetrapirolic macro-cyclic fragment having the following structural formula:

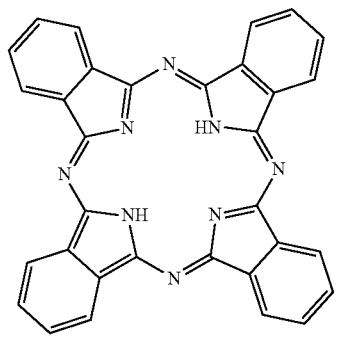 [SMILES: c1ccc2c(c1)-c1nc-2nc2[nH]c(nc3nc(nc4[nH]c(n1)c1ccccc41)-c1ccccc1-3)c1ccccc21]

In this example, there are two dopant groups so m is equal to 2. The two dopant groups —NH$_2$ and —NO$_2$ are located on opposite apex positions of the Core1, the electro-conductive oligomer (Core2) has following structural formula, wherein I=2, 3, 4, 5, 6, 7, 8, 9, 10, 11 or 12:

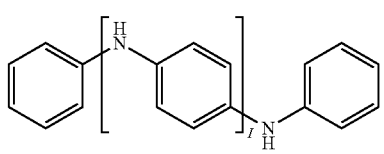

The number n of the electro-conductive oligomers is equal to 2 and the two Core2 are located in apex positions of the Core1, R3 is the ionic group COO$^-$, number s of the ionic groups R3 is equal to 2, the ionic groups are connected to the electro-conductive oligomer (Core2) via a connecting group having following structural formula:

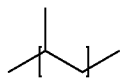

The group R4 is (C$_1$-C$_{20}$)alkyl-resistive substituent located in side (lateral) position of the Core2.

In another embodiment of the electro-polarizable compound, a fragment comprising the aromatic polycyclic conjugated molecule (Core1), dopant groups (R1) and/or resistive substituents providing solubility of the organic compound in a solvent and electrically insulating the column-like supramolecules from each other (R4) is selected from structures 46 to 97 as given in Table 6.

TABLE 6
Examples of the fragment comprising the aromatic polycyclic conjugated molecule
(Core1)
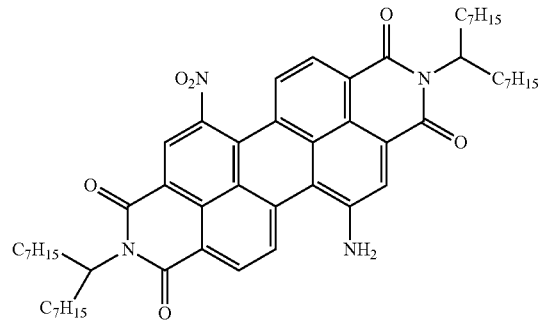
46
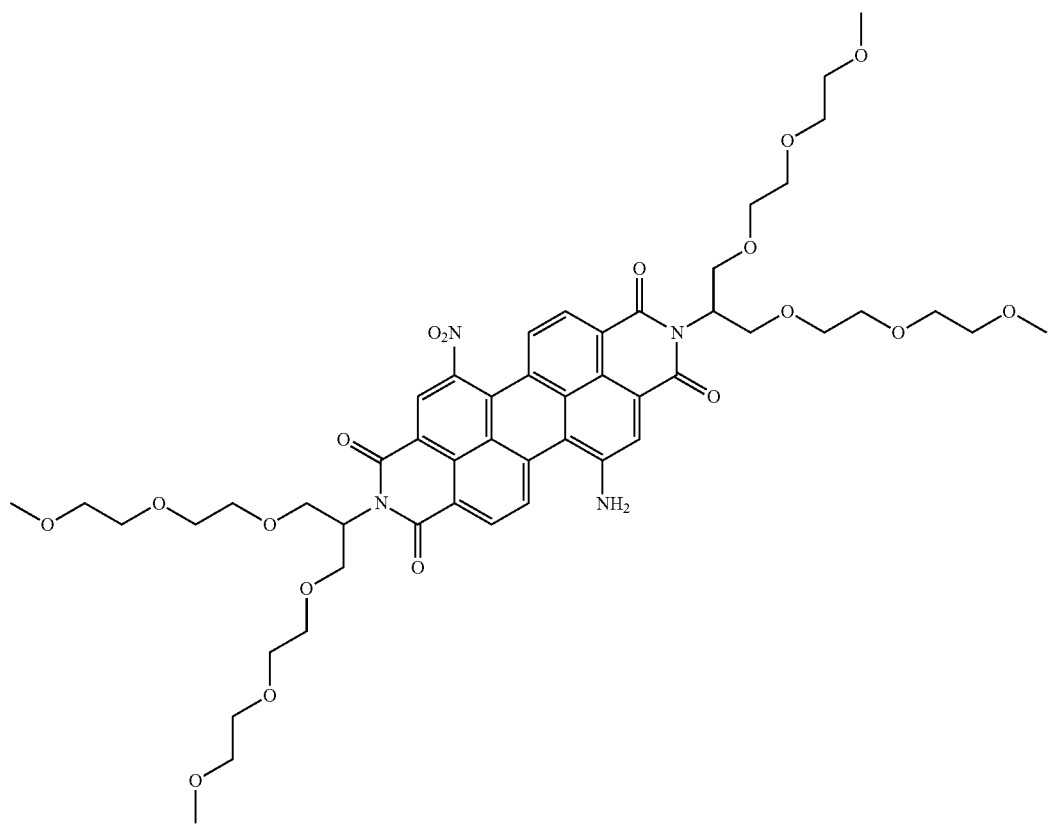
47
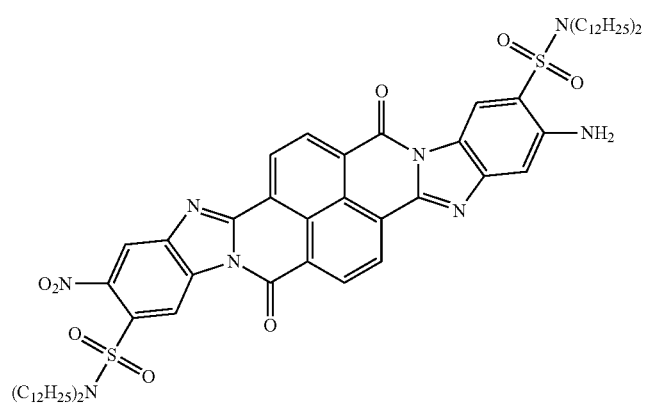
48

TABLE 6-continued
Examples of the fragment comprising the aromatic polycyclic conjugated molecule
(Core1)
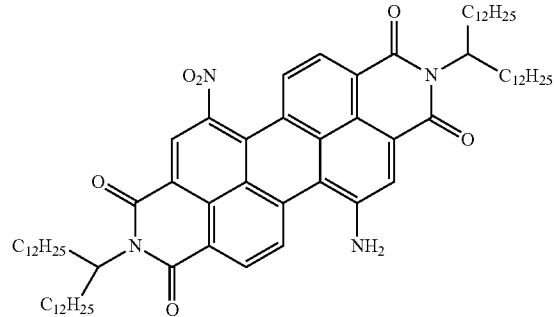
49
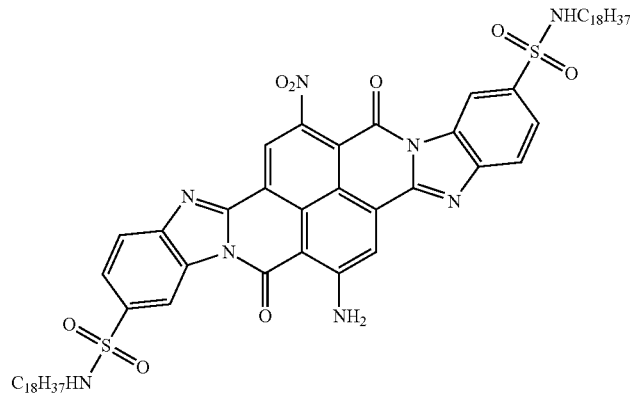
50
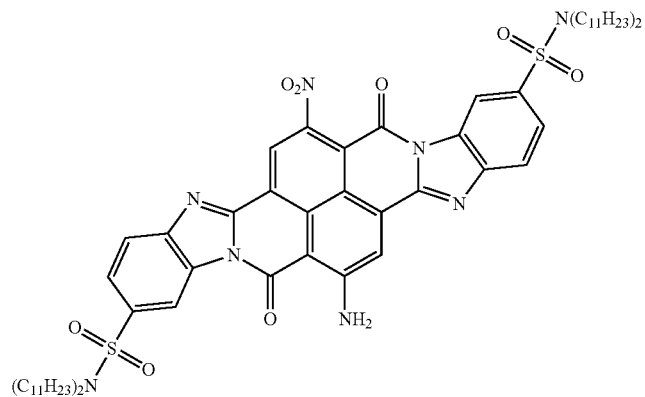
51
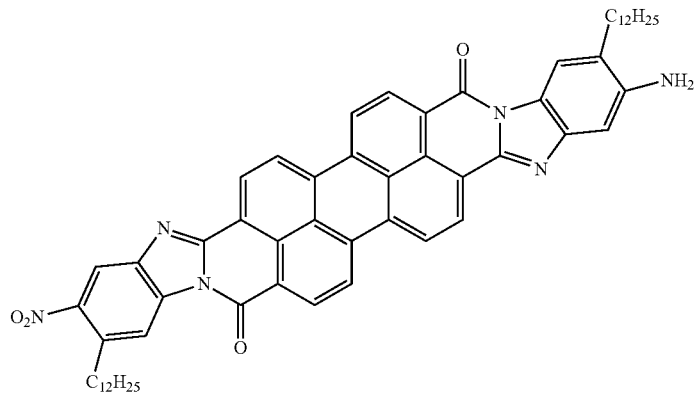
52

TABLE 6-continued
Examples of the fragment comprising the aromatic polycyclic conjugated molecule
(Core1)
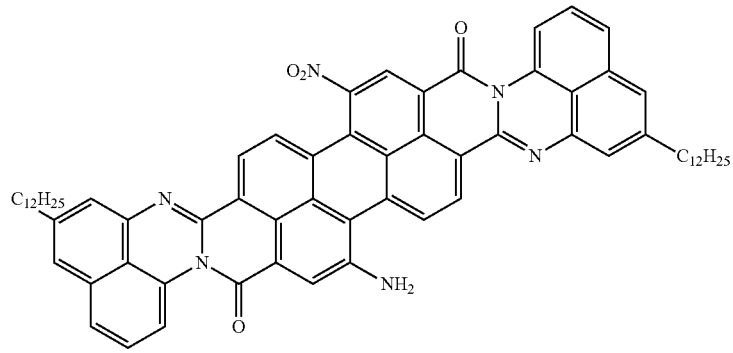
53
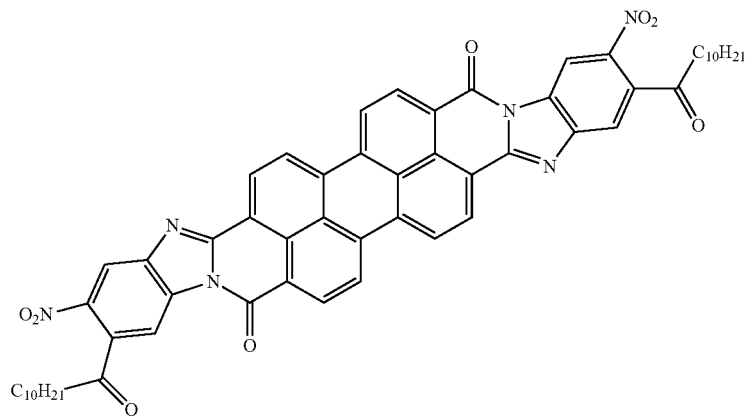
54
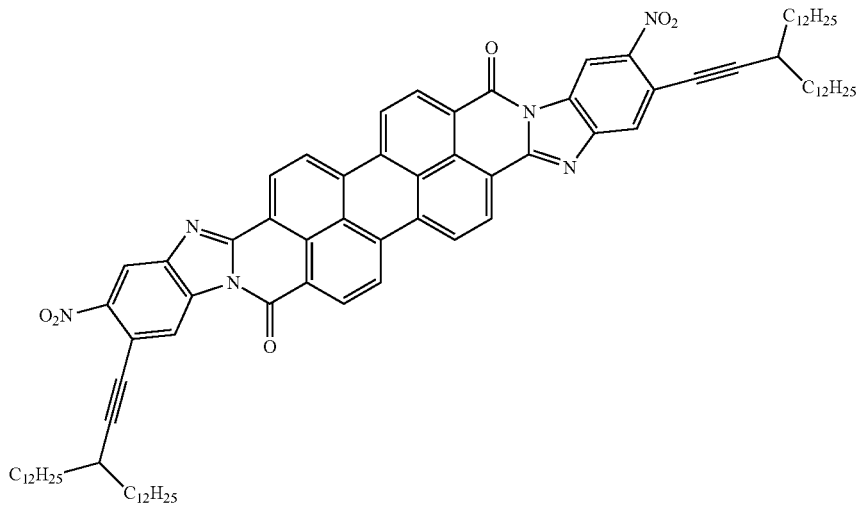
55
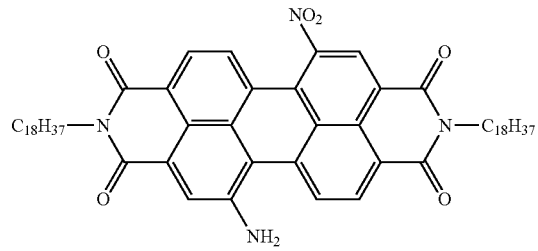
56

TABLE 6-continued
Examples of the fragment comprising the aromatic polycyclic conjugated molecule
(Core1)
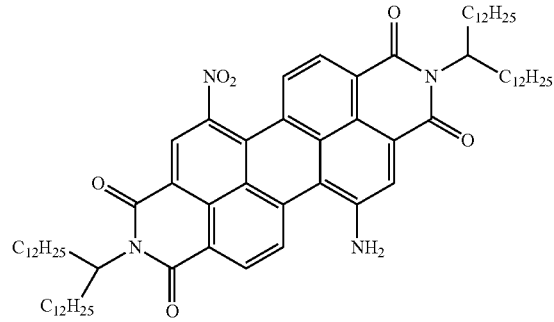
57
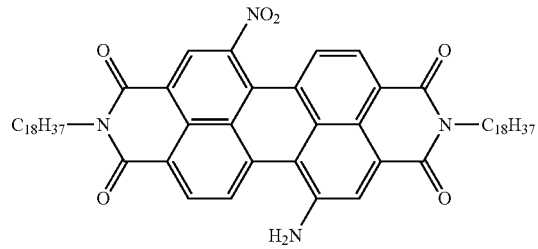
58
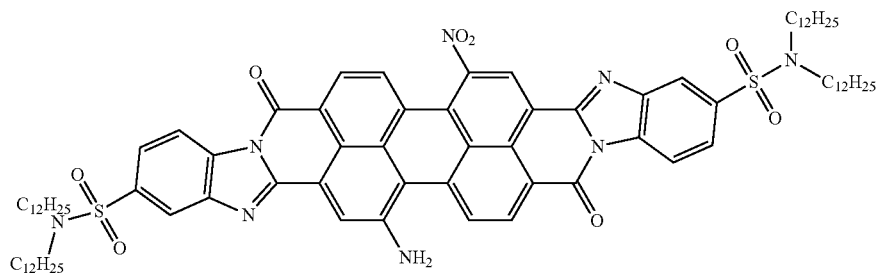
59
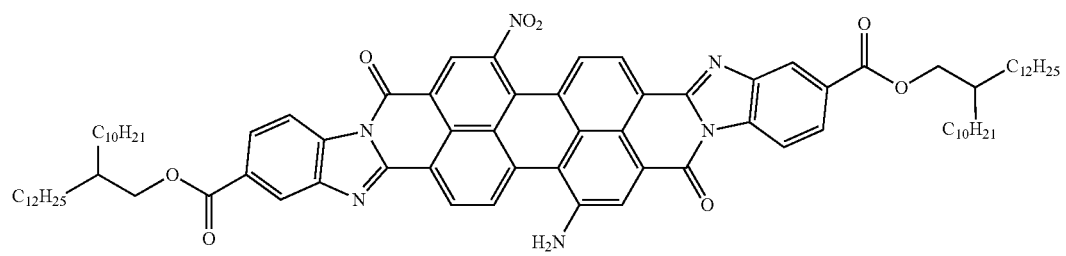
60
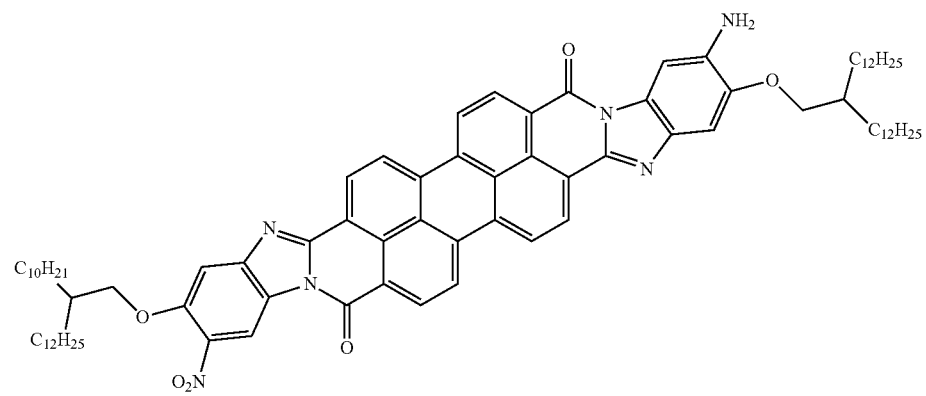
61

TABLE 6-continued
Examples of the fragment comprising the aromatic polycyclic conjugated molecule
(Core1)
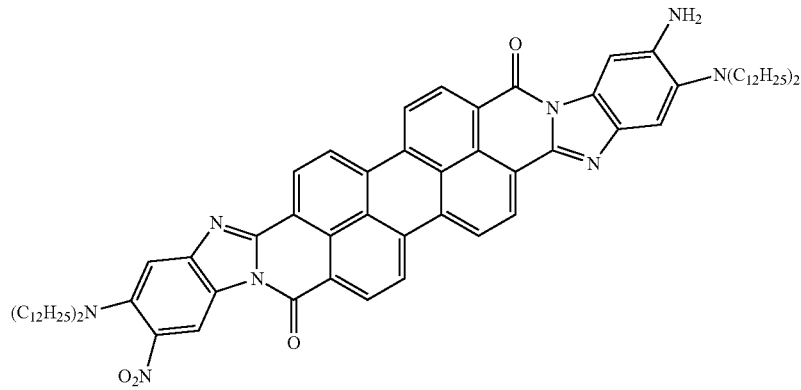
62
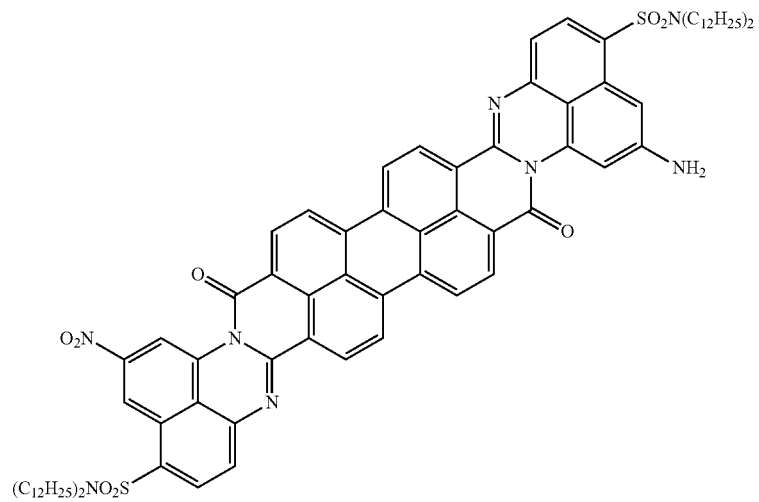
63
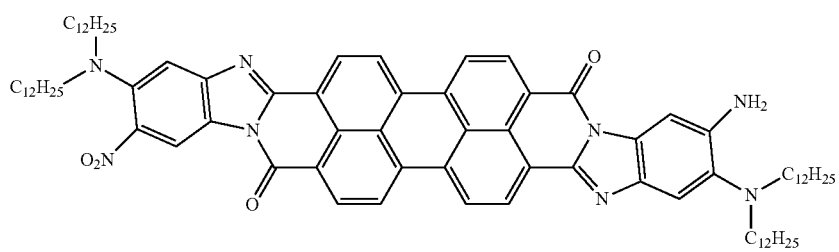
64
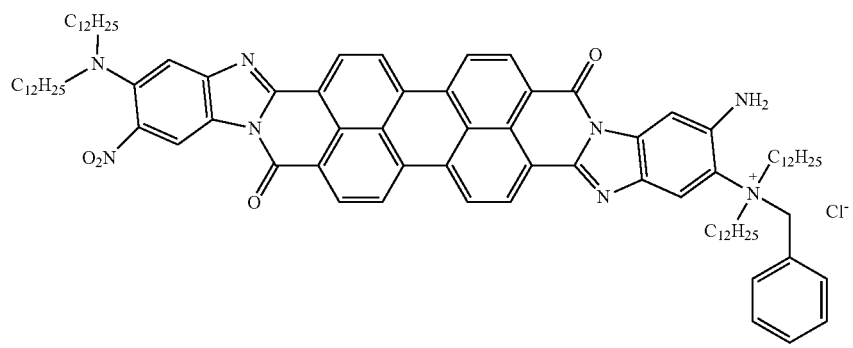
65

TABLE 6-continued
Examples of the fragment comprising the aromatic polycyclic conjugated molecule
(Core1)
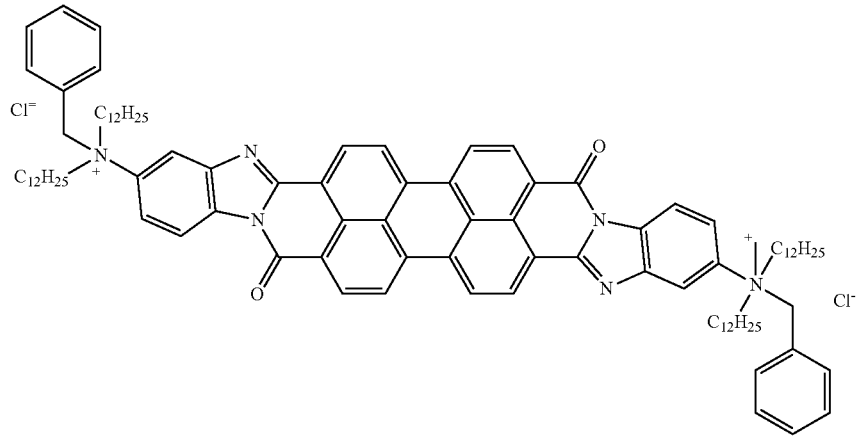
66
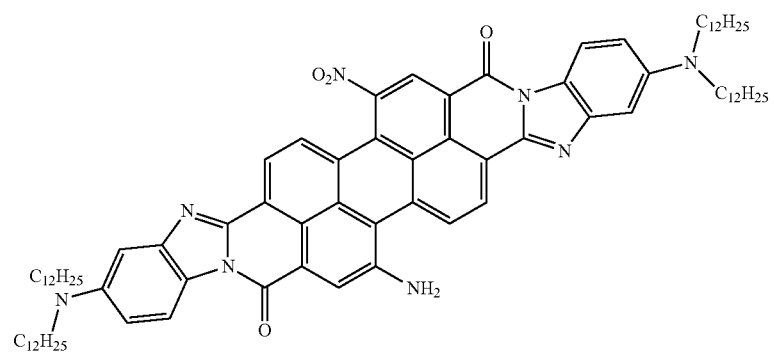
67
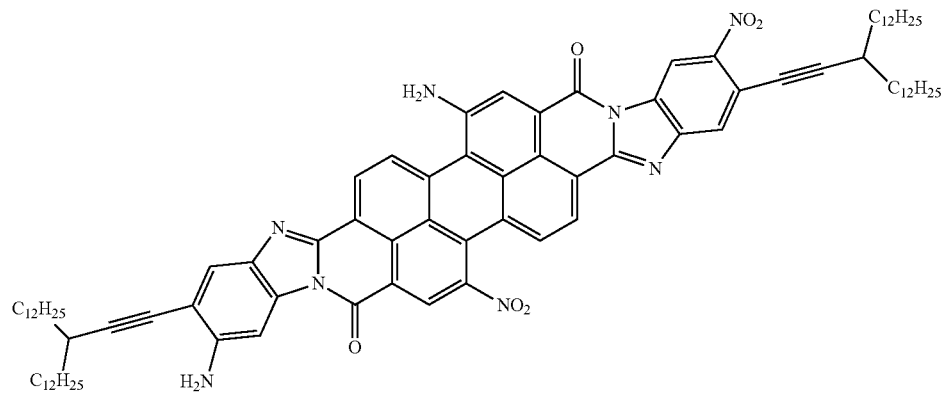
68
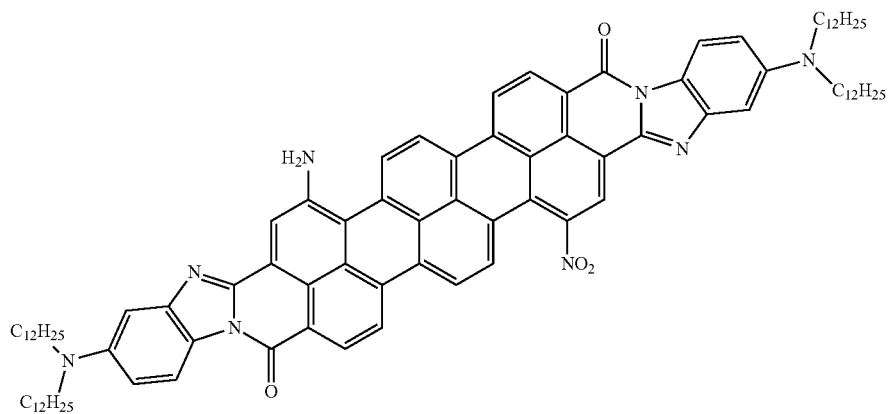
69

TABLE 6-continued
Examples of the fragment comprising the aromatic polycyclic conjugated molecule
(Core1)
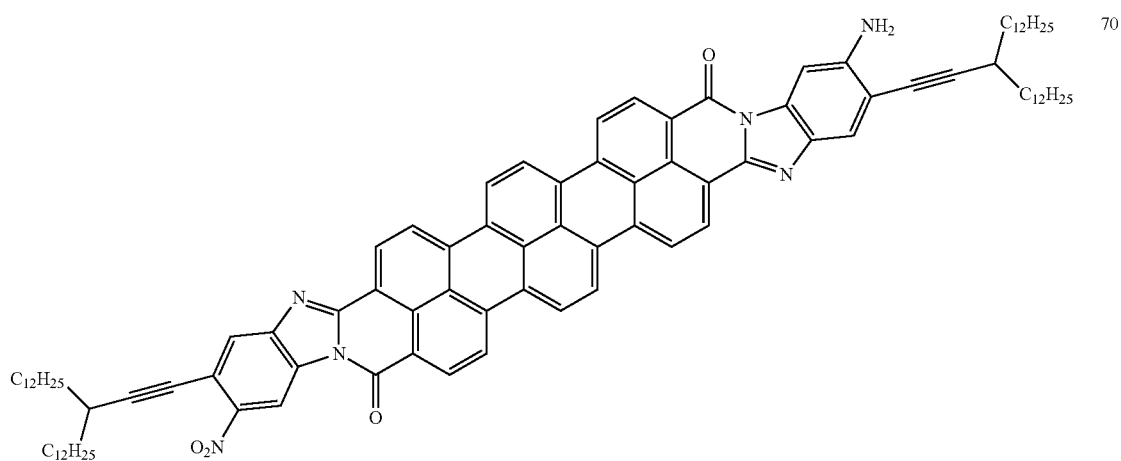
70
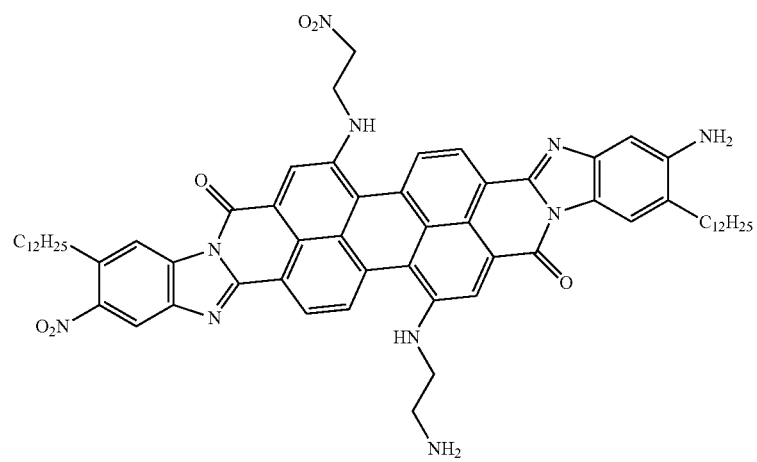
71
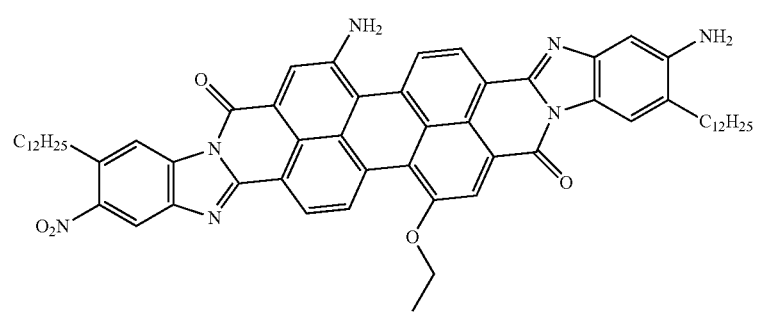
72

US 10,707,019 B2
33                                                                                       34
TABLE 6-continued
Examples of the fragment comprising the aromatic polycyclic conjugated molecule
(Core1)
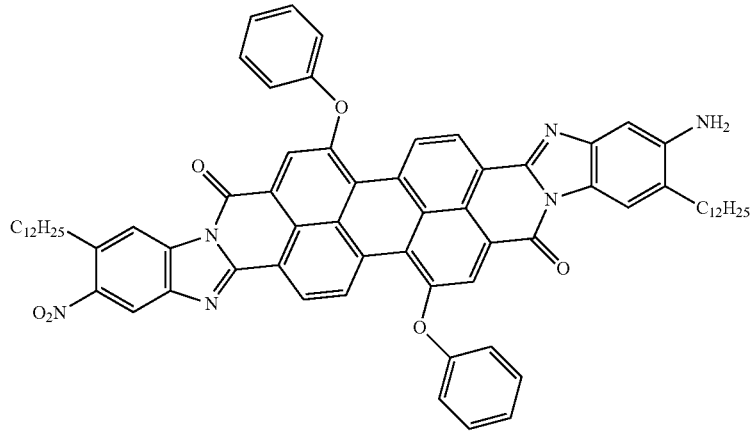
73
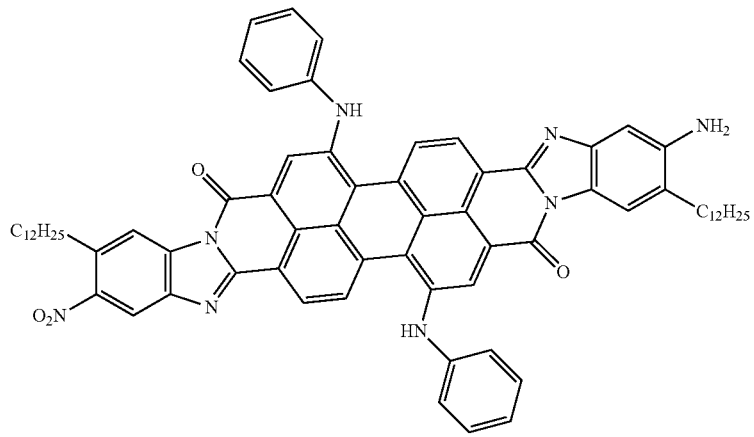
74
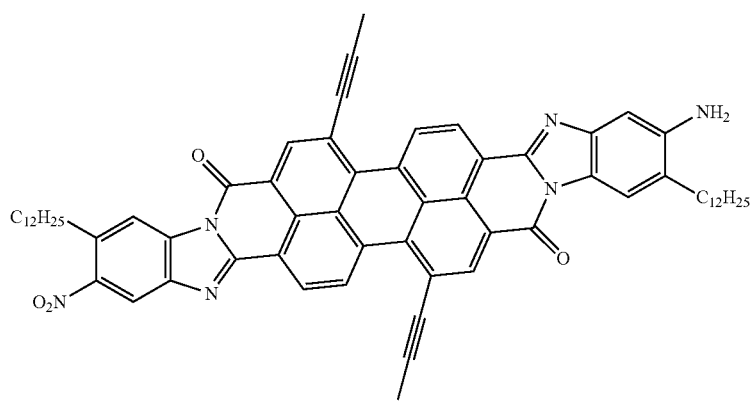
75
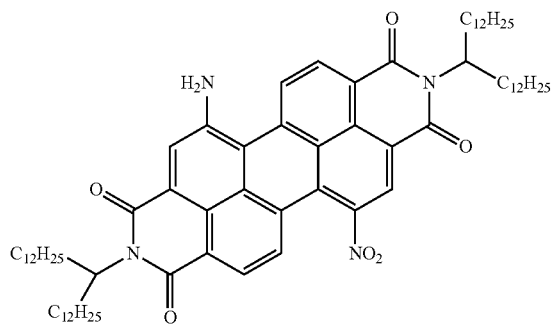
76

TABLE 6-continued
Examples of the fragment comprising the aromatic polycyclic conjugated molecule
(Core1)
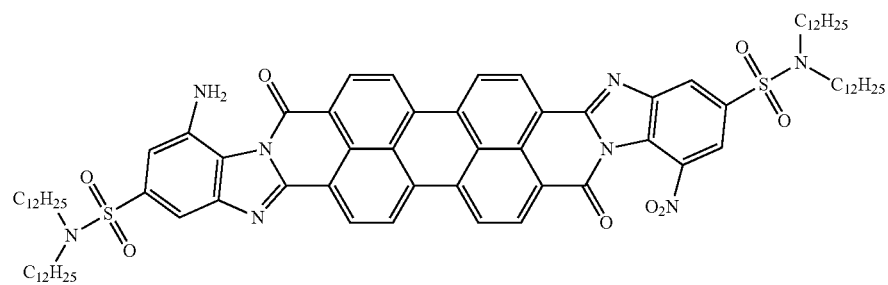
77
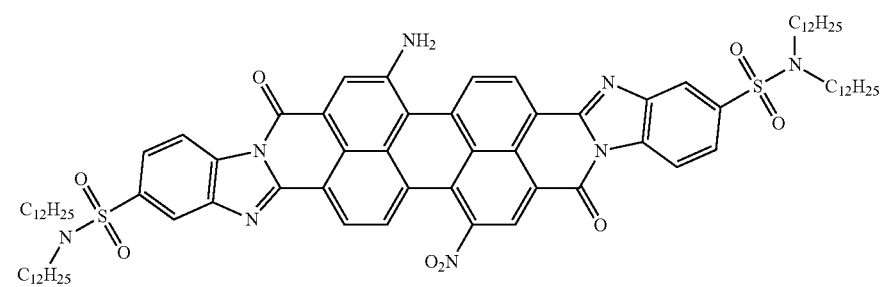
78
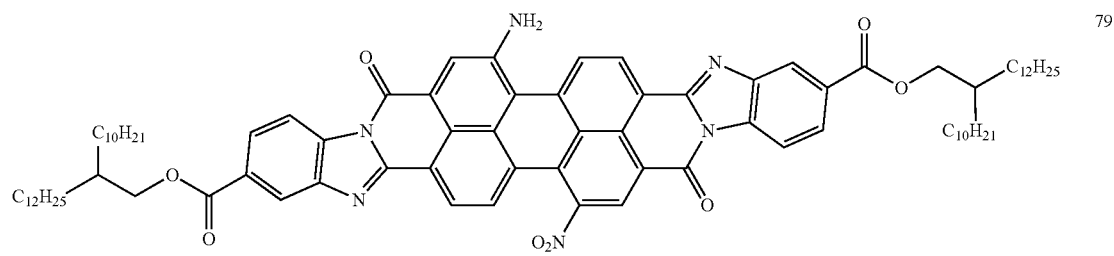
79
80
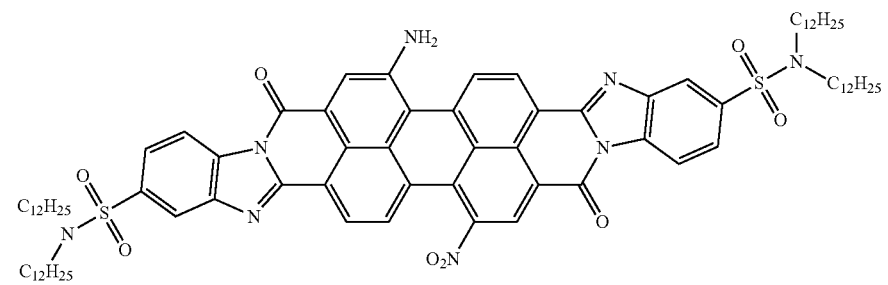
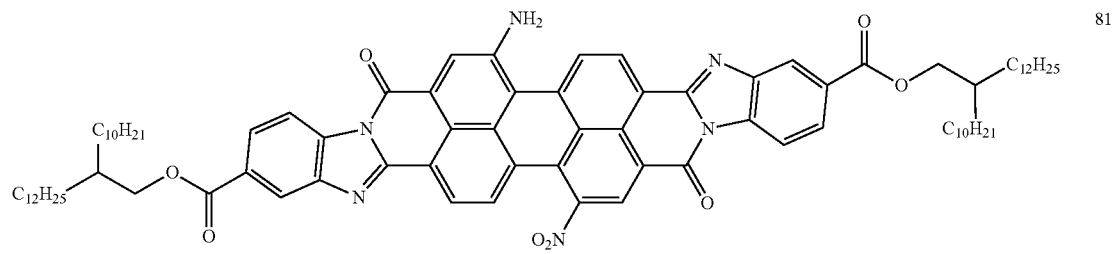
81

TABLE 6-continued
Examples of the fragment comprising the aromatic polycyclic conjugated molecule
(Core1)
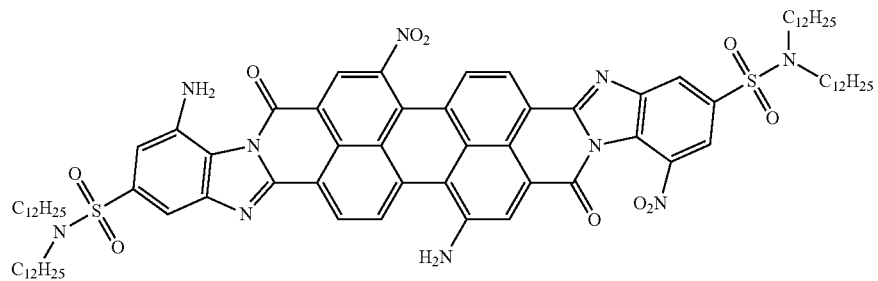
82
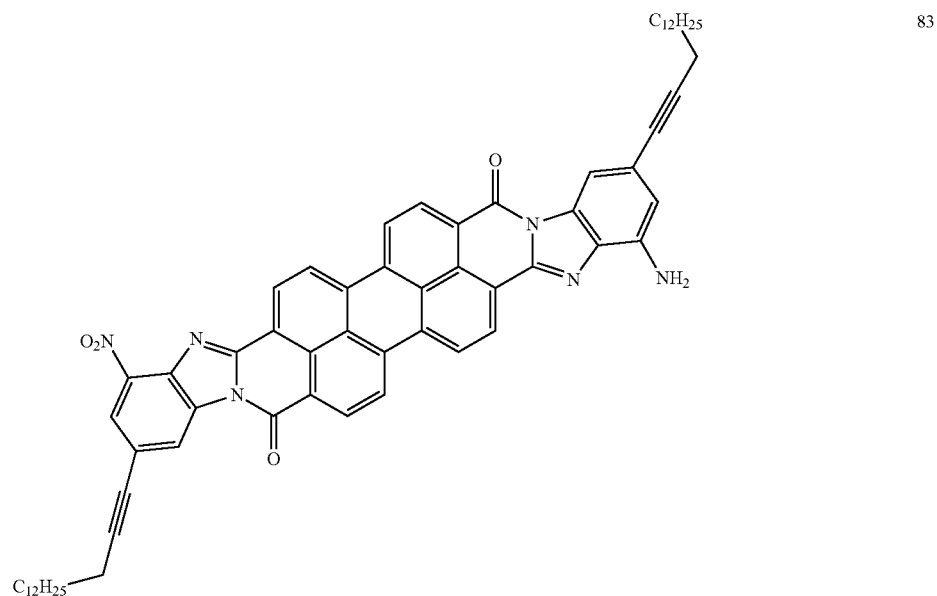
83
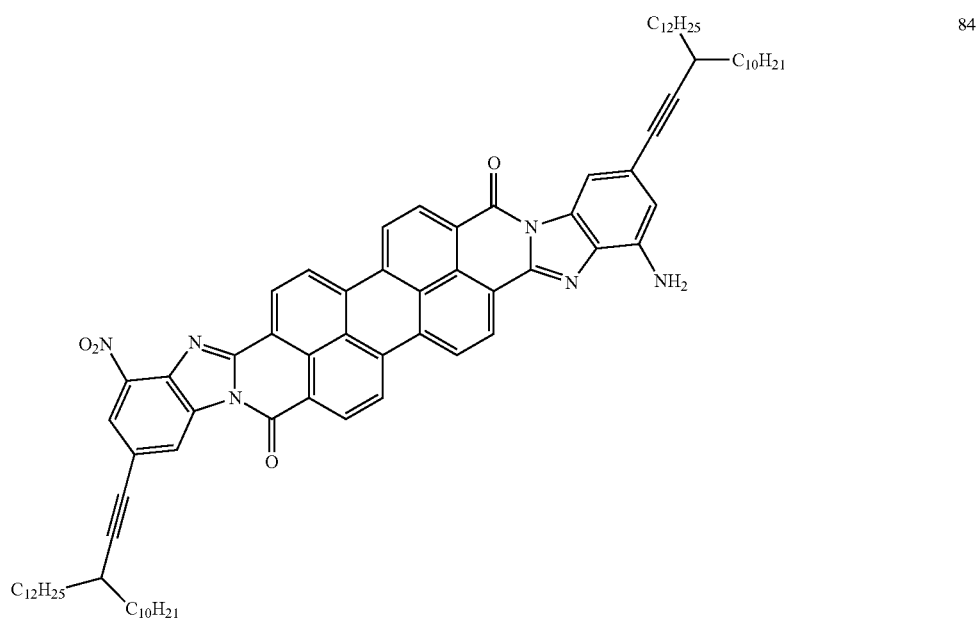
84

TABLE 6-continued
Examples of the fragment comprising the aromatic polycyclic conjugated molecule
(Core1)
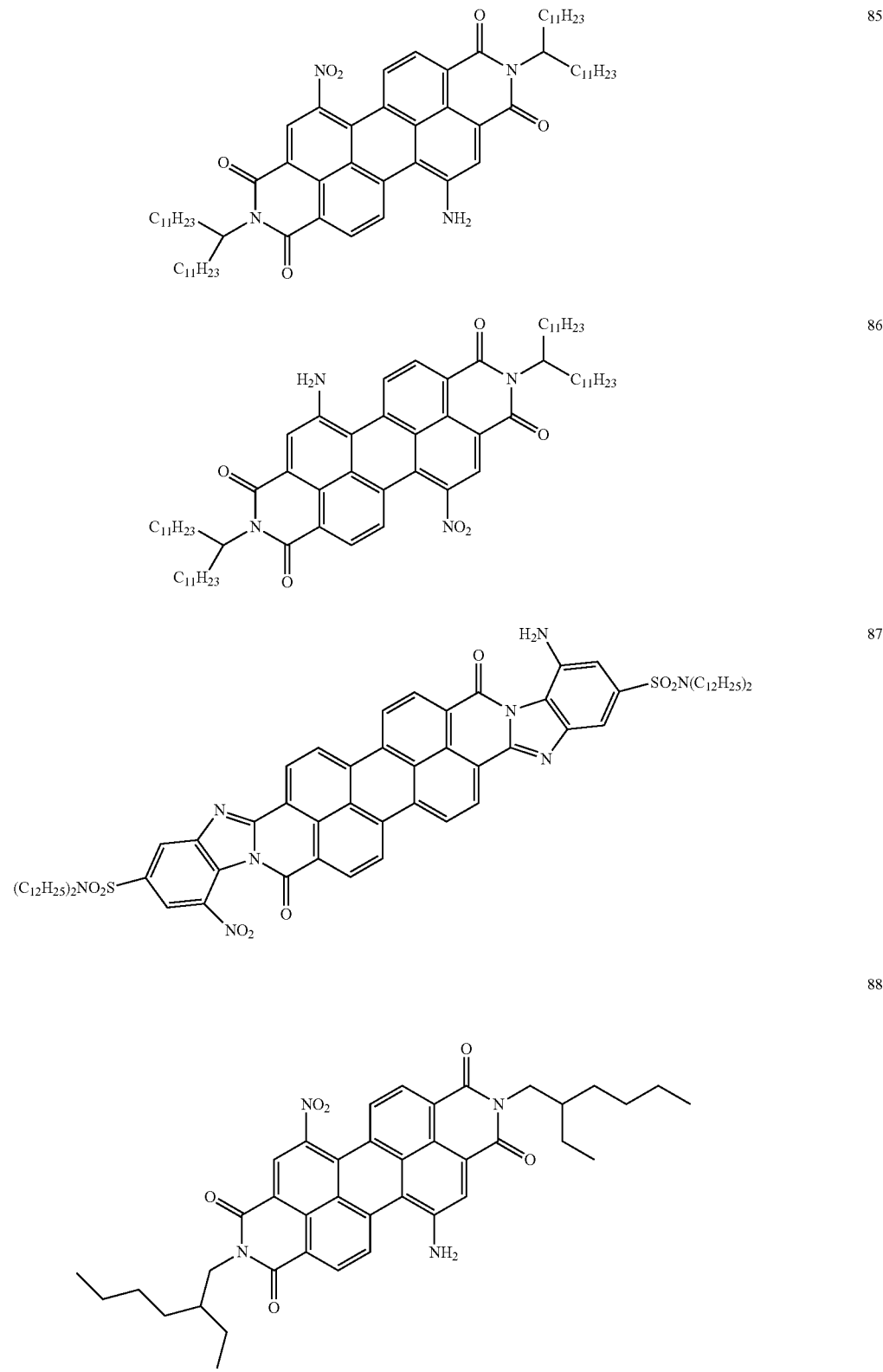

TABLE 6-continued
Examples of the fragment comprising the aromatic polycyclic conjugated molecule
(Core1)
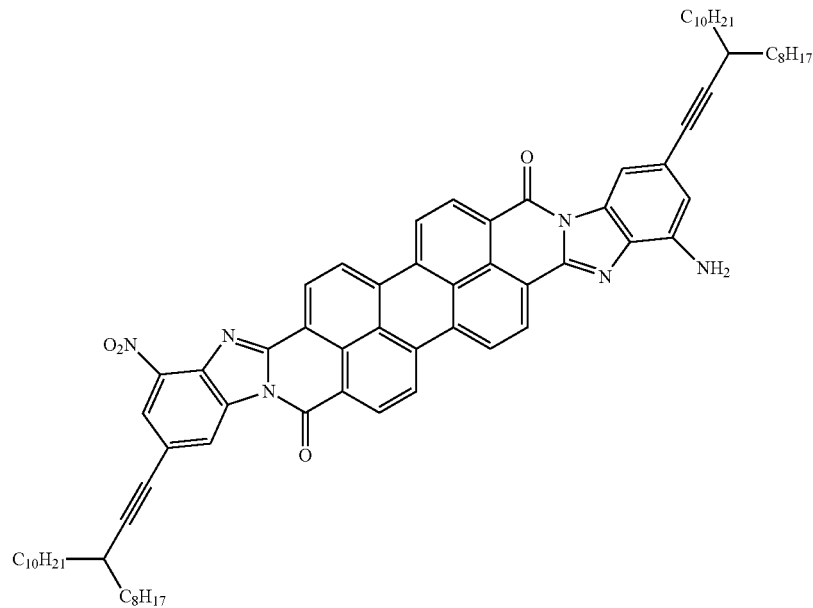
89
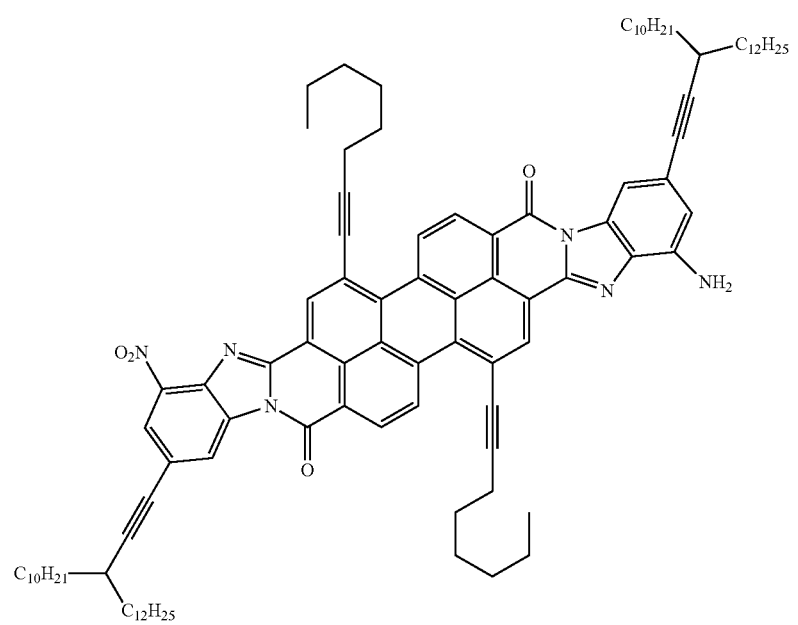
90

TABLE 6-continued
Examples of the fragment comprising the aromatic polycyclic conjugated molecule
(Core1)
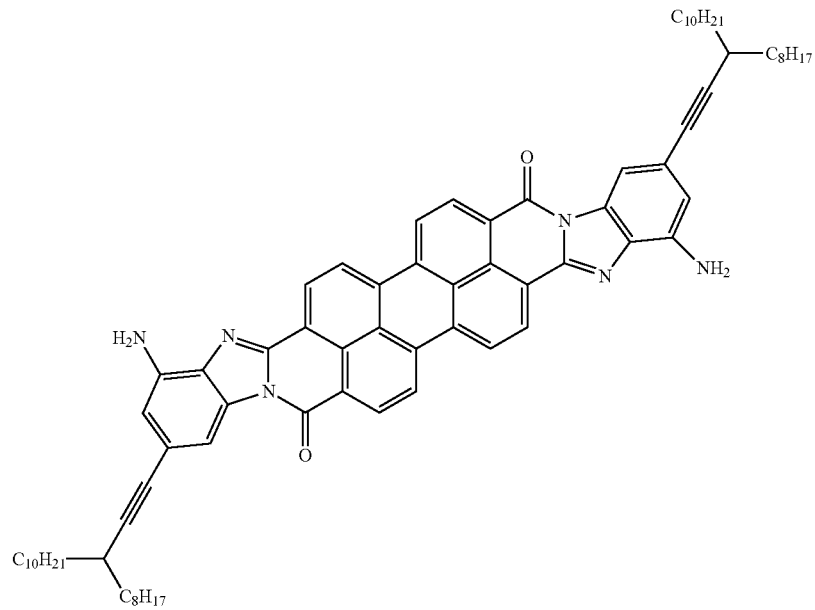
91
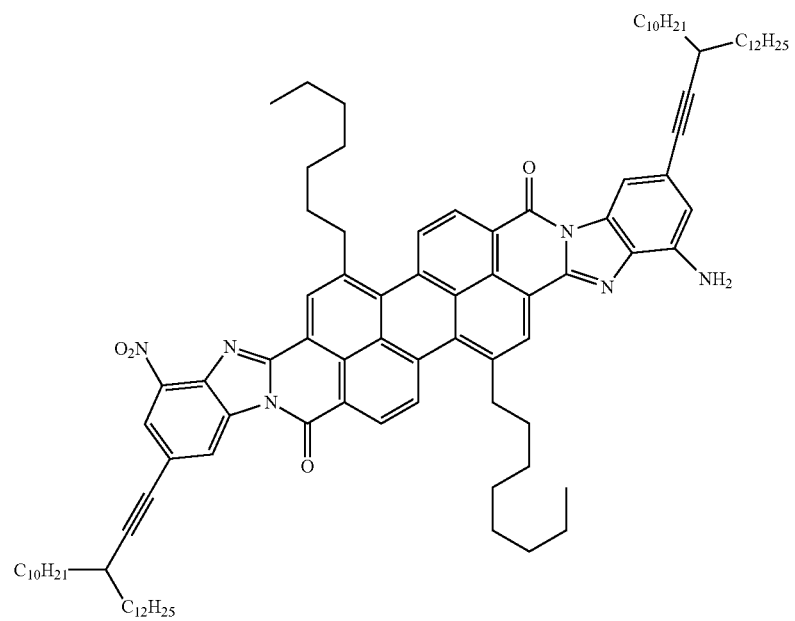
92
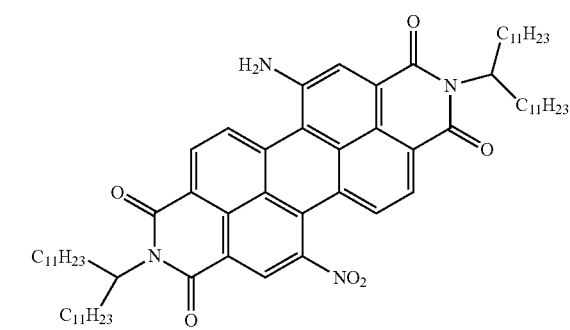
93

TABLE 6-continued
Examples of the fragment comprising the aromatic polycyclic conjugated molecule
(Core1)
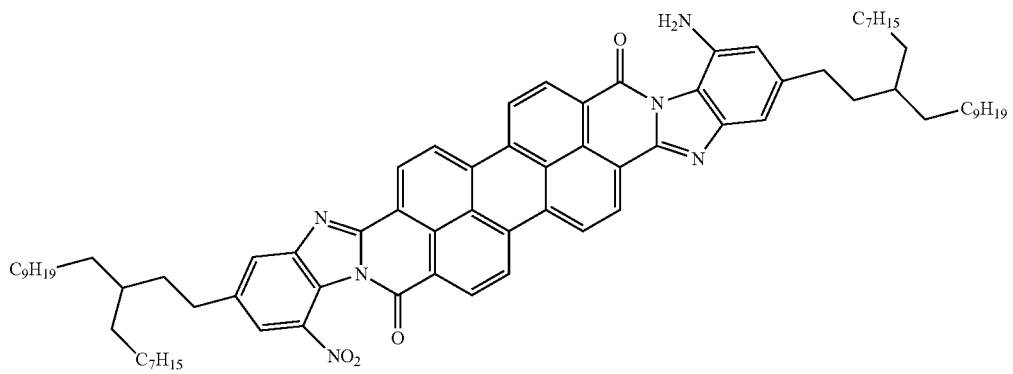
94
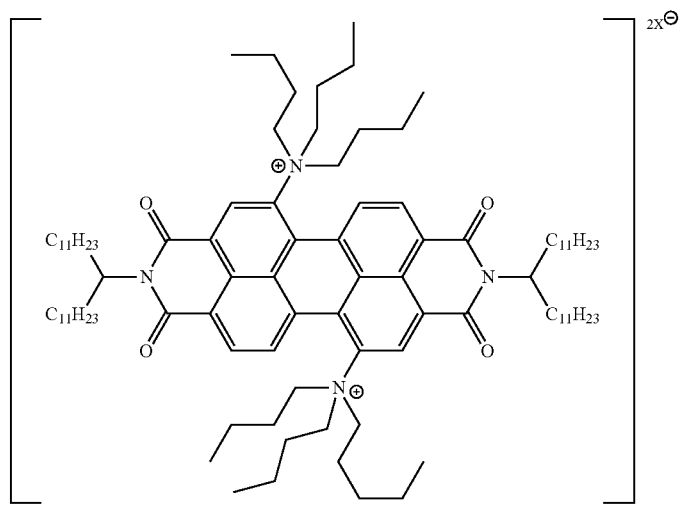
95
One ionic group should be anionic (SO3—, COOH, etc)
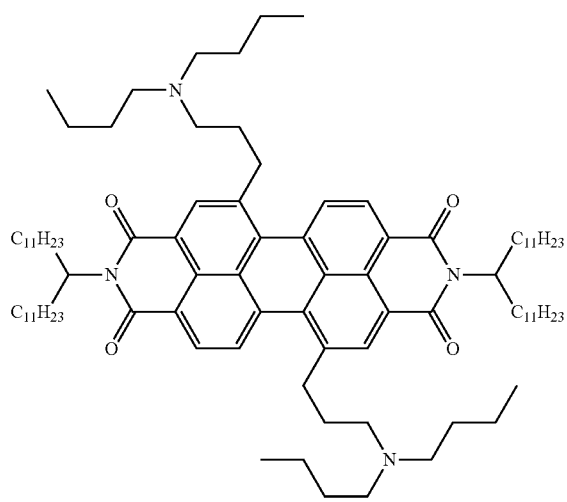
96

TABLE 6-continued

Examples of the fragment comprising the aromatic polycyclic conjugated molecule (Core1)

| 1 donor and 1 acceptor group | 97 |

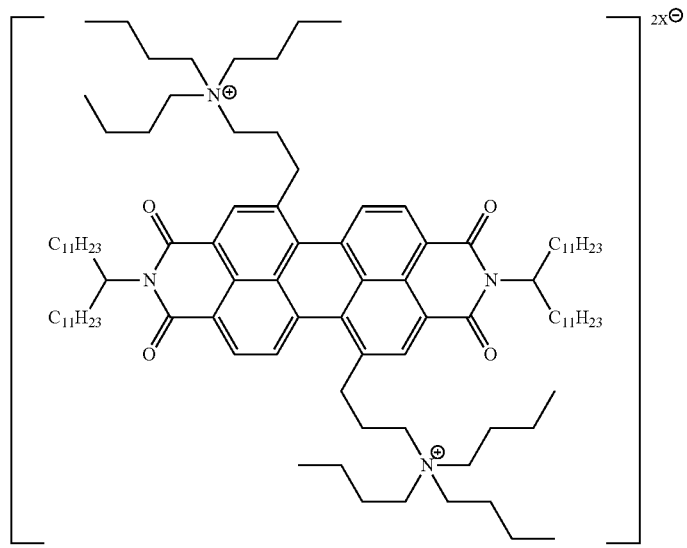

In yet another embodiment of the electro-polarizable compound, a fragment comprising the electro-conductive oligomer (Core2), resistive substituents providing solubility of the organic compound in a solvent and electrically insulating the column-like supramolecules from each other (R4) and/or the ionic groups R3 is selected from structures 98 to 107 as given in Table 7:

TABLE 7

Examples of the fragment comprising the electro-conductive oligomer (Core2)

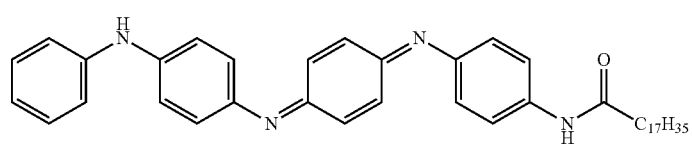

98

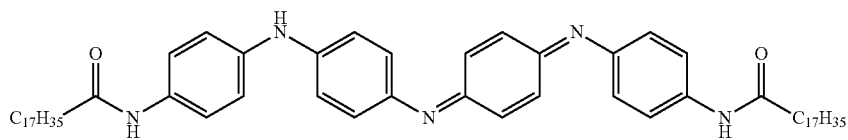

99

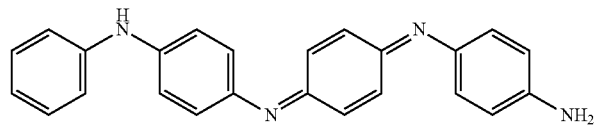

100

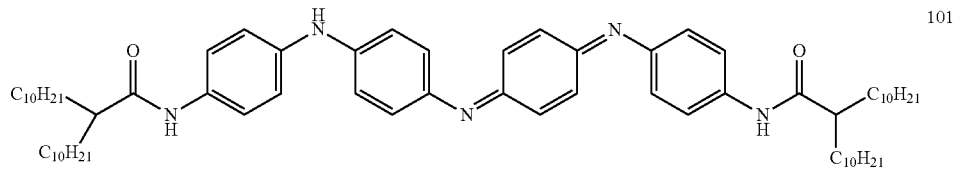

101

TABLE 7-continued

Examples of the fragment comprising the electro-conductive oligomer (Core2)

| No. | Structure |
|---|---|
| 102 | (structure shown) |
| 103 | (structure shown) |
| 104 | (structure shown) |
| 105 | (structure shown) |
| 106 | (structure shown) |
| 107 | (structure shown) |

In one embodiment of the present disclosure, a polarization ($\alpha$) of the electro-polarizable compound comprises first-order ($\alpha^{(1)}$) and second-order ($\alpha^{(2)}$) polarization according to follow formula: $\alpha = \alpha^{(1)} + \alpha^{(2)} \cdot E$, where E is an intensity of external electric field.

In one aspect, the present disclosure provides the organic solvent comprising the disclosed electro-polarizable compound. In one embodiment of the present disclose, the solution comprises a mixture of different electro-polarizable compounds. In another embodiment of the disclosed organic solvent, the mixture of the electro-polarizable compounds comprises the rylene fragments of different length. In one embodiment of disclosed organic solvent, the organic solvent is selected from the list comprising ketones, carboxylic acids, hydrocarbons, cyclic hydrocarbons, chlorohydrocarbons, alcohols, ethers, esters, and any combination thereof. In another embodiment of disclosed organic solvent, the organic solvent is selected from the list comprising acetone, xylene, toluene, ethanol, methylcyclohexane, ethyl acetate, diethyl ether, octane, chloroform, methylene chloride, dichloroethane, trichloroethene, tetrachloroethene, carbon tetrachloride, 1,4-dioxane, tetrahydrofuran, pyridine, triethylamine, nitromethane, acetonitrile, dimethylformamide, dimethyl sulfoxide, and any combination thereof. In yet another embodiment of disclose, the solution is a lyotropic liquid crystal solution.

In another aspect, the present disclosure provides a crystal metadielectric layer comprising at least one type of the disclosed electro-polarizable compounds. The crystal metadielectric layers are produced from the disclosed organic compound by the Cascade Crystallization.

Cascade Crystallization process involves a chemical modification step and four steps of ordering during the crystal metadielectric layer formation. The chemical modification step introduces hydrophilic groups on the periphery of the molecule of the disclosed organic compound in order to impart amphiphilic properties to the molecule. Amphiphilic molecules stack together into supramolecules, which is the first step of ordering. At certain concentration, supramolecules are converted into a liquid-crystalline state to form a lyotropic liquid crystal, which is the second step of ordering. The lyotropic liquid crystal is deposited under the action of a shear force (or meniscus force) onto a substrate based on a Mayer Rod shearing technique, so that shear force (or the meniscus) direction determines the crystal axis direction in the resulting solid crystal layer. The external alignment upon the lyotropic liquid crystal can be produced using any other means, for example by applying an external electric field at normal or elevated temperature, with or without additional illumination, magnetic field, or optical field (e.g., coherent photovoltaic effect); the degree of the external alignment should be sufficient to impart necessary orientation to the supramolecules of the lyotropic liquid crystal and form a structure, which serves as a base of the crystal lattice of the crystal dielectric layer. This directional deposition is third step of ordering, representing the global ordering of the crystalline or polycrystalline structure on the substrate surface. The last fourth step of the Cascade Crystallization process is drying/crystallization, which converts the lyotropic liquid crystal into a solid crystal dielectric layer. The term Cascade Crystallization process is used to refer to the chemical modification and four ordering steps as a combination process.

The Cascade Crystallization process is used for production of thin crystalline metadielectric layers. The dielectric layer produced by the Cascade Crystallization process has a global order which means that a direction of the crystallographic axis of the layer over the entire substrate surface is controlled by the deposition process. Molecules of the deposited material are packed into supramolecules with a limited freedom of diffusion or motion. The thin crystalline dielectric layer is characterized by an interplanar spacing of 3.4±0.3 Ångströms (Å) in the direction of one of the optical axes.

In one embodiment of the present disclosure, the crystal metadielectric layer comprises the column-like supramolecules formed by the electro-polarizable compounds comprising the rylene fragments of different length. The variety of the rylene fragment lengths increases the randomness of the stack. In one embodiment of the present disclosure, the layer's relative permittivity is greater than or equal to 1000. In another embodiment of the present disclosure, the polarization (P) of the crystal metadielectric layer comprises first-order ($\varepsilon_{(1)}$) and second-order ($\varepsilon_{(2)}$) and third order ($\varepsilon_{(3)}$) permittivities according to the following formula:

$$P=\varepsilon_0(\varepsilon_1-1)E+\varepsilon_0\varepsilon_2E^2+\varepsilon_0\varepsilon_3E^3+\ldots$$

where P is the polarization of the material, which also can be represented by the following formula:

$$P=NP_{induced}$$

where $P_{induced}$ is the induced polarization which can be expressed by the formula:

$$P_{induced}=\alpha E_{loc}+\beta E_{loc}^2+\gamma E_{loc}^3+\ldots$$

where $E_{loc}$ is the localized field and is expressed by the formula:

$$E_{loc}=E+P/(3\varepsilon_0)$$

The real part of the relative permittivity (ε') as can be seen from the above equations, also comprises first, second, and third order permittivities. Further, permittivity of a capacitor is a function of applied voltage and thickness of the capacitor's dielectric (d). Where voltage is the DC-voltage which is applied to the crystal metadielectric layer, and d is the layer thickness. In another embodiment of the present invention, the layer's resistivity is greater than or equal to $10^{13}$ ohm/cm.

The present disclosure provides the meta-capacitor comprising two metal electrodes positioned parallel to each other and which can be rolled or flat and planar and metadielectric layer between said electrodes. The layer comprises the electro-polarizable compounds as disclosed above.

The meta-capacitor comprises a first electrode 1, a second electrode 2, and a metadielectric layer 3 disposed between said first and second electrodes as shown in FIG. 1A. The electrodes 1 and 2 may be made of a metal, such as copper, zinc, or aluminum or other conductive material such as graphite or carbon nanomaterials and are generally planar in shape.

The electrodes 1, 2 may be flat and planar and positioned parallel to each other. Alternatively, the electrodes may be planar and parallel, but not necessarily flat, they may be coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes 1 and 2 may range from about 100 nm to about 10 000 μm. The maximum voltage $V_{bd}$ between the electrodes 1 and 2 is approximately the product of the breakdown field $E_{bd}$ and the electrode spacing d. If $E_{bd}$=0.1 V/nm and the spacing d between the electrodes 1 and 2 is 10,000 microns (100,000 nm), the maximum voltage $V_{bd}$ would be 100,000 volts.

The electrodes 1 and 2 may have the same shape as each other, the same dimensions, and the same area A. By way of example, and not by way of limitation, the area A of each electrode 1 and 2 may range from about 0.01 m$^2$ to about 1000 m$^2$. By way of example and not by way of limitation for rolled capacitors, electrodes up to, e.g., 1000 m long and 1 m wide.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor may be approximated by the formula:

$$C=\varepsilon\varepsilon_0 A/d \qquad (V)$$

where $\varepsilon_0$ is the permittivity of free space (8.85×10$^{-12}$ Coulombs$^2$/(Newton·meter$^2$)) and ε is the dielectric constant of the dielectric layer. The energy storage capacity U of the capacitor may be approximated as:

$$U=\tfrac{1}{2}\varepsilon\varepsilon_0 AE_{bd}^2 \qquad (VI)$$

The energy storage capacity U is determined by the dielectric constant E, the area A, and the breakdown field $E_{bd}$. By appropriate engineering, a capacitor or capacitor bank may be designed to have any desired energy storage capacity U. By way of example, and not by way of limitation, given the above ranges for the dielectric constant ε, electrode area A, and breakdown field $E_{bd}$ a capacitor in accordance with aspects of the present disclosure may have an energy storage capacity U ranging from about 500 Joules to about 2·10$^{16}$ Joules.

For a dielectric constant E ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 W·h/kg up to about 100,000 W·h/kg, though implementations are not so limited.

Figure 1B:
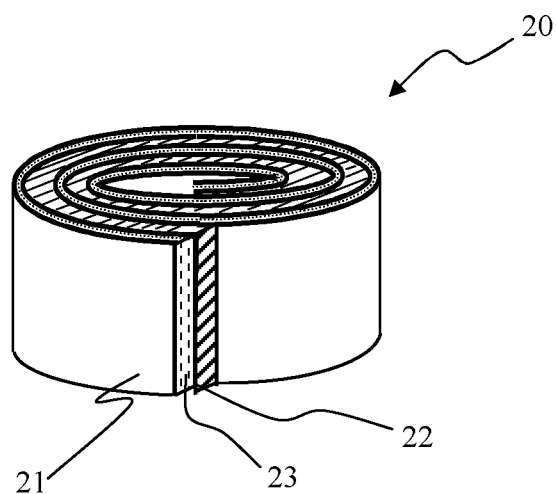
FIG. 1B schematically shows a capacitor with rolled (circular) electrodes in accordance with another aspect of the present disclosure.

The present disclosure includes meta-capacitors that are coiled, e.g., as depicted in FIG. 1B. In this example, a meta-capacitor 20 comprises a first electrode 21, a second electrode 22, and a metadielectric material layer 23 of the type described hereinabove disposed between said first and second electrodes. The electrodes 21 and 22 may be made of a metal, such as copper, zinc, or aluminum or other conductive material such as graphite or carbon nanomaterials and are generally planar in shape. In one implementation, the electrodes and metadielectric material layer 23 are in the form of long strips of material that are sandwiched together and wound into a coil along with an insulating material, e.g., a plastic film such as polypropylene or polyester to prevent electrical shorting between the electrodes 21 and 22.

In order that the invention may be more readily understood, reference is made to the following examples, which are intended to be illustrative of the invention, but are not intended to limit the scope.

Example 1

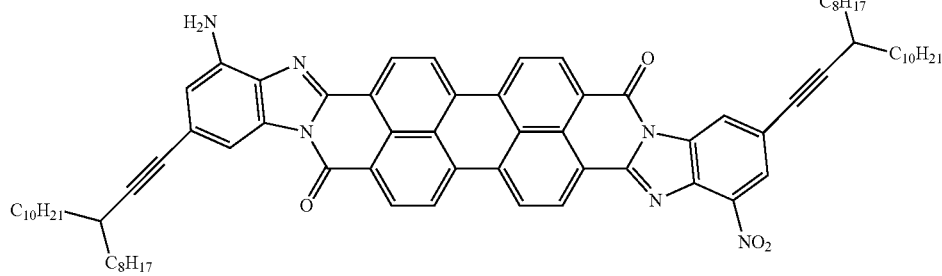

Procedure:

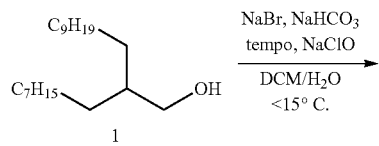

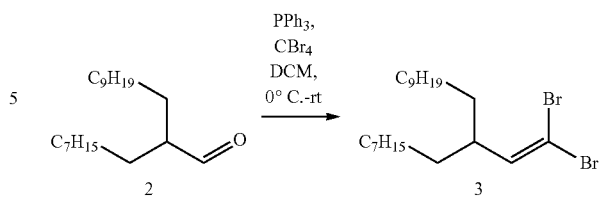

To DCM (500 mL) was added PPh$_3$ (154.0 g, 587 mmol, 4 equiv.) under N$_2$ atmosphere. To the suspension was added CBr$_4$ (97.3 g, 294 mmol, 2 equiv.) at 0° C. The mixture was stirred for 15 min at 0° C. and 20 min at room temperature. Freshly made compound 2 (51.4 g, 146 mmol, 1.0 equiv.) in

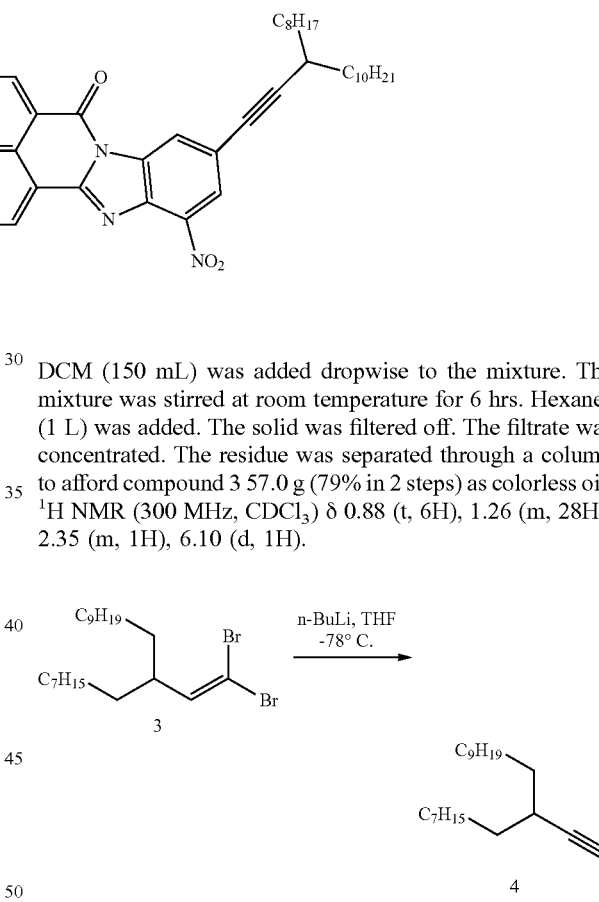

DCM (150 mL) was added dropwise to the mixture. The mixture was stirred at room temperature for 6 hrs. Hexanes (1 L) was added. The solid was filtered off. The filtrate was concentrated. The residue was separated through a column to afford compound 3 57.0 g (79% in 2 steps) as colorless oil. $^1$H NMR (300 MHz, CDCl$_3$) δ 0.88 (t, 6H), 1.26 (m, 28H), 2.35 (m, 1H), 6.10 (d, 1H).

To H$_2$O (10.0 mL) was added NaHCO$_3$ (1.7 g, 20.2 mmol, 30 g/mol equiv.) and NaBr (280.0 mg, 2.7 mmol, 5 g/mol equiv.). The mixture was stirred to form a clear solution. Compound 1 (20 g, 56.4 mmol, 1 equiv.) in Dichloromethane (DCM) (70 mL) and tempo (340.0 mg, 0.6 g/mol) were added to the clear solution. The two-phase mixture was cooled down to 10° C. using an ice bath. The NaClO solution (70.5 mL, 0.8 N, 1 equiv.) was added dropwise with vigorous stirring. After the NaClO solution was added, the mixture was removed from the ice bath and stirred at room temperature for 30 min. The DCM phase was collected, extracted with DCM (25 mL×2), combined with organic phase, washed with water and brine, dried over MgSO$_4$, and was concentrated to give compound 2 18 g (90%) as a colorless oil. $^1$H NMR (300 MHz, CDCl$_3$) not available.

To anhydrous Tetrahydrofuran (THF) (250 mL) was added compound 3 (57.0 g, 115 mmol, 1 equiv.). The mixture was cooled down to −78° C. under N$_2$-atmosphere. n-BuLi (138 mL, 2.5 M, 3 equiv.) was added dropwise to the mixture. The mixture was stirred for 2 hours, then was quenched with water (200 mL). The organic phase was collected. The water phase was extracted with EA (50 mL×2). The organic phases were combined, washed with water and brine, dried over MgSO$_4$ and concentrated to afford crude compound 4 37.1 g (100%) as colorless oil. $^1$H NMR (300 MHz, CDCl$_3$) δ 0.88 (t, 6H), 1.26 (m, 28H), 2.30 (m, 1H), 2.03 (s, 1H).

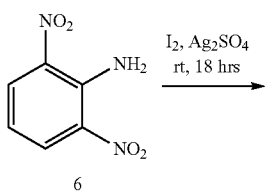

To EtOH (40.0 mL) was added compound 6 (4.2 g, 23.0 mmol, 1.0 equiv.), AgSO₄ (10.0 g, 32.1 mmol, 1.4 equiv.) and I₂ (8.2 g, 32.1 mmol, 1.4 equiv.). The mixture was stirred at room temperature for 18 hrs. Solid material was filtered off and washed with ethyl acetate (EA), and the filtrate was concentrated. The residue was separated through a column to afford compound 7 5.4 g (77%) as a dark yellow solid. $^1$H NMR (300 MHz, CDCl₃) not available.

Scale up: To Ethanol (EtOH) (1000.0 mL) was added compound 6 (100.0 g, 547.6 mmol, 1.0 equiv.), AgSO₄ (238.0 g, 764.3 mmol, 1.4 equiv.) and I₂ (195.2 g, 764.3 mmol, 1.4 equiv.). The mixture was stirred at room temperature for 18 hrs. Solid material was filtered off and washed with EA (200 mL×2). The filtrate was concentrated until ⅓ of the filtrate volume remained. The solid was filtered and washed by cold EtOH (100 mL×2) to provide compound 7 43 g as dark yellow solid with less than 5% starting material 6 inside. The filtrate was concentrated and the above described procedure was repeated with 0.7 equiv. of AgSO₄ and I₂. The same working up process was applied to resulting second batch of compound 7 30 g as dark yellow solid with less than 5% starting material 6 inside. The solids were combined to afford compound 7 73 g (43.4%). $^1$H NMR (300 MHz, CDCl₃) not available. Reaction was tracked by TLC.

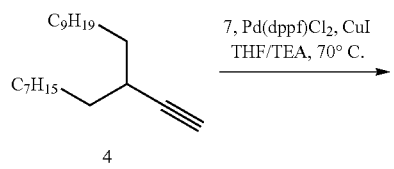

To anhydrous THF (10.0 mL) and tri-ethyl amine (10.0 mL) was added compound 4 (7.4 g, 21.2 mmol, 1.2 equiv.), compound 7 (5.2 g, 16.7 mmol, 1.0 equiv.), Pd(dppf)Cl₂ (0.05 g, 0.08 mmol, 0.02 equiv.), CuI (0.02 g, 0.1 mmol, 0.04 equiv.). The mixture was degassed under vacuum and purged with N₂ three times. The reaction was stirred at 70° C. for 8.0 hours. The mixture was cooled down to room temperature and EA (10 mL) was added to dilute. The solid was filtered off and the filtrate was concentrated, then separated with a column to afford compound 5 7.5 g (84%) as a yellow solid. $^1$H NMR (300 MHz, CDCl₃)) δ 7.99 (s, 2H), 2.45 (m, 1H), 1.26-1.55 (m, 40H), 0.87 (t, 6H).

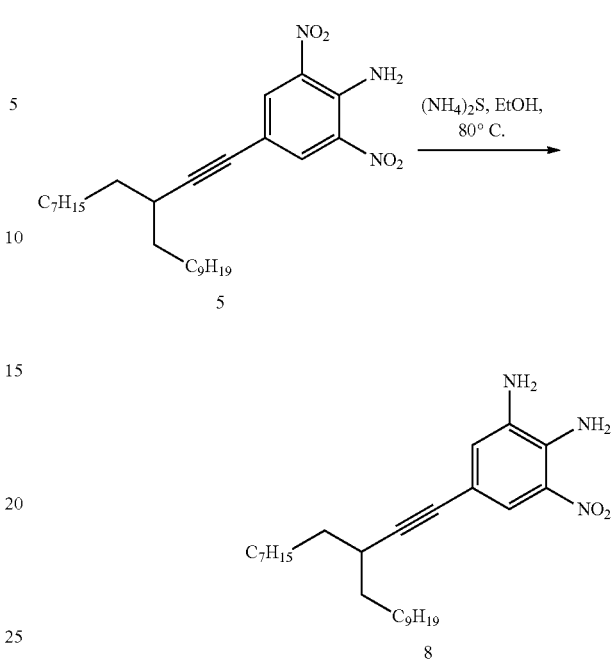

To EtOH (20.0 mL) was added compound 5 (7.5 g, 14.1 mmol, 1.0 equiv.) and ammonium sulfide (8.6 g 20% water solution, 28.2 mmol, 2.0 equiv.). The mixture was stirred at 80° C. for 1 hour. 2.0 equivalents of ammonium sulfide were added again. The mixture was stirred at 80° C. for an additional 1 hour. The mixture was concentrated, diluted with EA, and washed with water and brine. The organic phase was collected, concentrated and separated through a column to give product 8 6.1 g (87%) as a dark red solid. $^1$H NMR (300 MHz, CDCl₃) δ 7.81 (s, 1H), 6.94 (s, 1H), 2.45 (m, 1H), 1.26-1.46 (m, 40H), 0.87 (t, 6H).

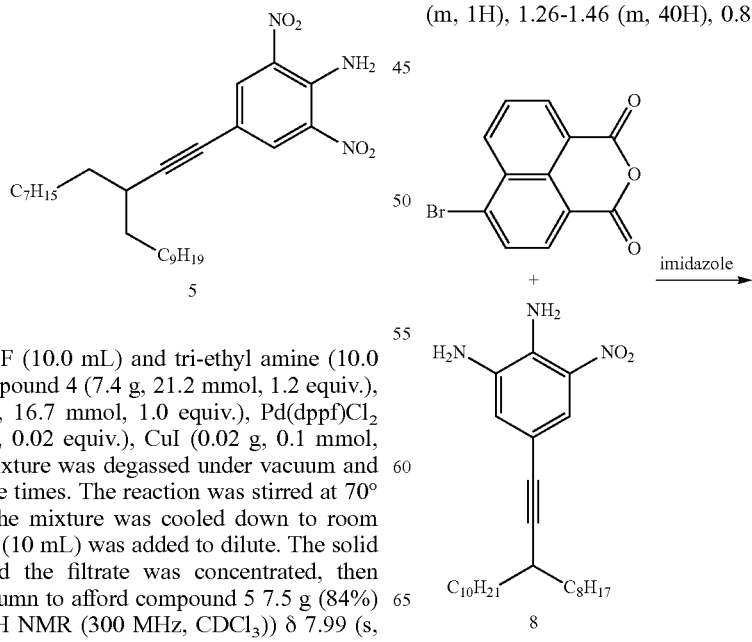

-continued

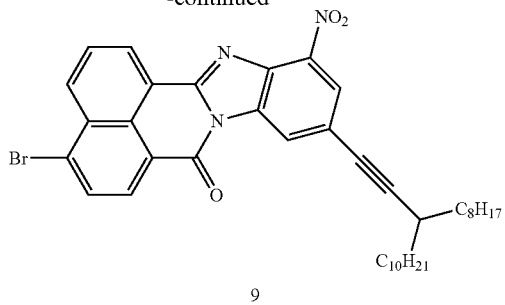

9

To a 25 mL flask was added compound 8 (1 equiv.), 4-bromo-1,8-naphthalic anhydride (1 equiv.) and imidazole (70 equiv.). The mixture was degassed under vacuum and purged with N$_2$ three times. The reaction was stirred at 130° C. for 3 hours and 180° C. for 12 more hours. The dark purple mixture was cooled down. The solid was washed with water (3×60 mL) and EtOH (3×60 mL), and vacuum dried to give 9.

To EtOH (20.0 mL) was added compound 9 (1.0 equiv.) and ammonium sulfide (2.0 equiv.). The mixture was stirred at 80° C. for 1 hour. 2.0 equivalents of ammonium sulfide were added again. The mixture was stirred at 80° C. for an additional 1 hour. The mixture was concentrated, diluted with EA, washed with water and brine, and dried to give 10.

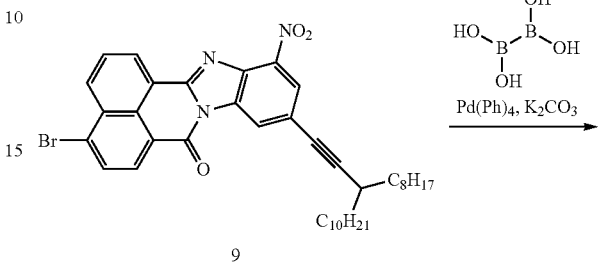

9

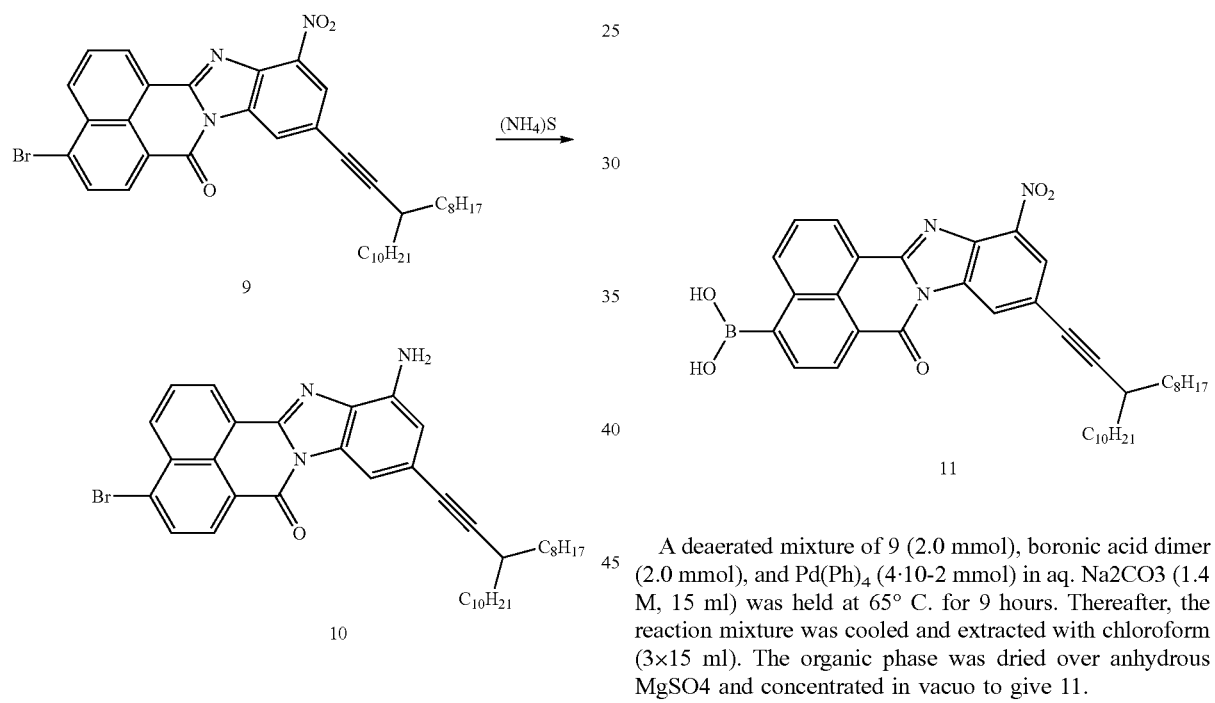

A deaerated mixture of 9 (2.0 mmol), boronic acid dimer (2.0 mmol), and Pd(Ph)$_4$ (4·10-2 mmol) in aq. Na2CO3 (1.4 M, 15 ml) was held at 65° C. for 9 hours. Thereafter, the reaction mixture was cooled and extracted with chloroform (3×15 ml). The organic phase was dried over anhydrous MgSO4 and concentrated in vacuo to give 11.

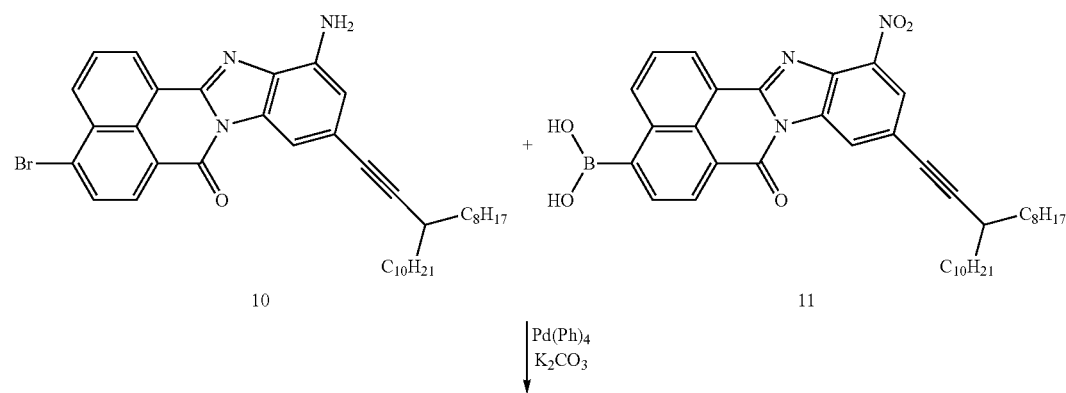

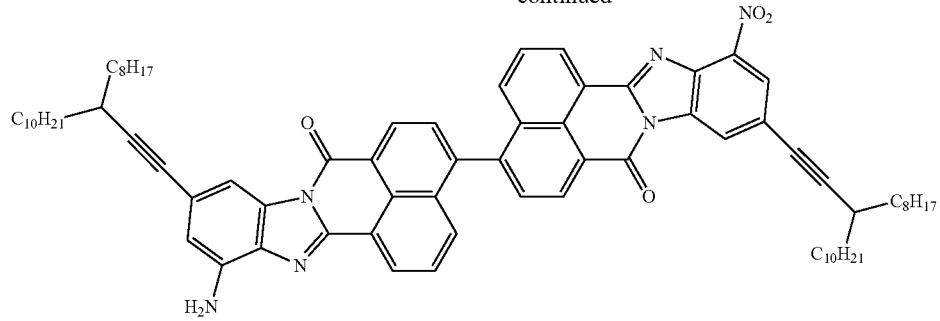

12

A deaerated mixture of 10 (2.0 mmol), 11 (2.0 mmol), and Pd(Ph)$_4$ (4·10-2 mmol) in aq. Na2CO3 (1.4 M, 15 ml) was held at 65° C. for 9 hours. Thereafter, the reaction mixture was cooled and extracted with chloroform (3×15 ml). The organic phase was dried over anhydrous MgSO4 and concentrated in vacuo to give 12.

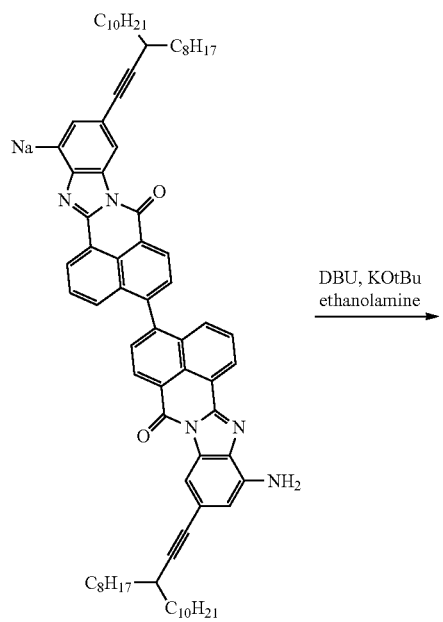

DBU, KOtBu
ethanolamine
→

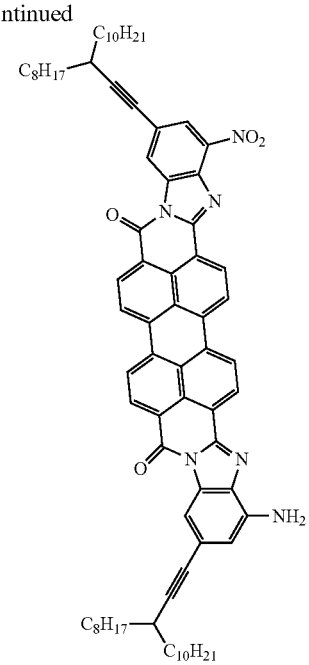

A mixture of 1.48 g (13 mmol) potassium tert-butoxide 2.30 g (15.1 mmol) of diazabicyclo[5.4.0]undec-7-ene (DBU), 2.2 g 36.3 mmol) ethanolamine and 1.0 g of 12 was heated to 140° C. for 11 hours. Afterwards, the same amount of potassium tert-butylat, DBU and ethanolamine were added and the mixture was kept at 140° C. for 18 hours. The reaction mixture was cooled to room temperature, poured into 250 ml of 1M HCl filtered, washed until neutral pH and then dried to give the final product.

Example 2

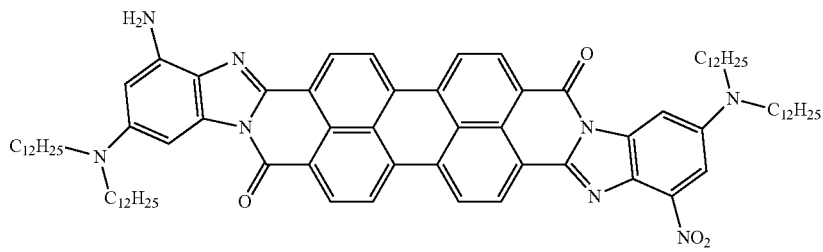

Procedure:

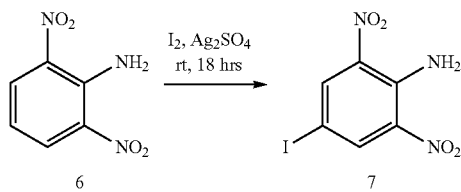

To EtOH (40.0 mL) was added compound 6 (4.2 g, 23.0 mmol, 1.0 equiv.), AgSO₄ (10.0 g, 32.1 mmol, 1.4 equiv.) and I₂ (8.2 g, 32.1 mmol, 1.4 equiv.). The mixture was stirred at room temperature for 18 hrs. The solid was filtered off and washed with EA. The filtrate was concentrated. The residue was separated through a column to afford compound 7 5.4 g (77%) as a dark yellow solid. ¹H NMR (300 MHz, CDCl₃) not available.

Scale up: To EtOH (1000.0 mL) was added compound 6 (100.0 g, 547.6 mmol, 1.0 equiv.), AgSO₄ (238.0 g, 764.3 mmol, 1.4 equiv.) and I₂ (195.2 g, 764.3 mmol, 1.4 equiv.). The mixture was stirred at room temperature for 18 hours. The solid was filtered off and washed with EA (200 mL×2). The filtrate was concentrated until ⅓ of the filtrate volume remained. The solid was filtered and washed by cold EtOH (100 mL×2) to provide compound 7 43 g as dark yellow solid with less than 5% starting material 6 inside. The filtrate was concentrated and the above-described procedure was repeated with 0.7 equiv. of AgSO₄ and I₂. The same working up process was applied to provided second batch of compound 7 30 g as dark yellow solid with less than 5% starting material 6 inside. The solids were combined to afford compound 7 73 g (43.4%). ¹H NMR (300 MHz, CDCl₃) not available. Reaction was tracked by TLC.

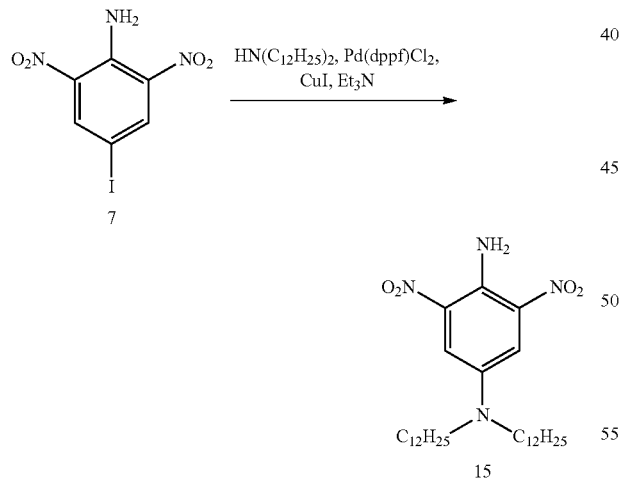

To anhydrous THF (10.0 mL) and TEA (10.0 mL) was added compound didodecylamine (1.2 equiv.), compound 7 (1.0 equiv.), Pd(dppf)Cl₂ (0.02 equiv.), CuI (0.04 equiv.). The mixture was degassed under vacuum and purged with N₂ three times. The reaction was stirred at 70° C. for 8.0 hrs. The mixture was cooled down and EA (10 mL) was added to dilute. The solid was filtered off and the filtrate was concentrated, then separated with a column to afford compound 15.

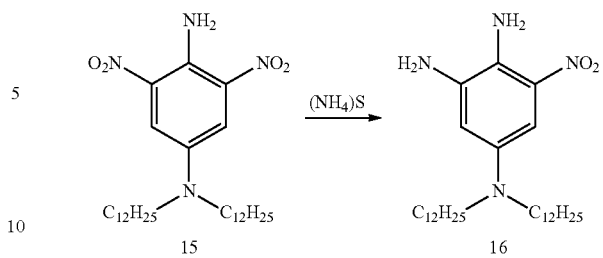

To EtOH (20.0 mL) was added compound 15 (7.5 g, 14.1 mmol, 1.0 equiv.) and ammonium sulfide (8.6 g 20% water solution, 28.2 mmol, 2.0 equiv.). The mixture was stirred at 80° C. for 1 hour. 2.0 equivalents of ammonium sulfide were added again. The mixture was stirred 80° C. for an additional 1 hour. The mixture was concentrated, diluted with EA, washed with water and brine. The organic phase was collected, concentrated and separated through a column to give product 16.

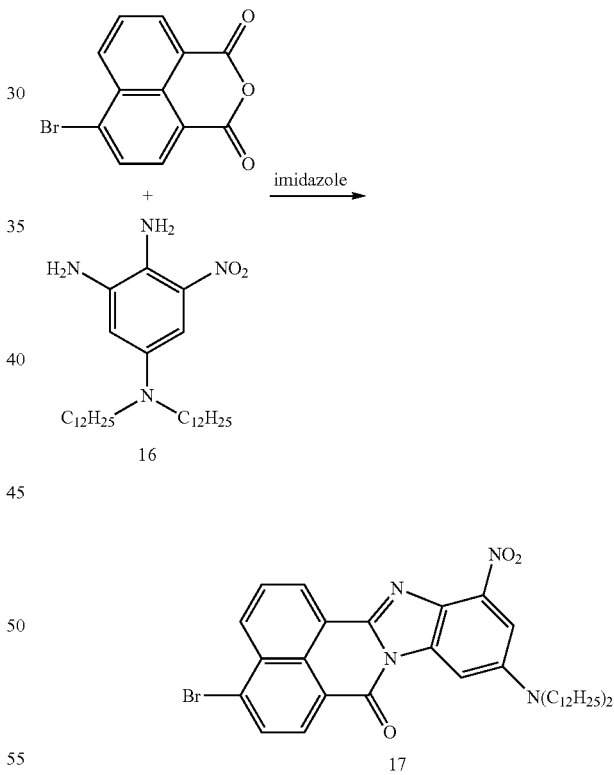

To a 25 mL flask was added compound 16 (1 equiv.), 4-bromo-1,8-naphthalic anhydride (1 equiv.) and imidazole (70 equiv.). The mixture was degassed under vacuum and purged with N₂ three times. The reaction was stirred at 130° C. for 3 hours and 180° C. for 12 more hours. The dark purple mixture was cooled down. The solid was washed with water (3×60 mL) and EtOH (3×60 mL), and vacuum dried to give 17.

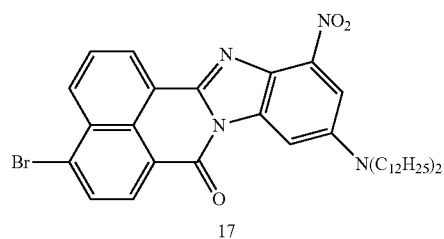

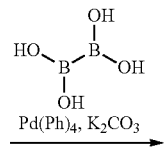

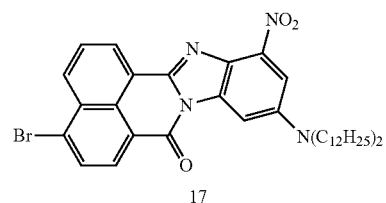

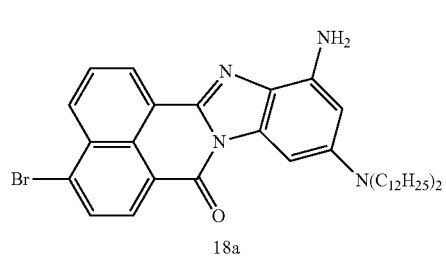

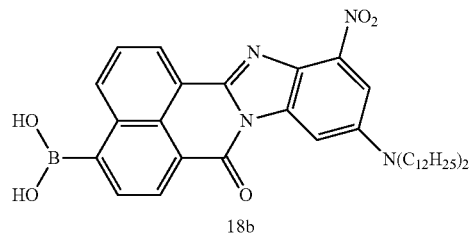

To EtOH (20.0 mL) was added compound 17 (1.0 equiv.) and ammonium sulfide (2.0 equiv.). The mixture was stirred at 80° C. for 1 hour. Refilled 2.0 equiv. ammonium sulfide. The mixture was stirred at 80° C. for an additional 1 hour. The mixture was concentrated, diluted with EA, washed with water and brine, and dried to give 18a.

A deaerated mixture of 17 (2.0 mmol), boronic acid dimer (2.0 mmol), and Pd(Ph)$_4$ (4·10-2 mmol) in aq. Na2CO3 (1.4 M, 15 ml) was held at 65° C. for 9 hours. Thereafter, the reaction mixture was cooled and extracted with chloroform (3×15 ml). The organic phase was dried over anhydrous MgSO4 and concentrated in vacuo to give 18b.

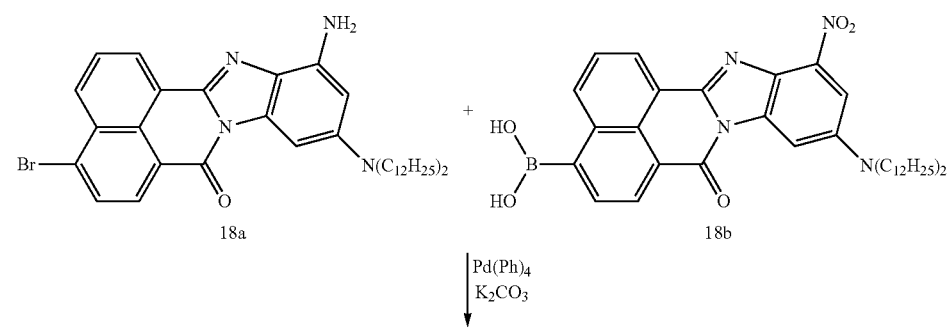

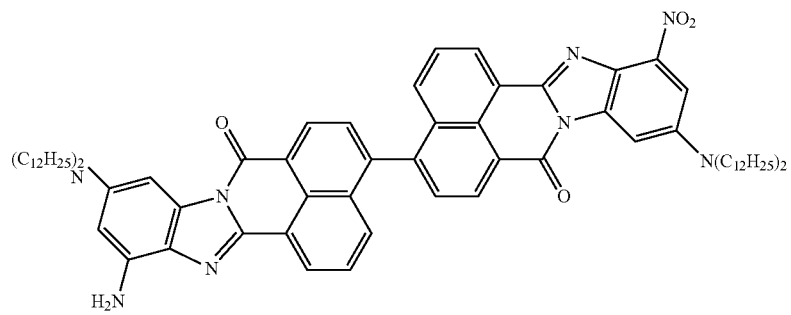

A deaerated mixture of 18a (2.0 mmol), 18b (2.0 mmol), and Pd(Ph)$_4$ (4·10-2 mmol) in aq. Na2CO3 (1.4 M, 15 ml) was held at 65° C. for 9 hours. Thereafter, the reaction mixture was cooled and extracted with chloroform (3×15 ml). The organic phase was dried over anhydrous MgSO4 and concentrated in vacuo to give 19.

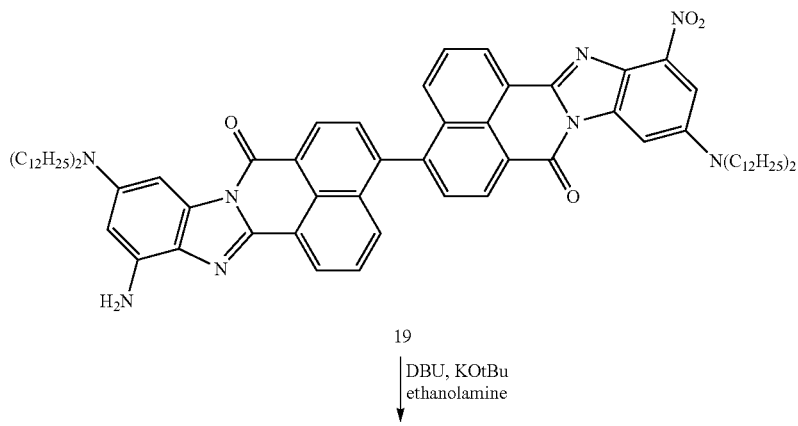

19

DBU, KOtBu
ethanolamine

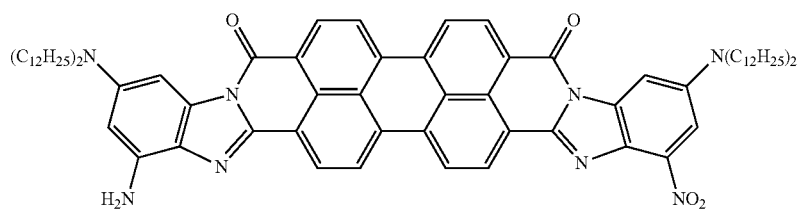

A mixture of 1.48 g (13 mmol) potassium tert-butoxide 2.30 g (15.1 mmol) of diazabicyclo[5.4.0]undec-7-ene (DBU), 2.2 g 36.3 mmol) ethanolamine and 1.0 g of 19 was heated to 140° C. for 11 hours. Afterwards, the same amount of potassium tert-butylat, DBU and ethanolamine were added and the mixture was kept at 140° C. for 18 hours. The reaction mixture was cooled to room temperature, poured into 250 ml of 1M HCl, filtered, washed until neutral pH and then dried to give the final product.

Example 3

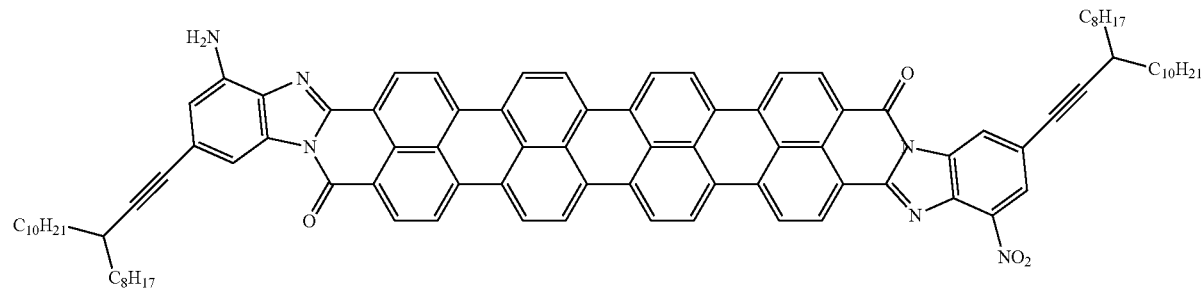

Procedure:

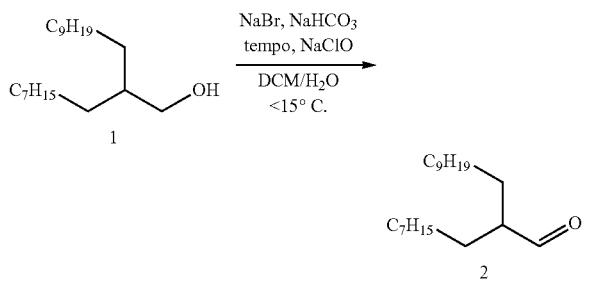

To H$_2$O (10.0 mL) was added NaHCO$_3$ (1.7 g, 20.2 mmol, 30 g/mol equiv.) and NaBr (280.0 mg, 2.7 mmol, 5 g/mol equiv.). The mixture was stirred to form a clear solution. Compound 1 (20 g, 56.4 mmol, 1 equiv.) in DCM (70 mL) and tempo (340.0 mg, 0.6 g/mol) were added to the clear solution. The two-phase mixture was cooled down to 10° C. using an ice bath. The NaClO solution (70.5 mL, 0.8 N, 1 equiv.) was added drop-wise with vigorous stirring. After addition, the NcClO mixture was removed from the ice bath and kept stirred at room temperature for 30 min. The DCM phase was collected, extracted with DCM (25 mL×2), combined with organic phase, washed with water and brine, dried over MgSO$_4$, and was concentrated to give compound 2 18 g (90%) as a colorless oil. $^1$H NMR (300 MHz, CDCl$_3$) not available.

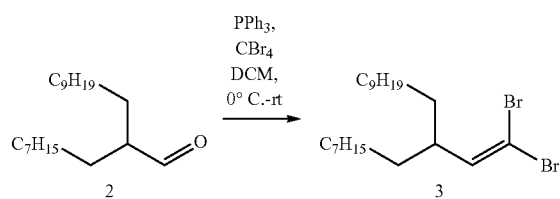

To DCM (500 mL) was added PPh$_3$ (154.0 g, 587 mmol, 4 equiv.) under N$_2$-atmosphere. To the suspension was added CBr$_4$ (97.3 g, 294 mmol, 2 equiv.) at 0° C. The mixture was stirred for 15 min at 0° C. and 20 min at rt. Freshly made compound 2 (51.4 g, 146 mmol, 1.0 equiv.) in DCM (150 mL) was added dropwise. The mixture was stirred at room temperature for 6 hrs. Hexanes (1 L) was added. The solid was filtered off. The filtrate was concentrated. The residue was separated through a column to afford compound 3 57.0 g (79% in 2 steps) as colorless oil. $^1$H NMR (300 MHz, CDCl$_3$) δ 0.88 (t, 6H), 1.26 (m, 28H), 2.35 (m, 1H), 6.10 (d, 1H).

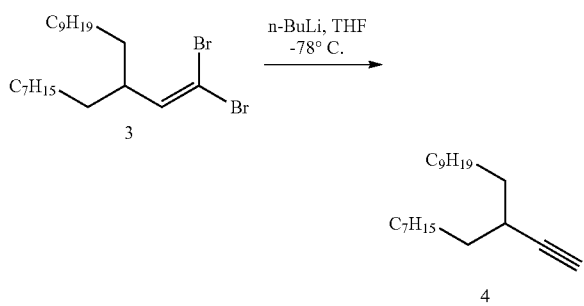

To anhydrous THF (250 mL) was added compound 3 (57.0 g, 115 mmol, 1 equiv.). The mixture was cooled down to −78° C. under N$_2$-atmosphere. n-BuLi (138 mL, 2.5 M, 3 equiv.) was added dropwise. The mixture was stirred for 2 hours, then was quenched with water (200 mL). The organic phase was collected. The water phase was extracted with EA (50 mL×2). The organic phases were combined, washed with water and brine, dried over MgSO$_4$ and concentrated to afford crude compound 4 37.1 g (100%) as colorless oil. $^1$H NMR (300 MHz, CDCl$_3$) δ 0.88 (t, 6H), 1.26 (m, 28H), 2.30 (m, 1H), 2.03 (s, 1H).

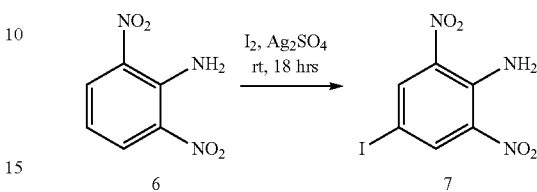

To EtOH (40.0 mL) was added compound 6 (4.2 g, 23.0 mmol, 1.0 equiv.), AgSO$_4$ (10.0 g, 32.1 mmol, 1.4 equiv.) and I$_2$ (8.2 g, 32.1 mmol, 1.4 equiv.). The mixture was stirred at room temperature for 18 hrs. Solid material was filtered and washed with EA. The filtrate was concentrated. The residue was separated through a column to afford compound 7 5.4 g (77%) as a dark yellow solid. $^1$H NMR (300 MHz, CDCl$_3$) not available.

Scale up: To EtOH (1000.0 mL) was added compound 6 (100.0 g, 547.6 mmol, 1.0 equiv.), AgSO$_4$ (238.0 g, 764.3 mmol, 1.4 equiv.) and I$_2$ (195.2 g, 764.3 mmol, 1.4 equiv.). The mixture was stirred at room temperature for 18 hrs. The solid material was filtered, washed with EA (200 mL×2). The filtrate was concentrated till ⅓ volume. The solid was filtered and washed by cold EtOH (100 mL×2) to provide compound 7 43 g as dark yellow solid with less than 5% starting material 6 inside. The filtrate was concentrated and the above-described procedure was repeated with 0.7 equivalent of AgSO$_4$ and I$_2$. The same working up process was applied to provide second batch of compound 7 30 g as dark yellow solid with less than 5% starting material 6 inside. The solids were combined to afford compound 7 73 g (43.4%). $^1$H NMR (300 MHz, CDCl$_3$) not available. Reaction was tracked by TLC.

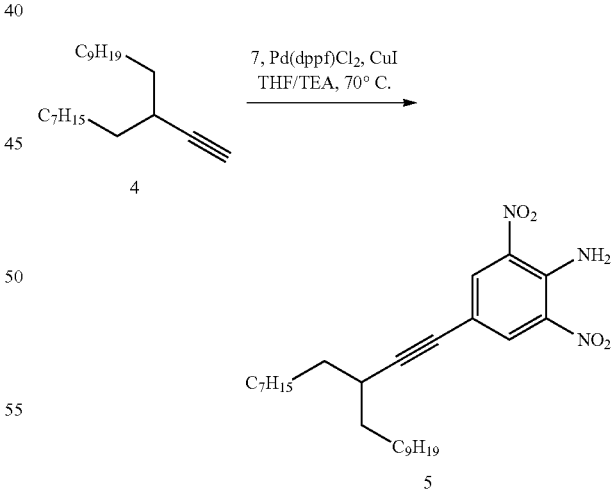

To anhydrous THF (10.0 mL) and TEA (10.0 mL) was added compound 4 (7.4 g, 21.2 mmol, 1.2 equiv.), compound 7 (5.2 g, 16.7 mmol, 1.0 equiv.), Pd(dppf)Cl$_2$ (0.05 g, 0.08 mmol, 0.02 equiv.), CuI (0.02 g, 0.1 mmol, 0.04 equiv.). The mixture was degassed under vacuum and purged with N$_2$ three times. The reaction was stirred at 70° C. for 8.0 hours. The mixture was cooled down and EA (10 mL) was added to dilute. The solid was filtered off and the filtrate was concentrated, then separated with a column to afford compound 5 7.5 g (84%) as a yellow solid. $^1$H NMR (300 MHz, CDCl$_3$) δ 7.99 (s, 2H), 2.45 (m, 1H), 1.26-1.55 (m, 40H), 0.87 (t, 6H).

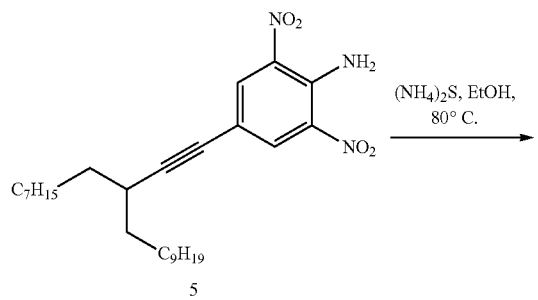

5

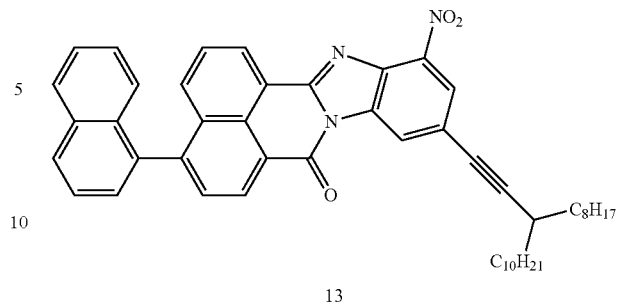

13

To a 25 mL flask was added compound 8 (5.1 g, 10.2 mmol, 2.2 equiv.), 3,4-perylene anhydride (4.6 mmol, 1 equiv.) and imidazole (21 g, 324.5 mmol, 70 equiv.). The mixture was degassed under vacuum and purged with N$_2$ three times. The reaction was stirred at 130° C. for 3 hours and 180° C. for 12 more hours. The dark purple mixture was cooled down. The solid was washed with water (3×60 mL) and EtOH (3×60 mL), and vacuum dried to give 13.

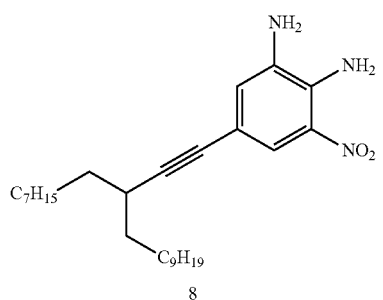

8

To EtOH (20.0 mL) was added compound 5 (7.5 g, 14.1 mmol, 1.0 equiv.) and ammonium sulfide (8.6 g 20% water solution, 28.2 mmol, 2.0 equiv.). The mixture was stirred at 80° C. for 1 hour. 2.0 equivalents of ammonium sulfide were added again. The mixture was stirred at 80° C. for an additional 1 hour. The mixture was concentrated, diluted with EA, washed with water and brine. The organic phase was collected, concentrated and separated through a column to give product 8 6.1 g (87%) as a dark red solid. $^1$H NMR (300 MHz, CDCl$_3$) δ 7.81 (s, 1H), 6.94 (s, 1H), 2.45 (m, 1H), 1.26-1.46 (m, 40H), 0.87 (t, 6H).

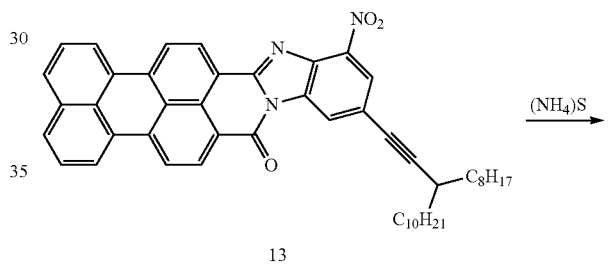

13

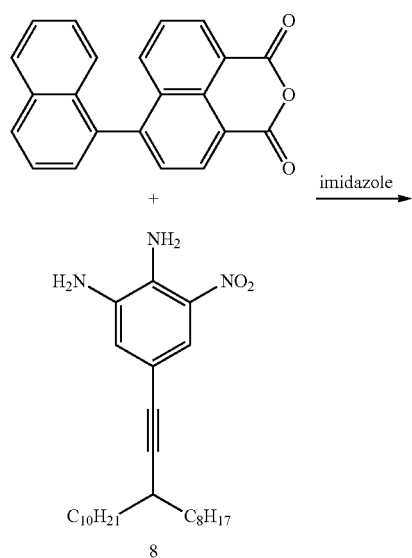

8

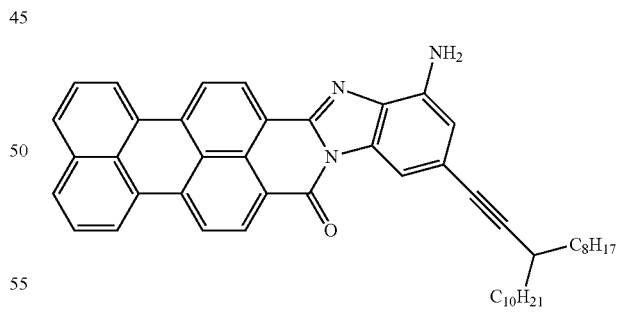

14

To EtOH (20.0 mL) was added compound 13 (14.1 mmol, 1.0 equiv.) and ammonium sulfide (28.2 mmol, 2.0 equiv.). The mixture was stirred at 80° C. for 1 hr. Refilled 2.0 equiv. ammonium sulfide. Stirring continued at 80° C. for 1 hr. The mixture was concentrated, diluted with EA, washed with water and brine, and dried to give 14.

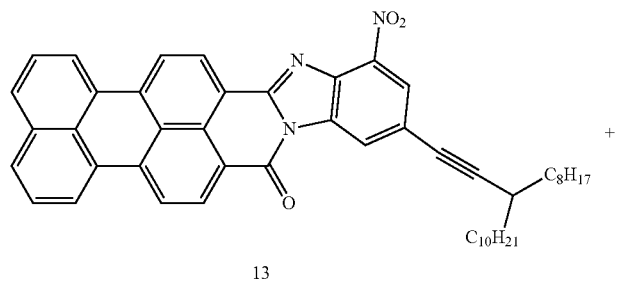

13

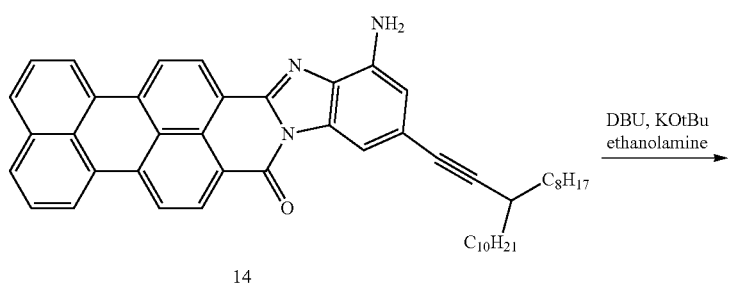

14

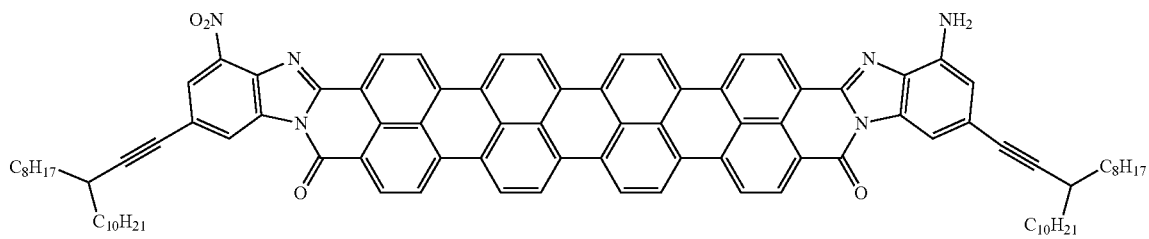

A mixture of 1.48 g (13 mmol) potassium tert-butoxide, 2.30 g (15.1 mmol) of diazabicyclo[5.4.0]undec-7-ene (DBU) 36.3 mmol) ethanolamine and 1.0 equiv. uiv. of 13 and 1.0 equiv. uiv. of 14 was heated to 140° C. for 11 h. Afterwards, the same amount of potassium tert-butylate, DBU and ethanolamine were added and the mixture was kept at 140° C. for 18 hours. The reaction mixture was cooled to room temperature, poured into 250 ml of 1M HCl filtered, washed until neutral pH and then dried to give the final product as a mixture of isomers.

Example 4

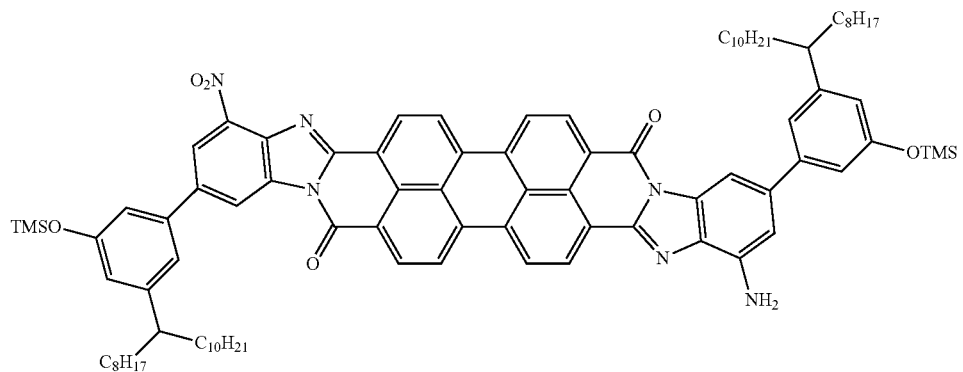

Procedure:

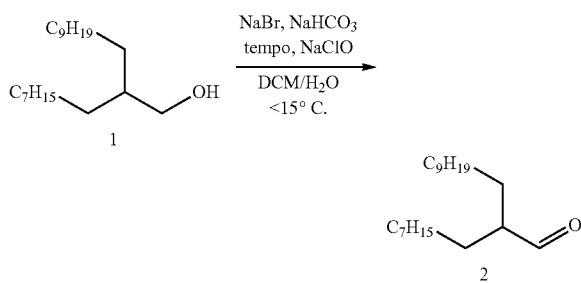

To H₂O (10.0 mL) was added NaHCO₃ (1.7 g, 20.2 mmol, 30 g/mol eq) and NaBr (280.0 mg, 2.7 mmol, 5 g/mol eq). The mixture was stirred to form a clear solution. Compound 1 (20 g, 56.4 mmol, 1 eq) in DCM (70 mL) and tempo (340.0 mg, 0.6 g/mol) were added to the clear solution. The two-phase mixture was cooled down to 10° C. The NaClO solution (70.5 mL, 0.8 N, 1 eq) was added dropwise with vigorously stirring. After addition, removed ice bath and kept stirring at room temperature for 30 min. The DCM phase was collected, extracted with DCM (25 mL×2), combined with organic phase, washed with water and brine, dried over MgSO₄, and was concentrated to give compound 2 18 g (90%) as a colorless oil. ¹H NMR (300 MHz, CDCl₃) not available.

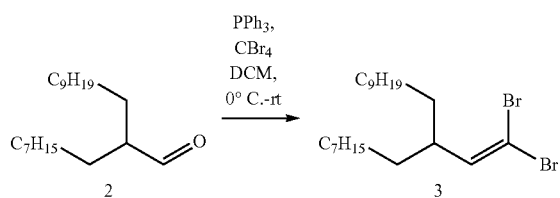

To DCM (500 mL) was added PPh₃ (154.0 g, 587 mmol, 4 eq) under N₂-atmosphere. To the suspension was added CBr₄ (97.3 g, 294 mmol, 2 eq) at 0° C. The mixture was stirred for 15 min at 0° C. and 20 min at room temperature. Freshly made compound 2 (51.4 g, 146 mmol, 1.0 eq) in DCM (150 mL) was added dropwise. The mixture was stirred at room temperature for 6 hours. Hexanes (1 L) was added. The solid was filtered off. The filtrate was concentrated. The residue was separated through a column to afford compound 3 57.0 g (79% in 2 steps) as colorless oil. ¹H NMR (300 MHz, CDCl₃) δ 0.88 (t, 6H), 1.26 (m, 28H), 2.35 (m, 1H), 6.10 (d, 1H).

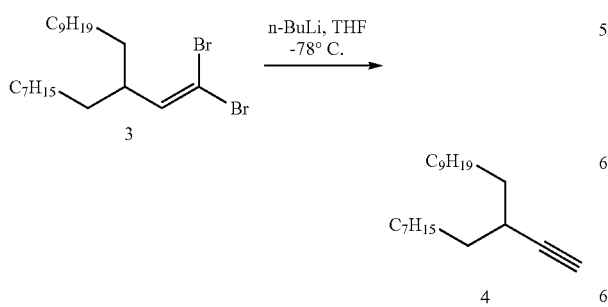

To anhydrous THF (250 mL) was added compound 3 (57.0 g, 115 mmol, 1 eq). The mixture was cooled down to −78° C. under N₂-atmosphere. n-BuLi (138 mL, 2.5 M, 3 eq) was added dropwise. The mixture was stirred for 2 hours, then was quenched with water (200 mL). The organic phase was collected. The water phase was extracted with EA (50 mL×2). The organic phases were combined, washed with water and brine, dried over MgSO₄ and concentrated to afford crude compound 4 37.1 g (100%) as colorless oil. ¹H NMR (300 MHz, CDCl₃) δ 0.88 (t, 6H), 1.26 (m, 28H), 2.30 (m, 1H), 2.03 (s, 1H).

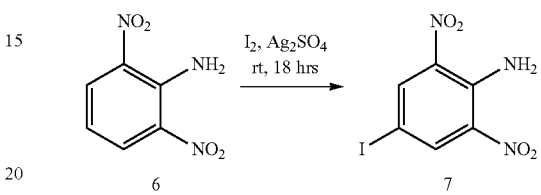

To EtOH (40.0 mL) was added compound 6 (4.2 g, 23.0 mmol, 1.0 eq), AgSO₄ (10.0 g, 32.1 mmol, 1.4 eq) and I₂ (8.2 g, 32.1 mmol, 1.4 eq). The mixture was stirred at room temperature for 18 hrs. Filtered off solid. Washed with EA. The filtrate was concentrated. The residue was separated through a column to afford compound 7 5.4 g (77%) as a dark yellow solid. ¹H NMR (300 MHz, CDCl₃) not available.

Scale up: To EtOH (1000.0 mL) was added compound 6 (100.0 g, 547.6 mmol, 1.0 eq), AgSO₄ (238.0 g, 764.3 mmol, 1.4 eq) and I₂ (195.2 g, 764.3 mmol, 1.4 eq). The mixture was stirred at room temperature for 18 hrs. Filtered off solid. Washed with EA (200 mL×2). The filtrate was concentrated till ⅓ volume. The solid was filtered and washed by cold EtOH (100 mL×2) to provide compound 7 43 g as dark yellow solid with less than 5% starting material 6 inside. The filtrate was concentrated and repeated the above procedure with 0.7 eq of AgSO₄ and I₂. The same working up process was applied to provided second batch of compound 7 30 g as dark yellow solid with less than 5% starting material 6 inside. Combined solids to afford compound 7 73 g (43.4%). ¹H NMR (300 MHz, CDCl₃) not available. Reaction was tracked by TLC.

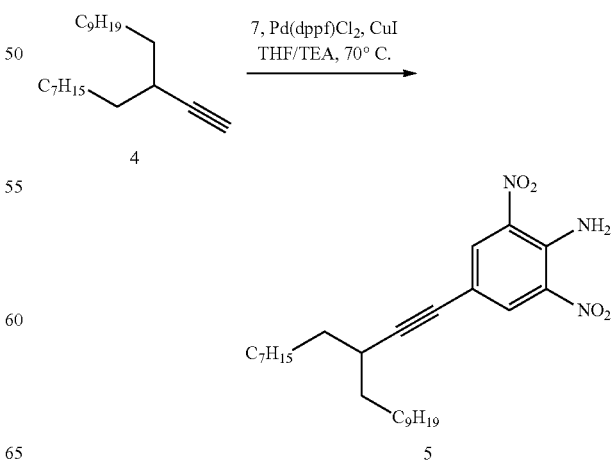

To anhydrous THF (10.0 mL) and TEA (10.0 mL) was added compound 4 (7.4 g, 21.2 mmol, 1.2 eq), compound 7 (5.2 g, 16.7 mmol, 1.0 eq), Pd(dppf)Cl₂ (0.05 g, 0.08 mmol, 0.02 eq), CuI (0.02 g, 0.1 mmol, 0.04 eq). The mixture was degassed under vacuum and purged with N₂ three times. The reaction was stirred at 70° C. for 8.0 hrs. The mixture was cooled down and EA (10 mL) was added to dilute. Filtered off the solid and concentrated the filtrate, separated with a column to afford compound 5 7.5 g (84%) as a yellow solid. ¹H NMR (300 MHz, CDCl₃) δ 7.99 (s, 2H), 2.45 (m, 1H), 1.26-1.55 (m, 40H), 0.87 (t, 6H).

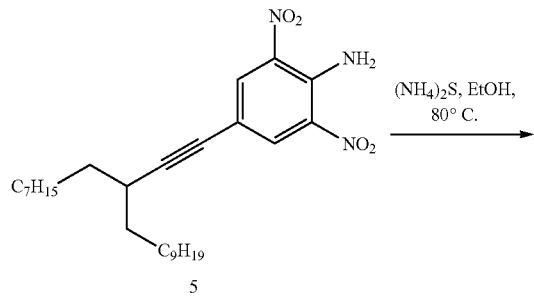

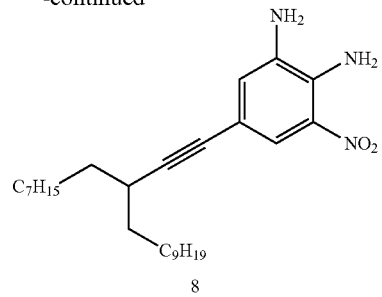

To EtOH (20.0 mL) was added compound 5 (7.5 g, 14.1 mmol, 1.0 eq) and ammonium sulfide (8.6 g 20% water solution, 28.2 mmol, 2.0 eq). The mixture was stirred at 80° C. for 1 hr. Refilled 2.0 eq ammonium sulfide. Kept stirring at 80° C. for 1 hr. The mixture was concentrated, diluted with EA, washed with water and brine. The organic phase was collected, concentrated and separated through a column to give product 8 6.1 g (87%) as a dark red solid. ¹H NMR (300 MHz, CDCl₃) δ 7.81 (s, 1H), 6.94 (s, 1H), 2.45 (m, 1H), 1.26-1.46 (m, 40H), 0.87 (t, 6H).

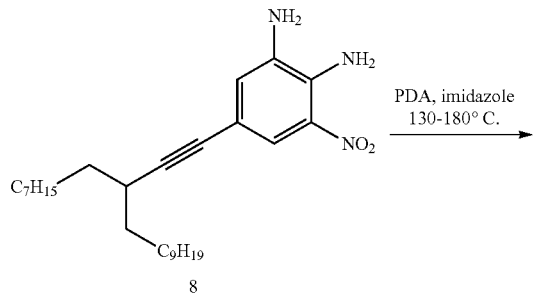

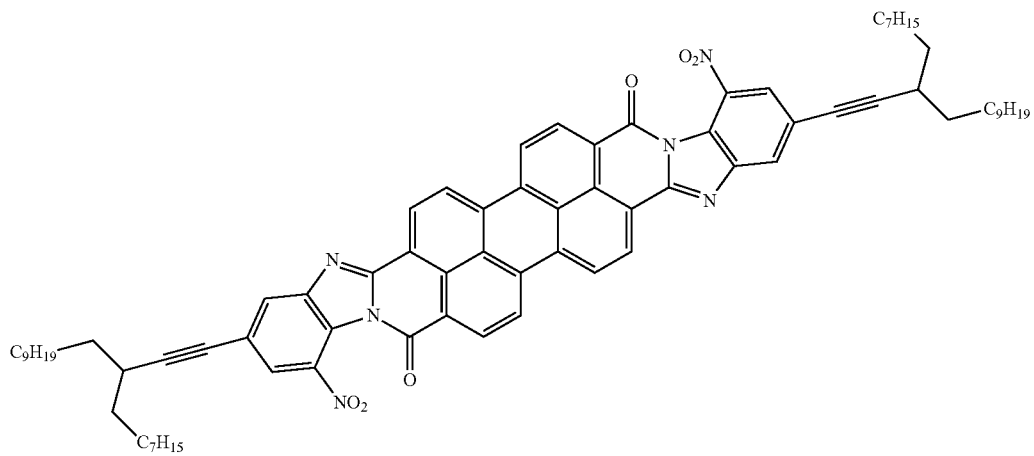

To a 25 mL flask was added compound 8 (5.1 g, 10.2 mmol, 2.2 eq), PDA (1.7 g, 4.6 mmol, 1 eq) and imidazole (21 g, 324.5 mmol, 70 eq). The mixture was degassed under vacuum and purged with $N_2$ three times. The reaction was stirred at 130° C. for 3 hours and 180° C. for 12 more hrs. The dark purple mixture was cooled down. The solid was washed with water (3×60 mL) and EtOH (3×60 mL), vacuum dried to give product 9 6.2 g (100%) as a dark purple solid. $^1$H NMR (300 MHz, $CDCl_3$) not available.

8.0 g of 9 and 16 mL of (cyclohexa-1,5-dien-1-yloxy)trimethylsilane were added to a two-neck round bottom flask under nitrogen. The resultant mixture was heated to 120 C in the sealed flask for 20 hrs. The reaction mixture was cooled to room temperature, dissolved in 100 mL DCM, and added to MeOH (500 mL). The precipitated solid material was filtered and washed with MeOH for 2 times to yield 6.5 g product (9 derivative).

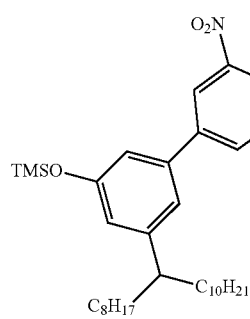
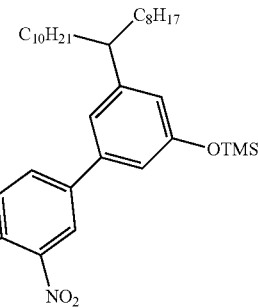

To the solution of 9 intermediate (1.5 g) in THF (100 mL), were added 20 mL isopropanol and 0.7 mL (NH4)2S solution (20 wt % in water). The resulting mixture was sealed in the flask and heated to 70 C for 2 hrs. The reaction mixture was concentrated by evaporating the solvent and re-taken into dichloromethane; the solution was washed with water for 3 times. After the solvent evaporated, the crude product was purified by silica column chromatography to yield 1.2 g product.

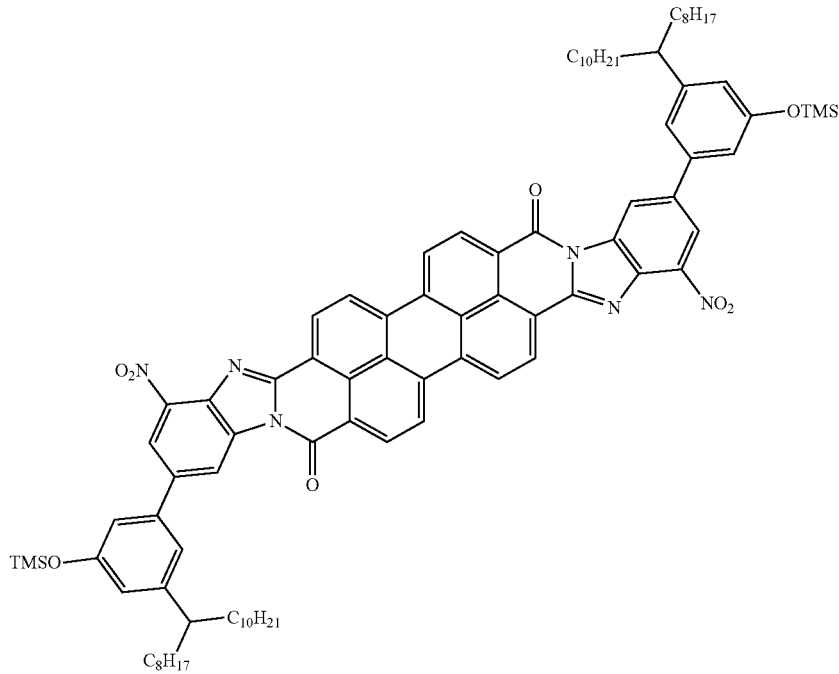

-continued

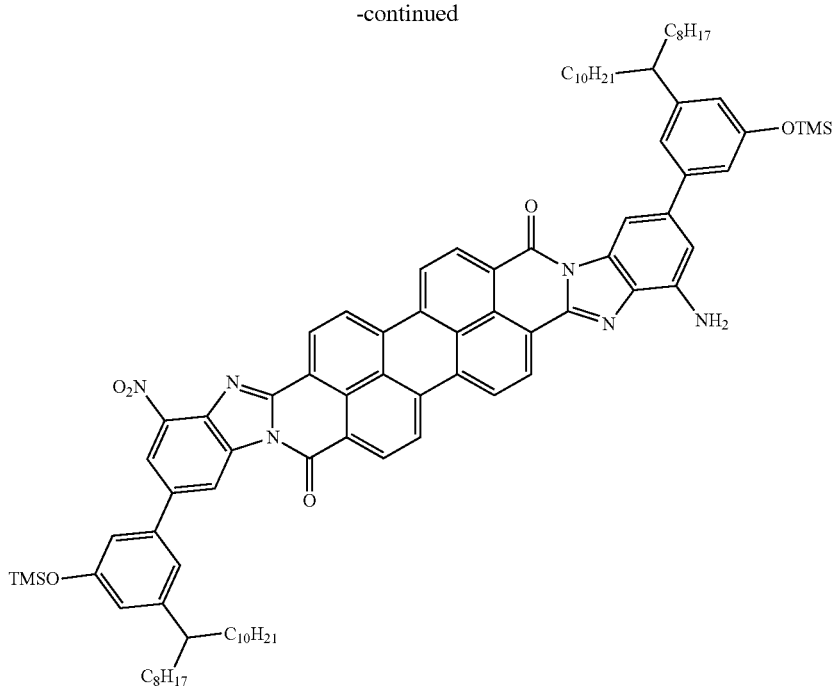

The final step in Example 4 partially reduces the intermediate such that the product has a desired nitra-amina-amidine combination. This diamina D-nitro has a favorable combination of donor and acceptor groups on a stackable rylene fragment to achieve hyper-polarizability.

Aspects of the present disclosure provide compounds characterized by highly nonlinear electric polarizabilitly. Such compounds are useful as high dielectric constant metadielectrics for meta-capacitors with extremely high capacitance and extremely high energy storage capacity.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the word "or" is used in the logical inclusive sense, e.g., "X or Y" covers X alone, Y alone, or both X and Y together, except where expressly stated otherwise. Two or more elements listed as alternatives may be combined together. The appended claims are not to be interpreted as including means-plus-function limitations, unless such a limitation is explicitly recited in a given claim using the phrase "means for."

What is claimed is:

1. An electro-polarizable compound having the following general formula (I):

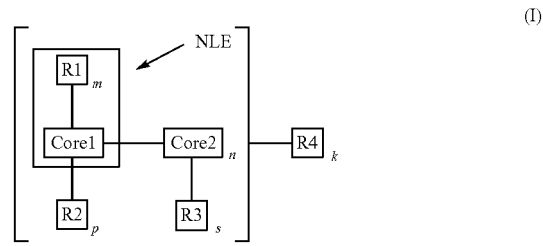

(I)

where Core1 is an aromatic polycyclic conjugated molecule having two-dimensional flat form and self-assembling by pi-pi stacking in a column-like supramolecule comprising one or more rylene fragments selected from structures 1 to 12:

1

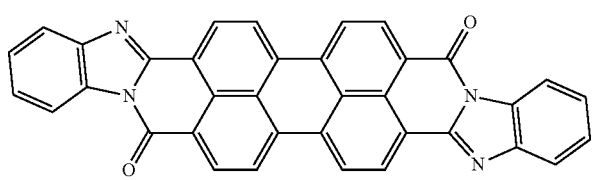

-continued
2
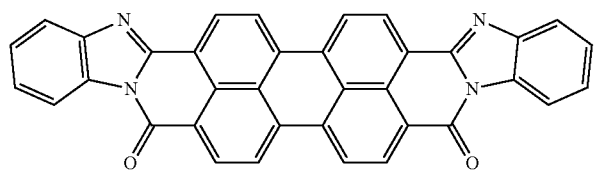
3
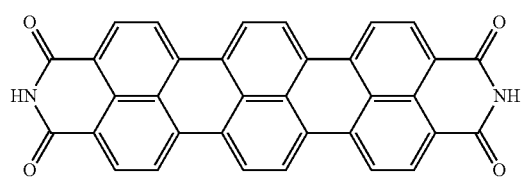
4
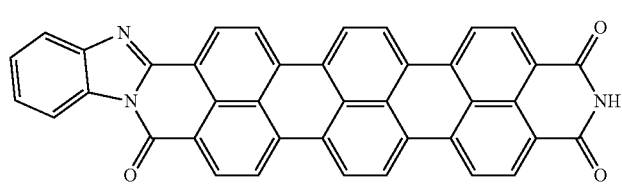
5
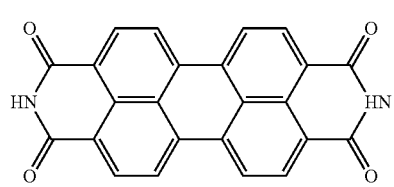
6
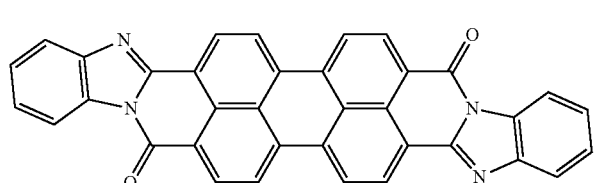
7
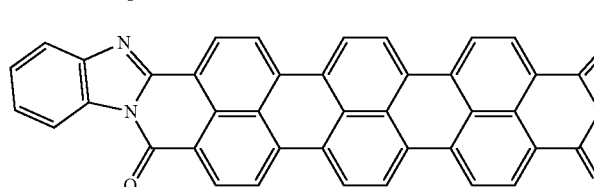
8
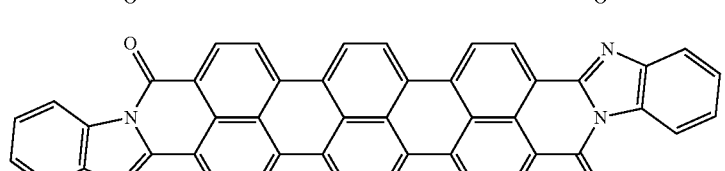
9
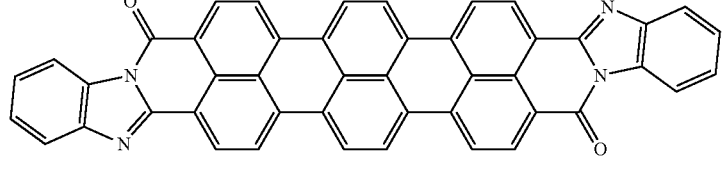
10
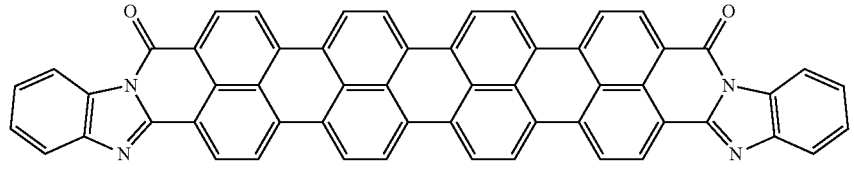

11
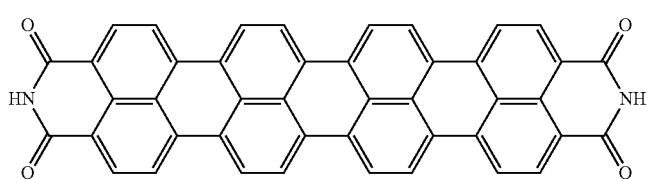
12
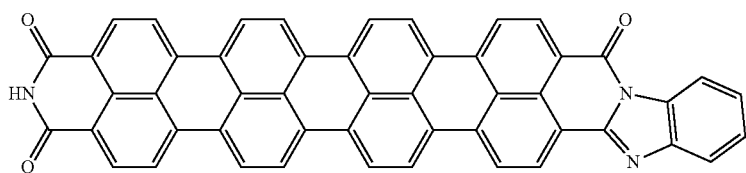
or a tetrapirolic macro-cyclic fragment that has a general structural formula form the group comprising structures 13 to 19, where M denotes an atom of metal or two protons (2H):
13
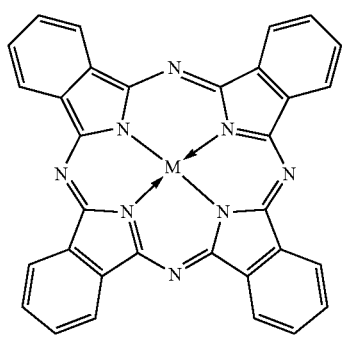
14
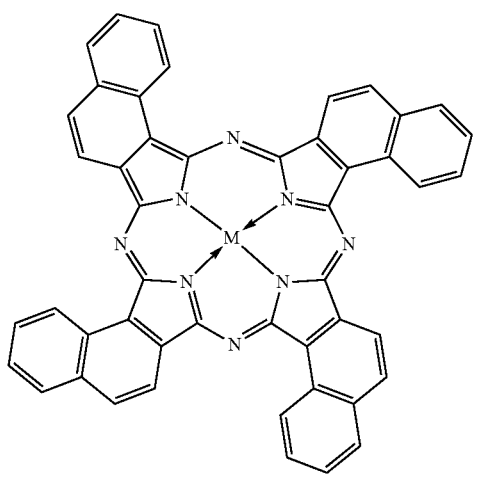
15
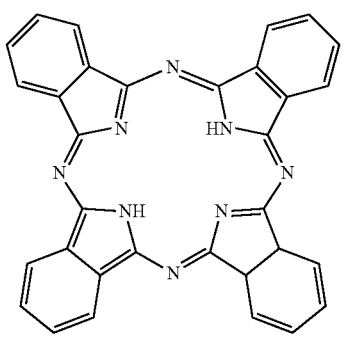
16
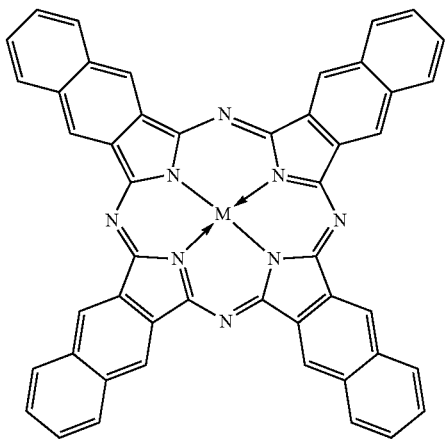

-continued

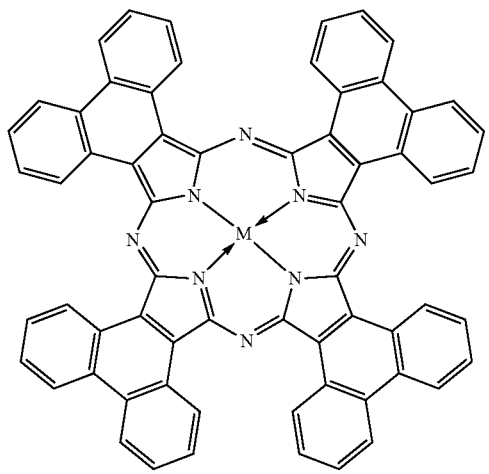
17

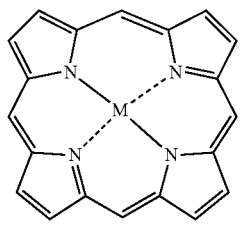
18

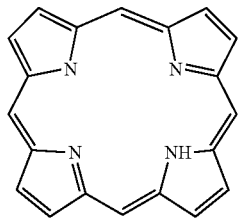
19

R1 is an dopant group connected to the aromatic polycyclic conjugated molecule (Core1) selected from nucleophilic groups (donors): —NO₂, —NH₃⁺ and —NR₃⁺, counterion Cl⁻ or Br⁻, —CHO, —CRO, —SO₃H, —SO₃R, SO₂NH₂, —COOH, —COOR, —COCl, —CONH₂, —CF₃, —CCl₃, —CN, wherein R is radical selected from the list consisting of alkyl, allyl, benzyl groups, phenyl, substituted phenyl and other aryl groups and electrophilic groups: —O⁻, —NH₂, —NHR, NR₂, —OH, OR, —NHCOR, —OCOR, alkyls, —C₆H₅, vinyls, wherein R is radical selected from the list consisting of alkyl, allyl, benzyl groups, phenyl, substituted phenyl and other aryl (aromatic) groups;

m is number of dopant groups R1 which is equal to 1, 2, 3 or 4,

R2 is a substituent comprising one or more ionic groups from a class of ionic compounds that are used in ionic liquids connected to the aromatic polycyclic conjugated molecule (Core1) directly or via a connecting group, p is number of ionic groups R2 which is equal to 0, 1, 2, 3 or 4;

wherein the fragment marked NLE containing the Core1 with at least one dopant group R1 has a nonlinear effect of polarization, wherein a fragment comprising the electro-conductive oligomer (Core2), resistive substituents providing solubility of the organic compound in a solvent and electrically insulating the column-like supramolecules from each other (R4) and/or the ionic groups R3 is selected from structures 98 to 107:

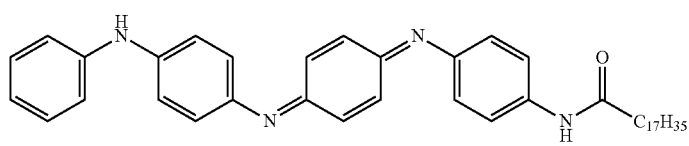
98

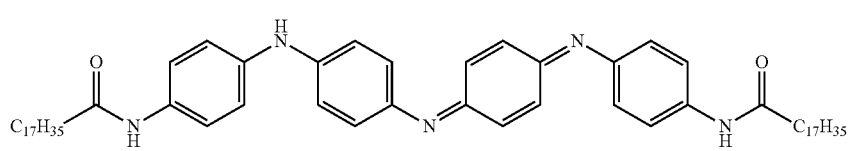
99

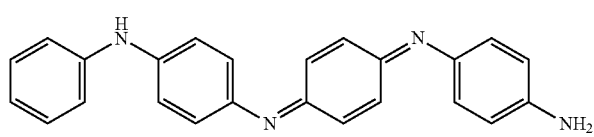 [SMILES: Nc1ccc(N=C2C=CC(=Nc3ccc(Nc4ccccc4)cc3)C=C2)cc1]
100

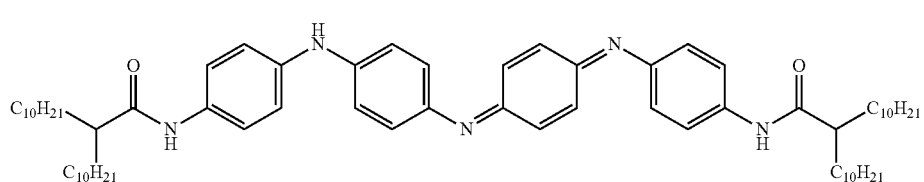
101

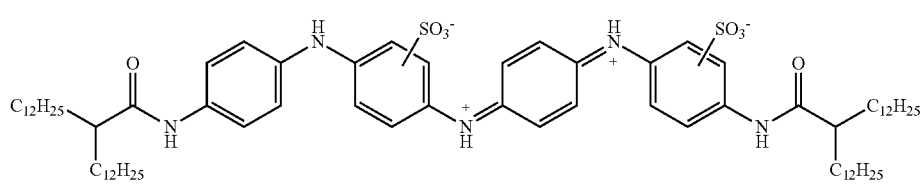

102

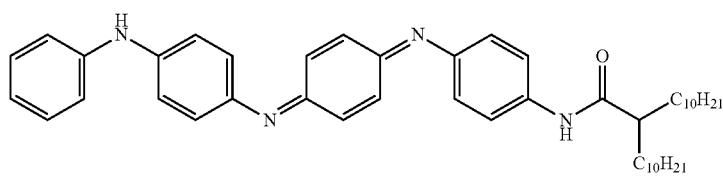

103

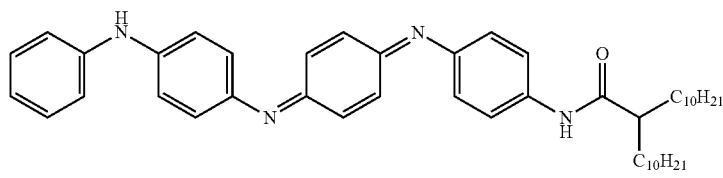

104

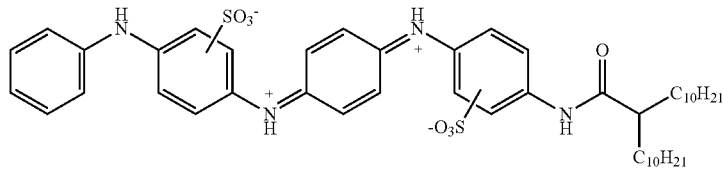

105

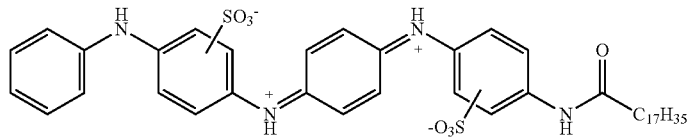

106

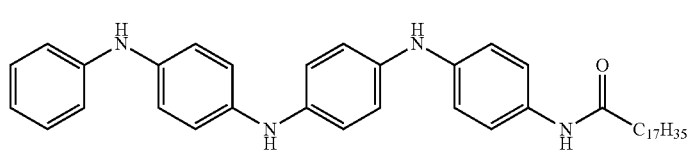

107

2. The electro-polarizable compound according to claim 1, wherein the dopant group (R1) is selected from nucleophilic groups (donors) and electrophilic groups (acceptors).

3. The electro-polarizable compound according to claim 2, wherein the electrophilic groups (acceptors) are selected from —$NO_2$, —$NH_3^+$ and —$NR_3^+$ (quaternary nitrogen salts), counterion $Cl^-$ or $Br^-$, —CHO (aldehyde), —CRO (keto group), —$SO_3H$ (sulfonic acids), —$SO_3R$ (sulfonates), $SO_2NH_2$ (sulfonamides), —COOH (carboxylic acid), —COOR (esters, from carboxylic acid side), —COCl (carboxylic acid chlorides), —$CONH_2$ (amides, from carboxylic acid side), —$CF_3$, —$CCl_3$, —CN, wherein R is radical selected from the list comprising alkyl (methyl, ethyl, isopropyl, tert-butyl, neopentyl, cyclohexyl etc.), allyl (—$CH_2$—CH=$CH_2$), benzyl (—$CH_2C_6H_5$) groups, phenyl (+substituted phenyl) and other aryl (aromatic) groups; and wherein the nucleophilic groups (donors) are selected from —$O^-$ (phenoxides, like —ONa or —OK), —$NH_2$, —NHR, $NR_2$, —OH, OR (ethers), —NHCOR (amides, from amine side), —OCOR (esters, from alcohol side), alkyls, —$C_6H_5$, vinyls, wherein R is radical selected from the list comprising alkyl (methyl, ethyl, isopropyl, tert-butyl, neopentyl, cyclohexyl etc.), allyl (—CH2-CH=CH2), benzyl (—CH2C6H5) groups, phenyl (+substituted phenyl) and other aryl (aromatic) groups.

4. The electro-polarizable compound according to claim 1, wherein at least one ionic group R2 or R3 is independently selected from the list comprising $[NR_4]^+$, $[PR_4]^+$ as cation and $[—CO_2O]^-$, $[—SO_3]^-$, $[—SR_5]^-$, $[—PO_3R]^-$, $[—PR_5]^-$ as anion, wherein R is selected from the list comprising H, alkyl, and fluorine.

5. The electro-polarizable compound according to claim 1, wherein the at least one connecting group is selected from the list comprising the following structures: 29-45, where W is hydrogen (H) or an alkyl group:

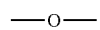

29

30

89
-continued

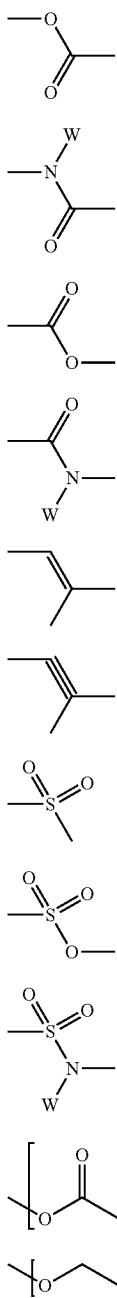

90
-continued

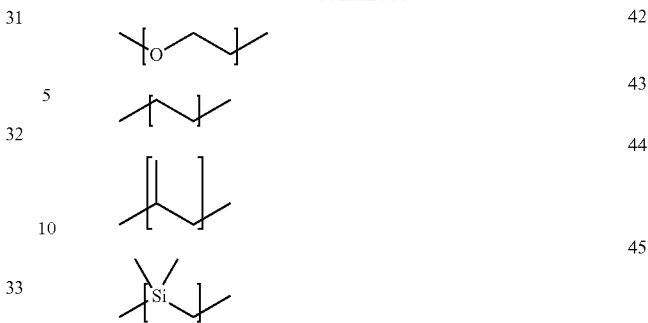

6. The electro-polarizable compound according to claim 1, wherein the at least one connecting group is selected from the group of $CH_2$, $CF_2$, $SiR_2O$, $CH_2CH_2O$, wherein R is selected from the list comprising H, alkyl, and fluorine.

7. The electro-polarizable compound according to claim 1, wherein the resistive substituent R4 is selected from the group of alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, n-butyl, iso-butyl and tert-butyl groups, and the aryl group is selected from phenyl, benzyl and naphthyl groups or siloxane, and/or polyethyleneglycol as linear or branched chains.

8. The electro-polarizable compound according to claim 1, wherein the resistive substituent R4 is $C_XQ_{2X+1}$, where $X \geq 1$ and Q is hydrogen (H), fluorine (F), or chlorine (Cl).

9. The electro-polarizable compound of claim 1, wherein the aromatic polycyclic conjugated molecule (Core1) and the dopant groups (R1) form a non-centrosymmetric molecular structure.

10. The electro-polarizable compound of claim 1, wherein the aromatic polycyclic conjugated molecule (Core1), the dopant groups (R1) and the resistive substituents (R4) form a non-centrosymmetric molecular structure.

11. An electro-polarizable compound of claim 1, wherein a fragment comprising the aromatic polycyclic conjugated molecule (Core1), dopant groups (R1) and resistive substituents providing solubility of the organic compound in a solvent and electrically insulating the column-like supramolecules from each other (R4) is selected from structures 46 to 97:

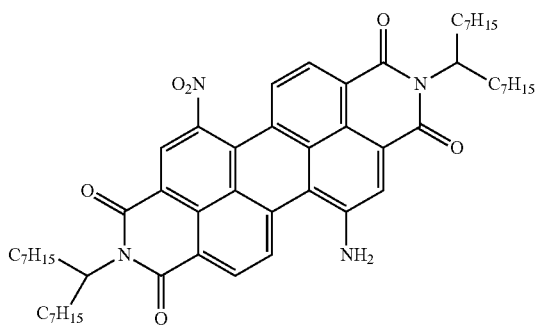

46

-continued
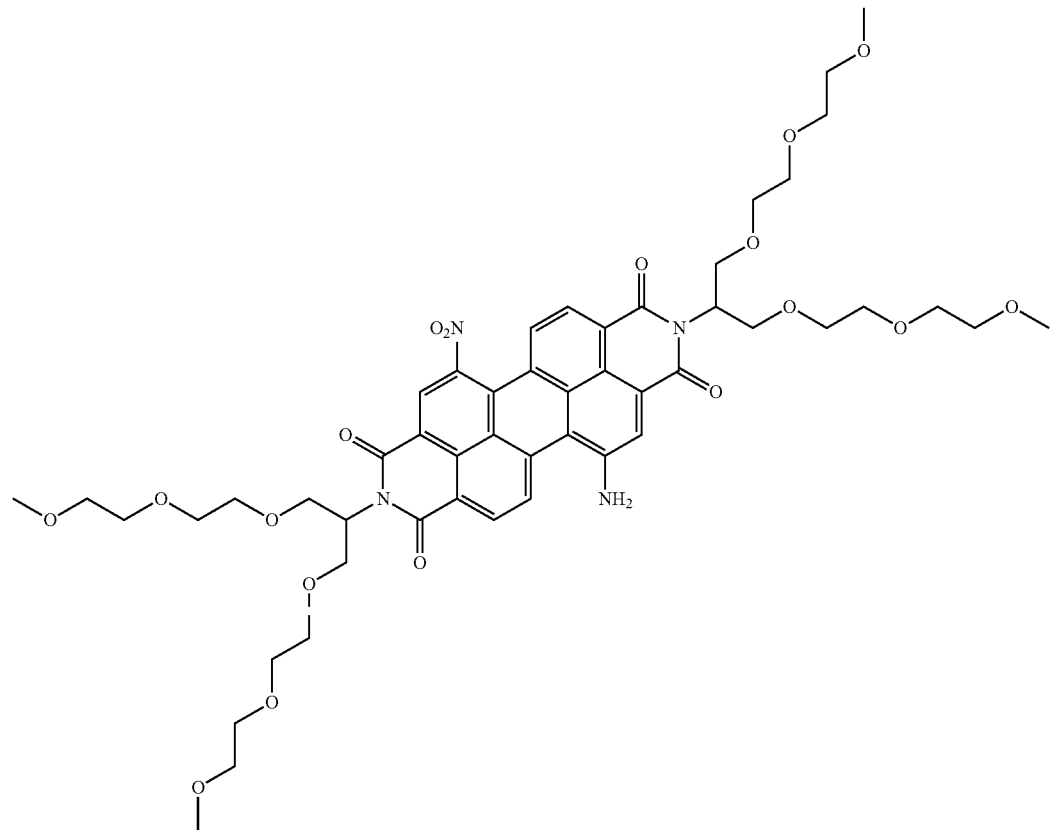
47
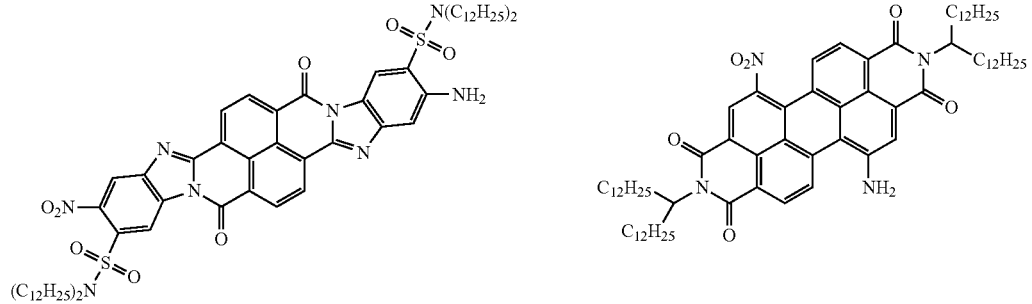
48 49
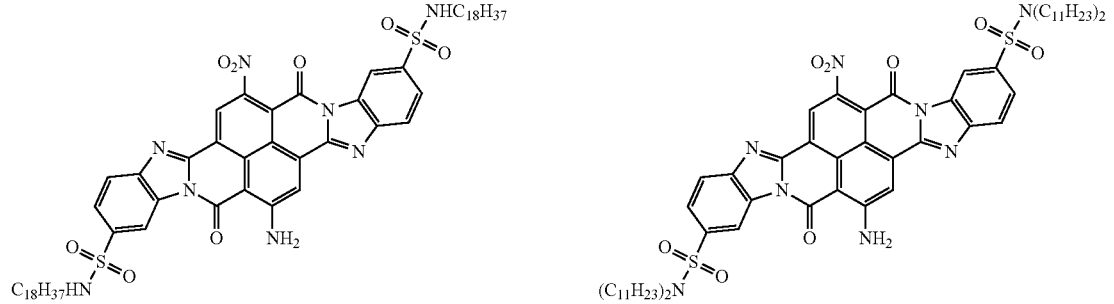
50 51

-continued
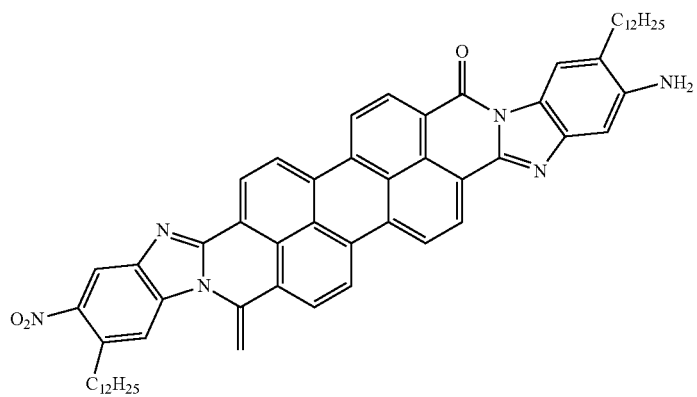
52
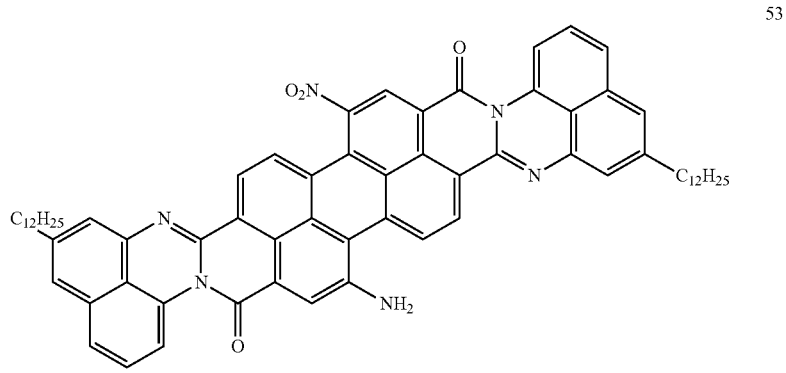
53
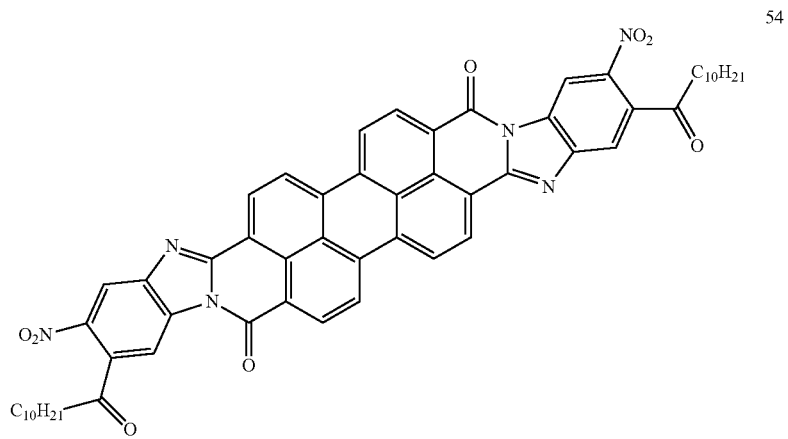
54

-continued
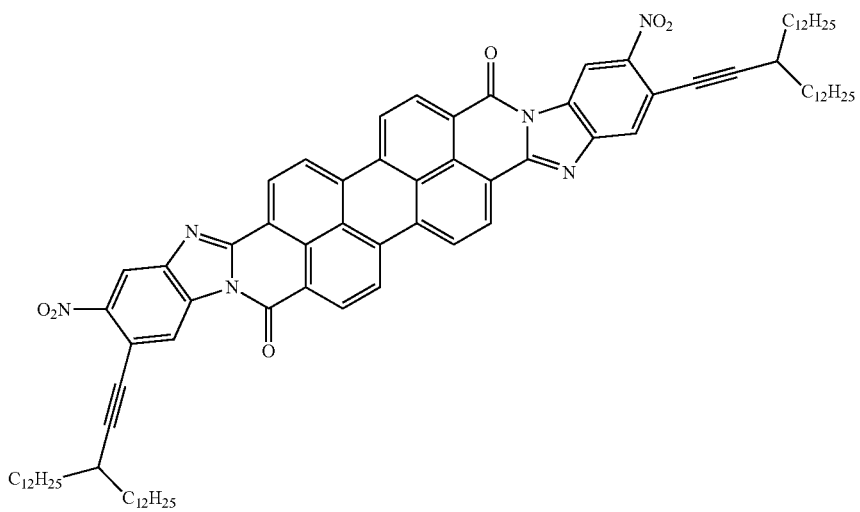
55
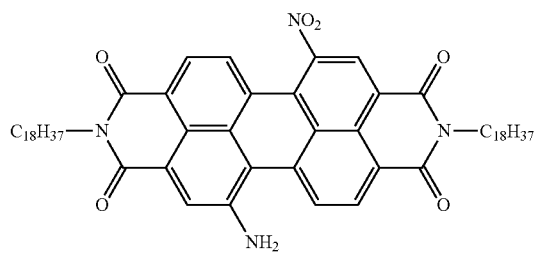
56
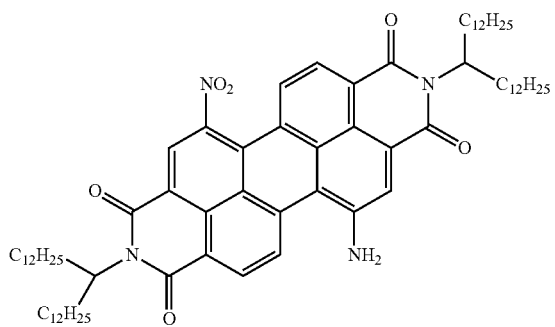
57
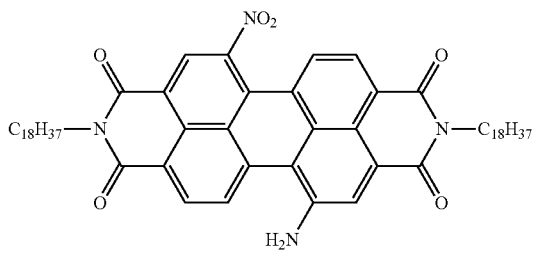
58
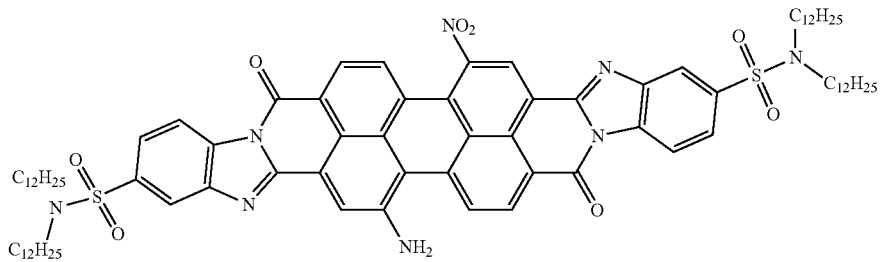
59
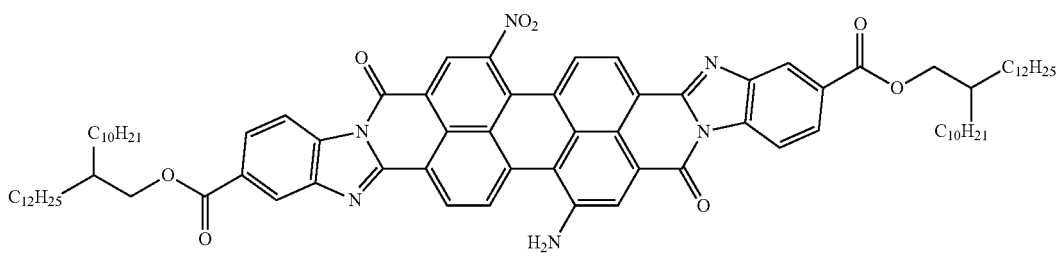
60

-continued
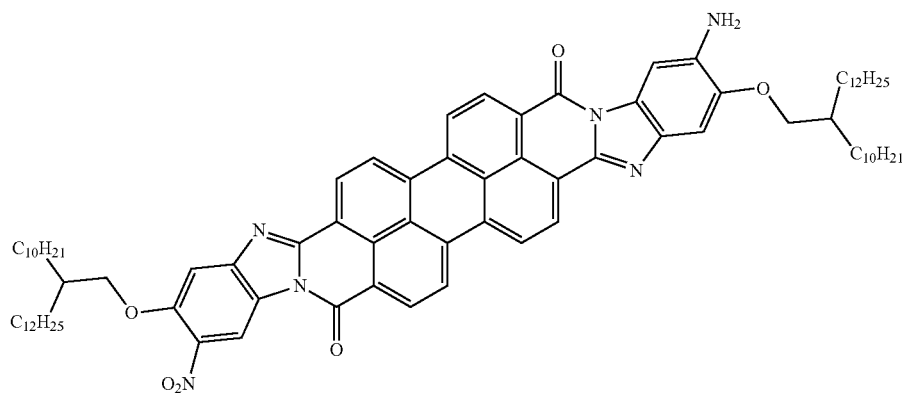
61
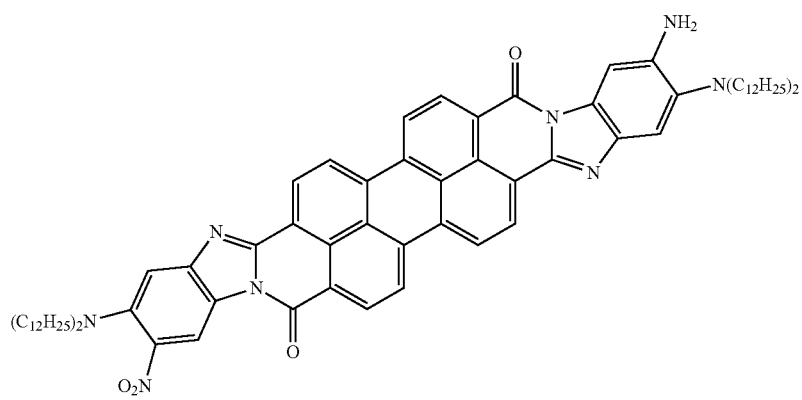
62
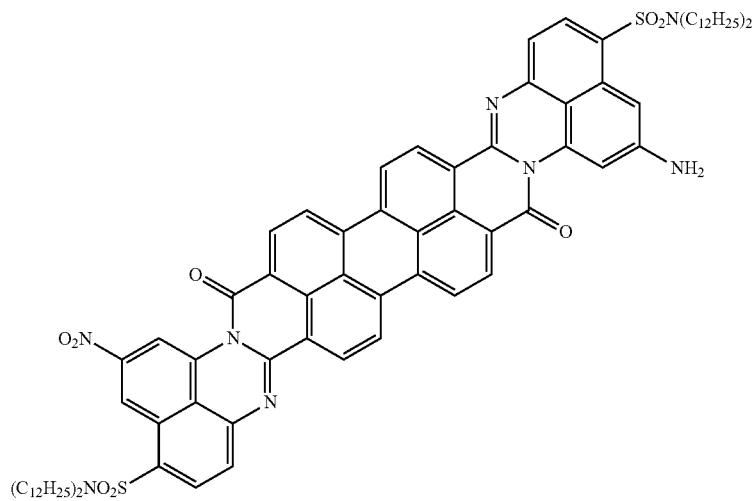
63
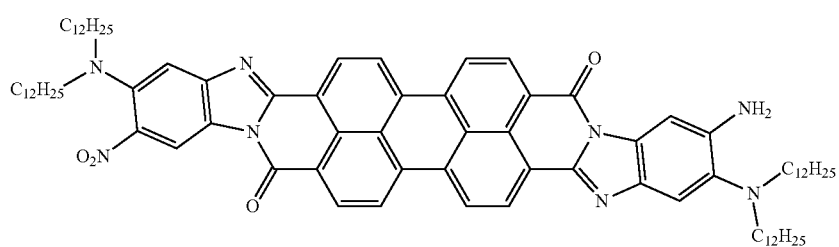
64

-continued
65
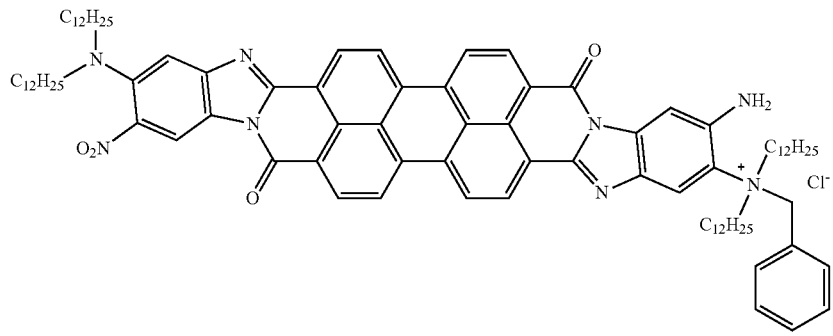
66
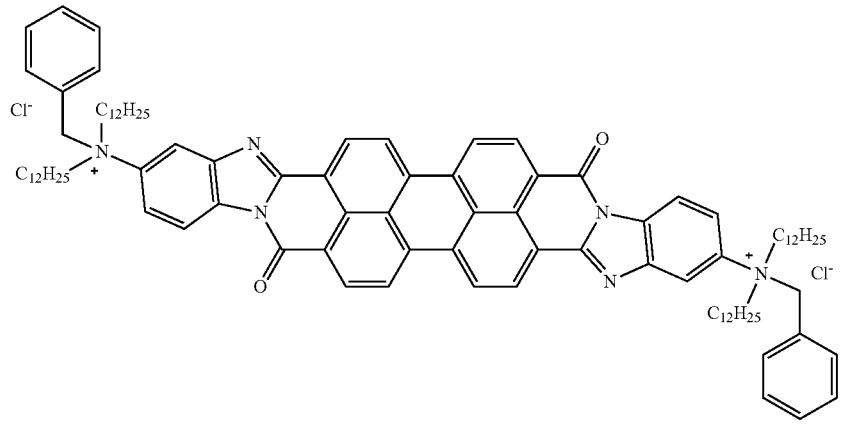
67
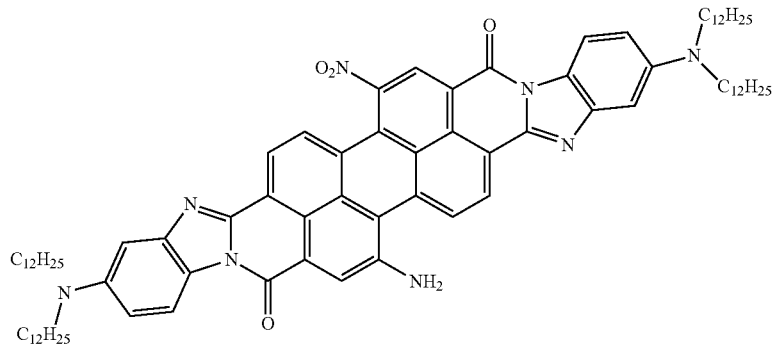
68
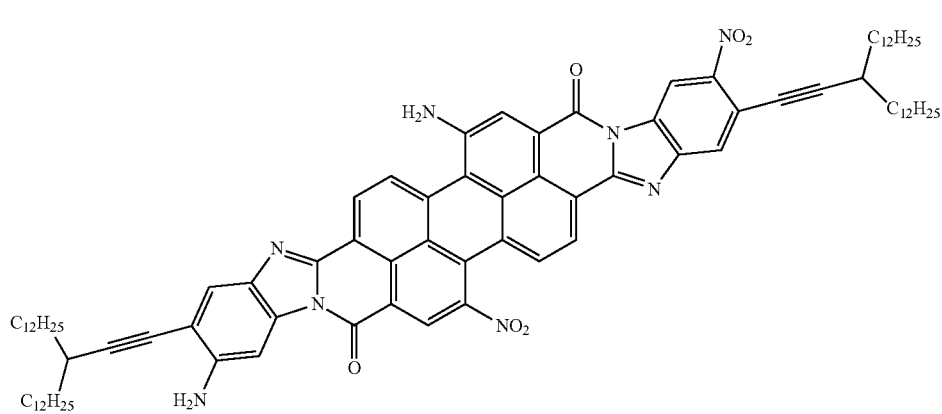

-continued
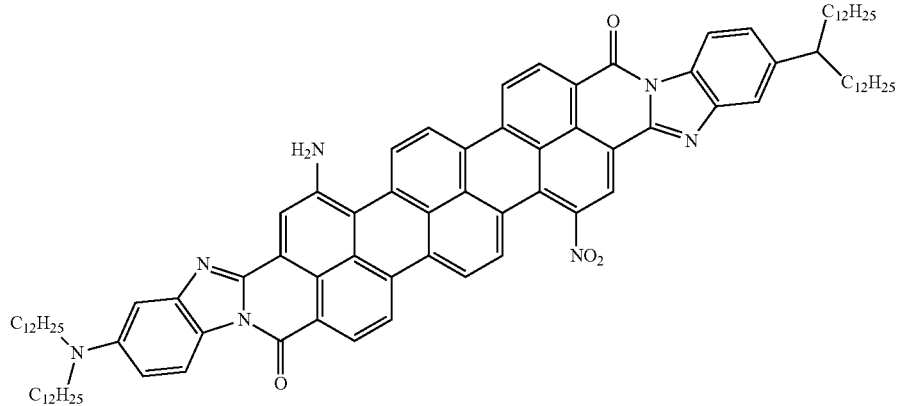
69
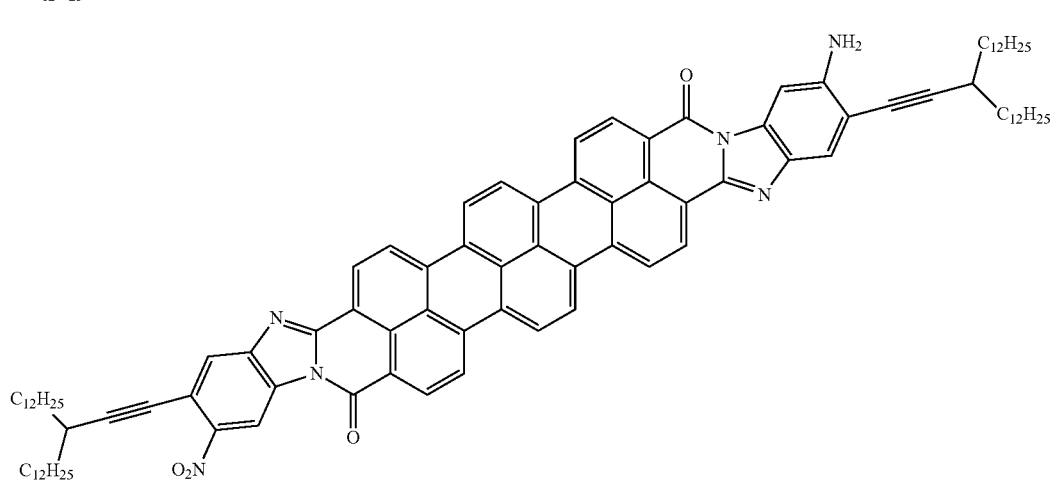
70
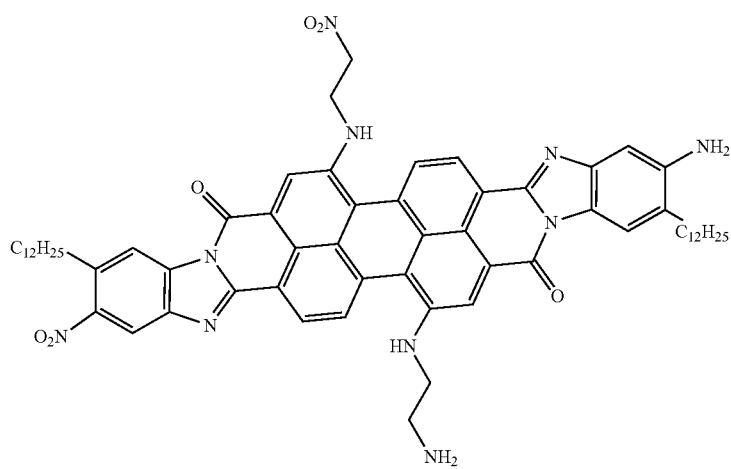
71
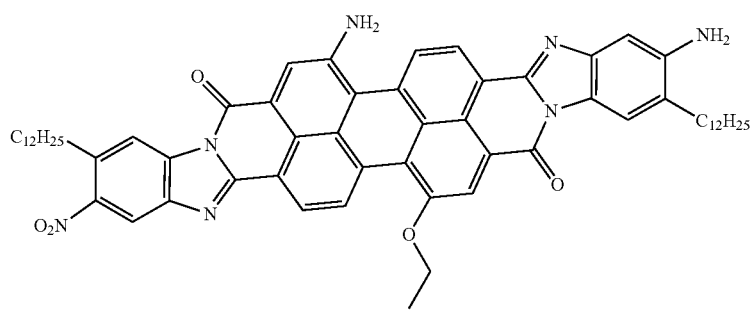
72

-continued
73
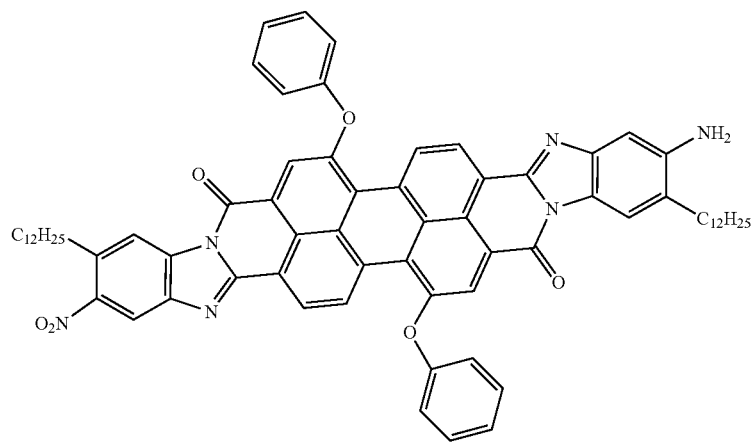
74
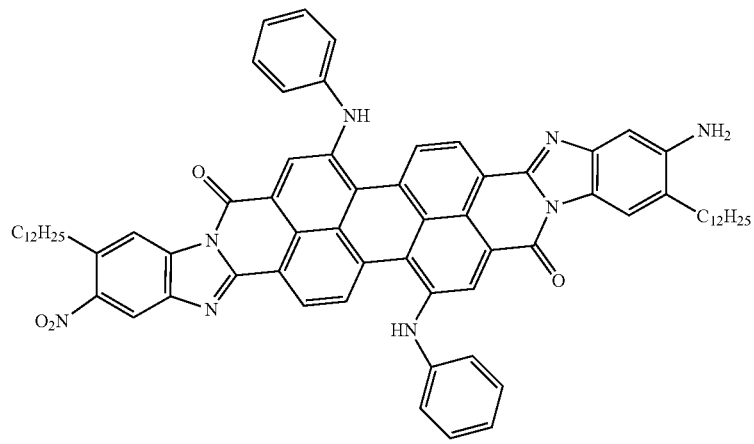
75
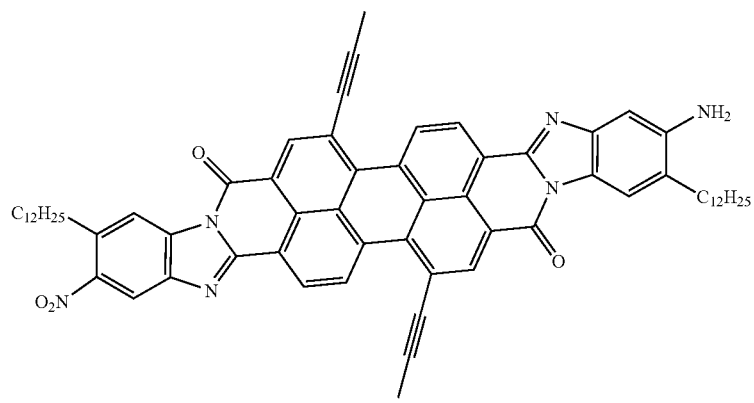
76
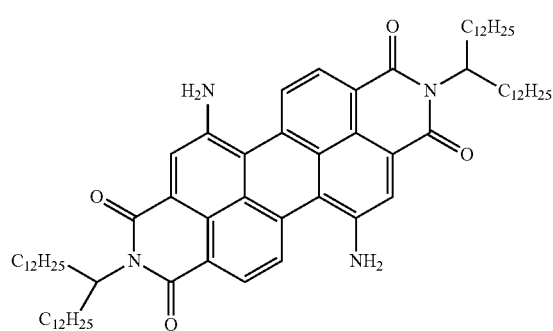

-continued
77
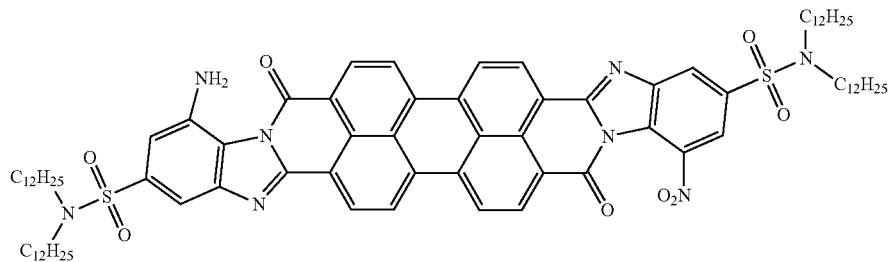
78
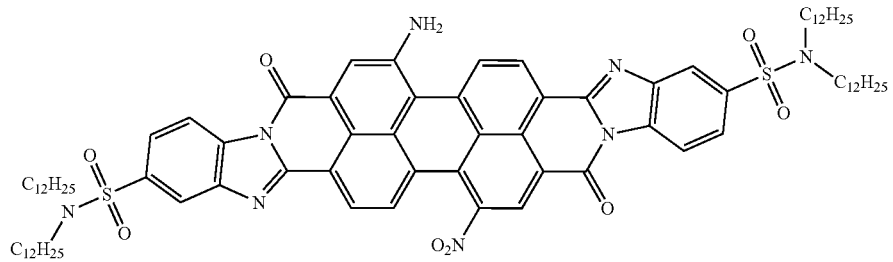
79
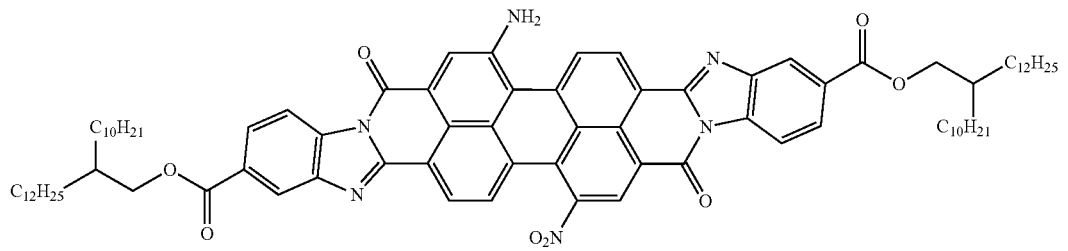
80
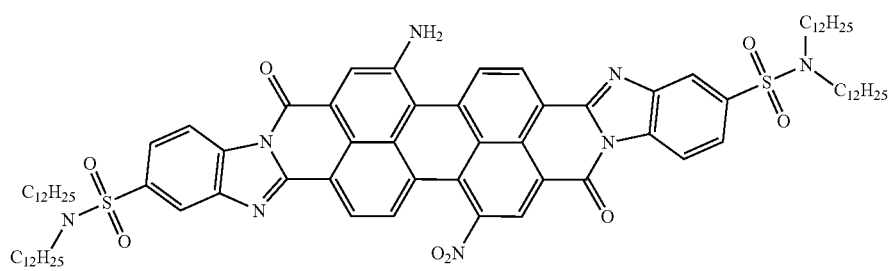
81
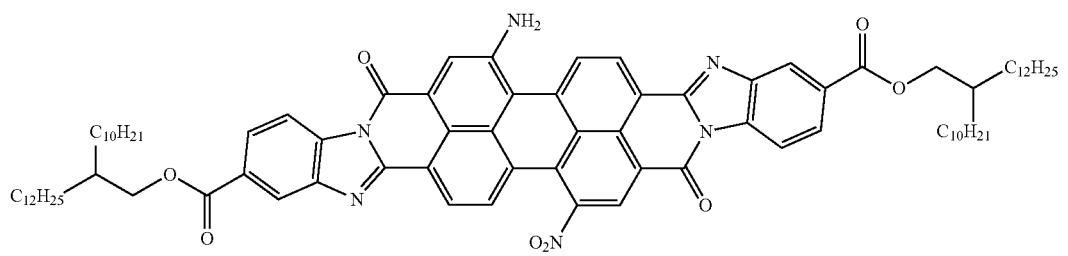
82
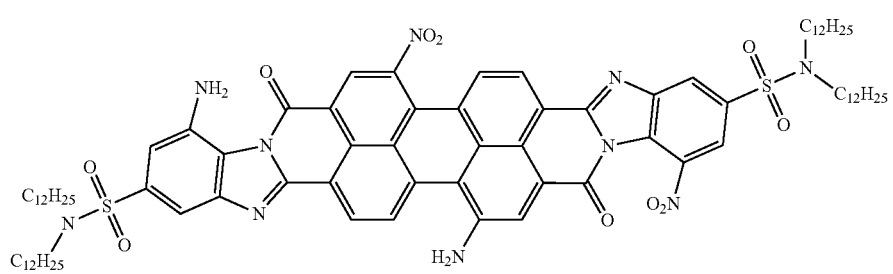

-continued
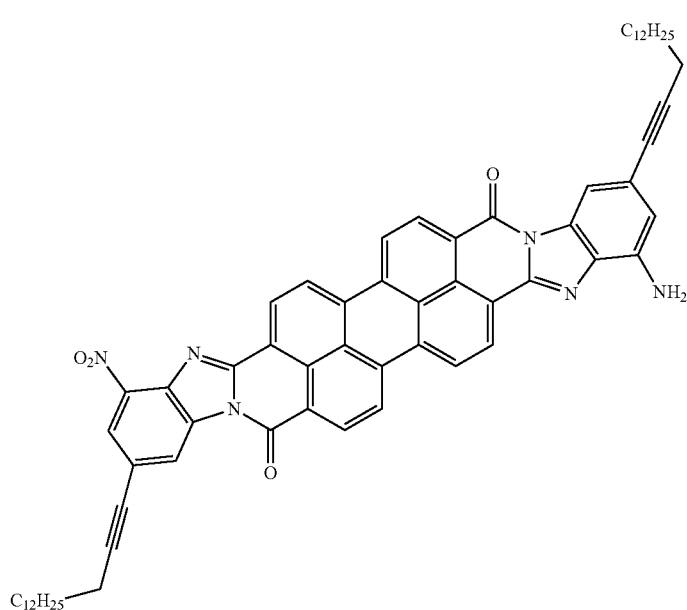
83
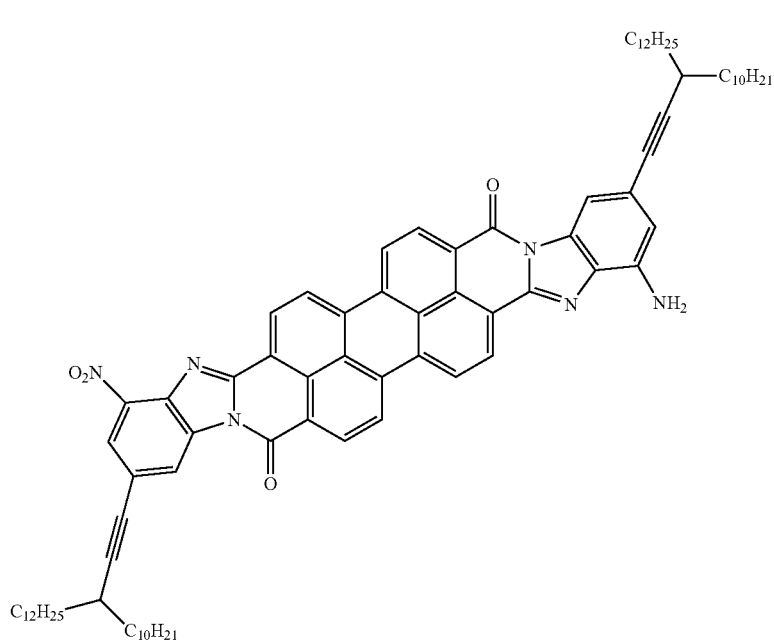
84
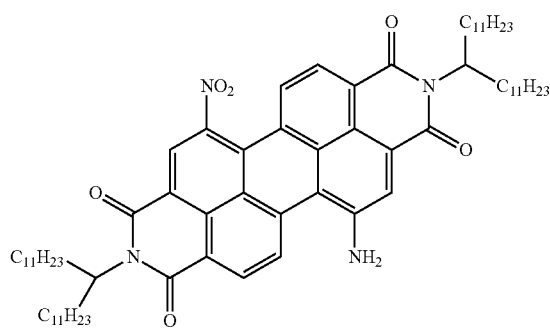
85
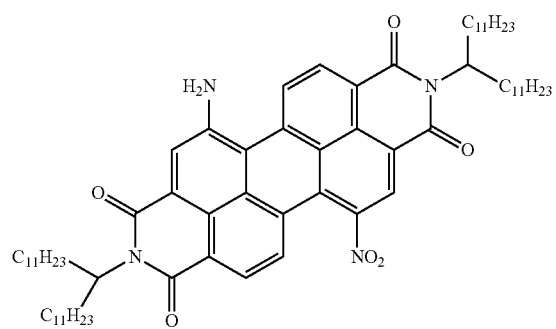
86

-continued
87
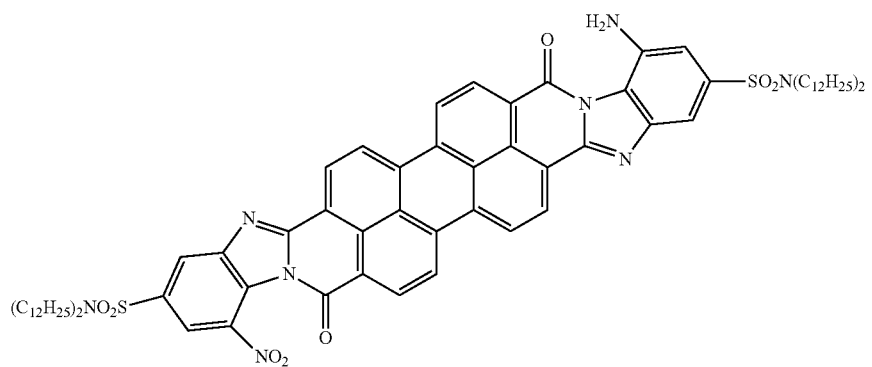
88
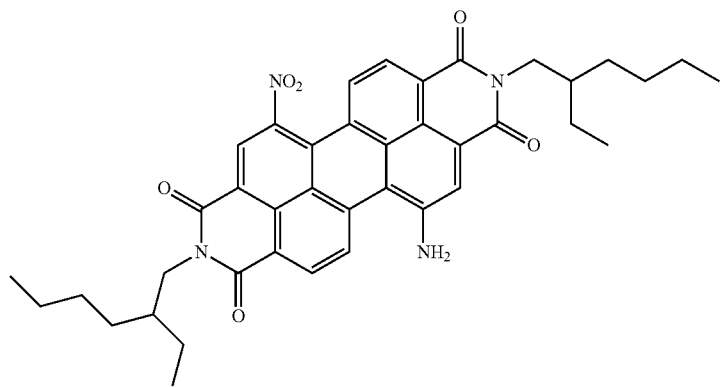
89
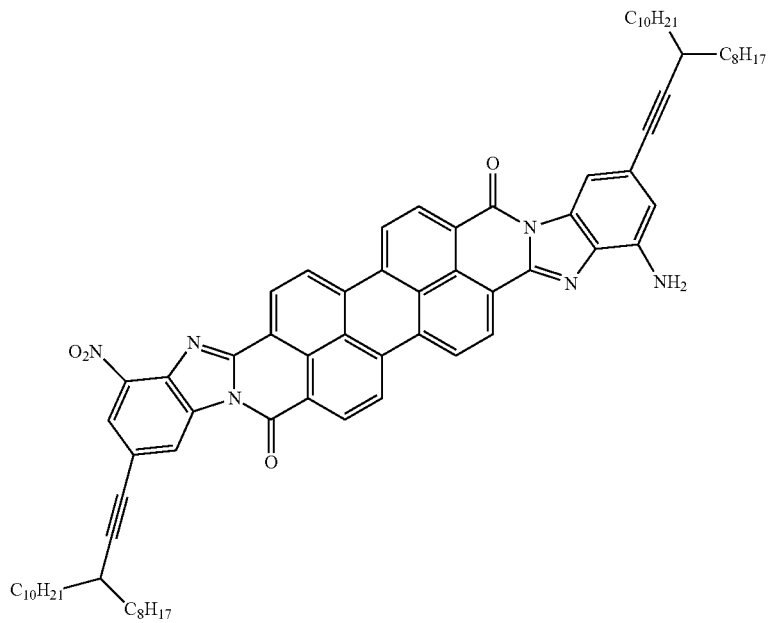

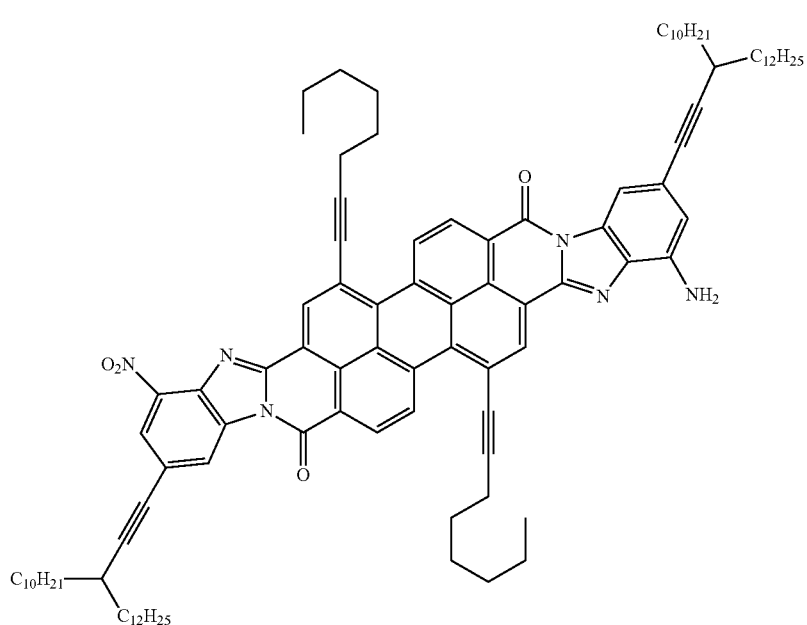
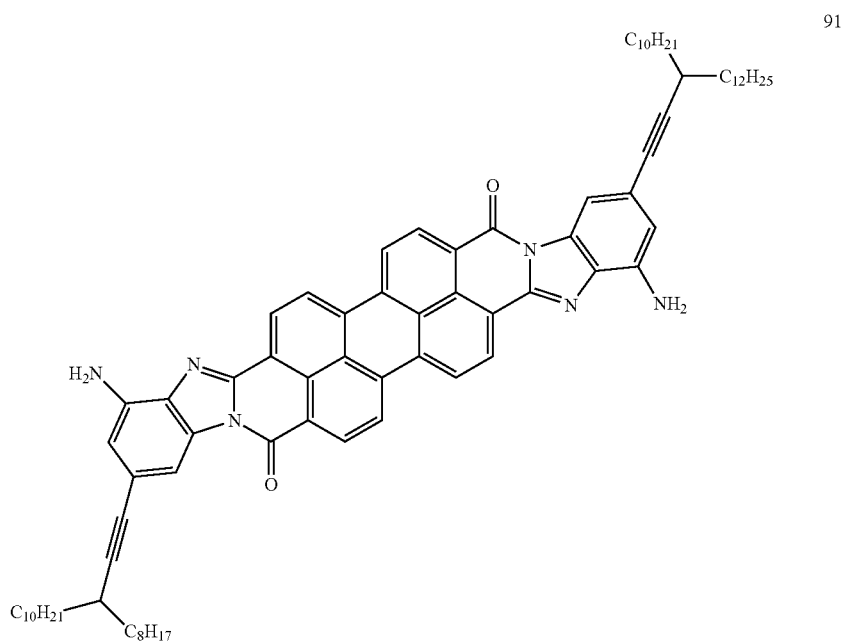

-continued
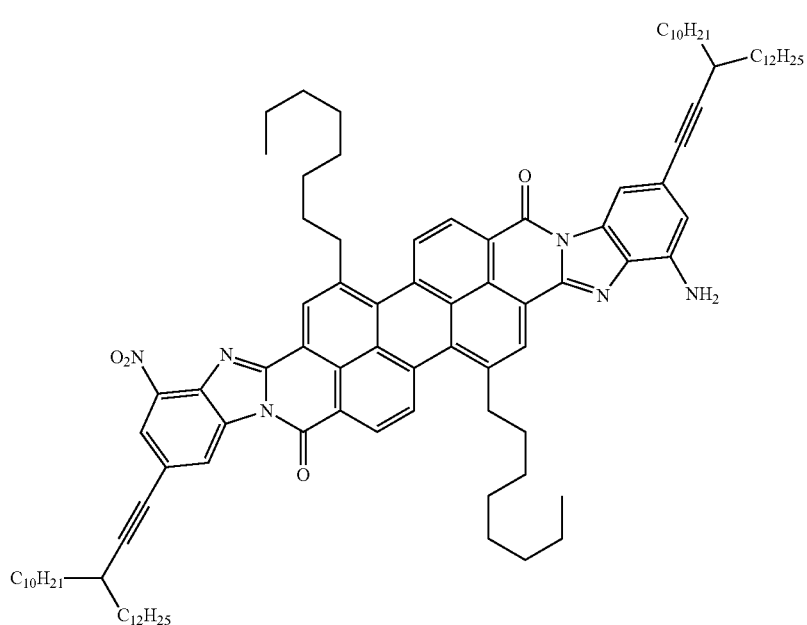
92
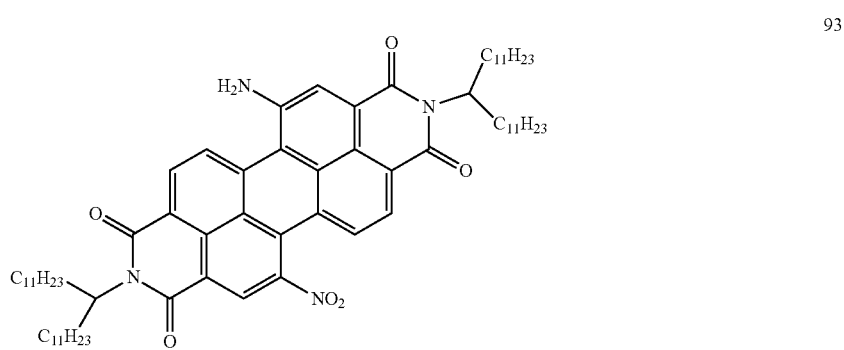
93
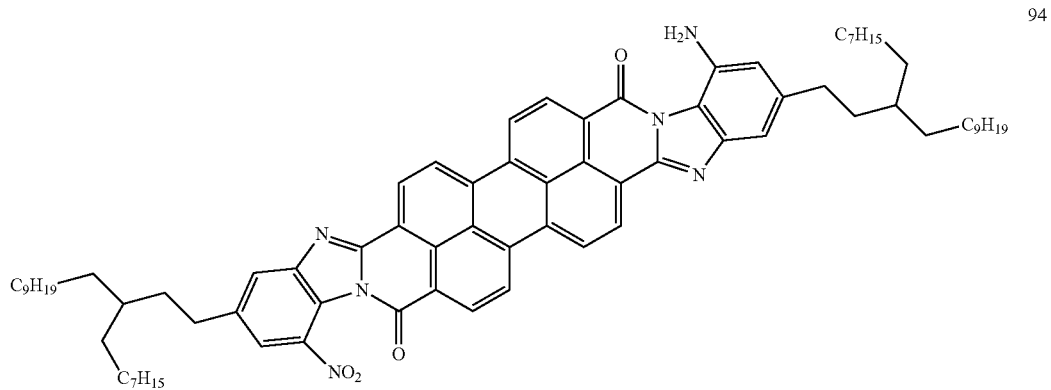
94

-continued
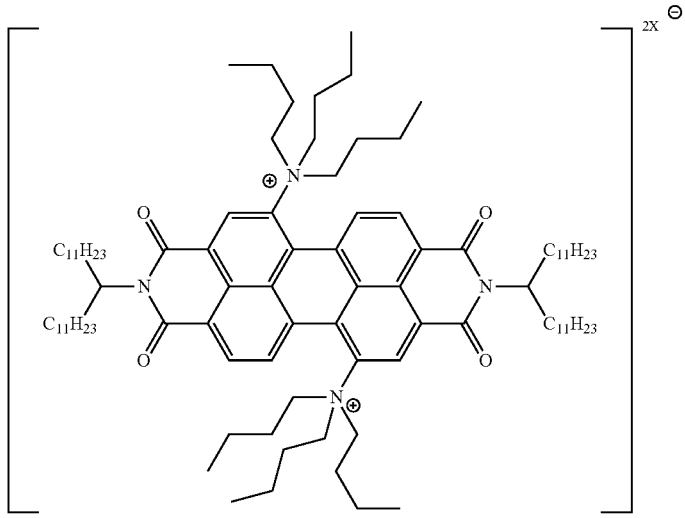
One ionic group should be anionic (SO3——, COOH, etc)
95
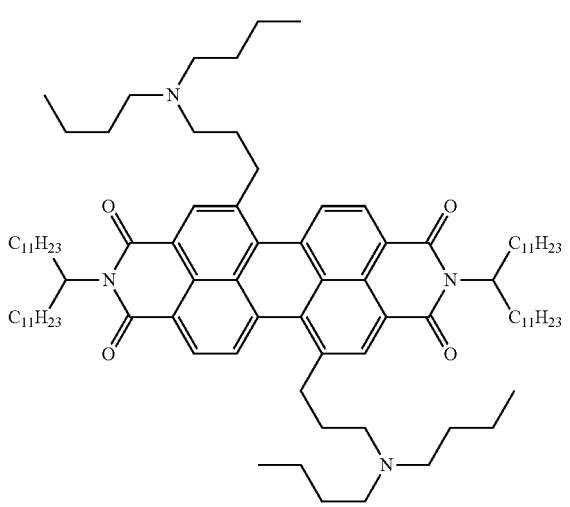
96
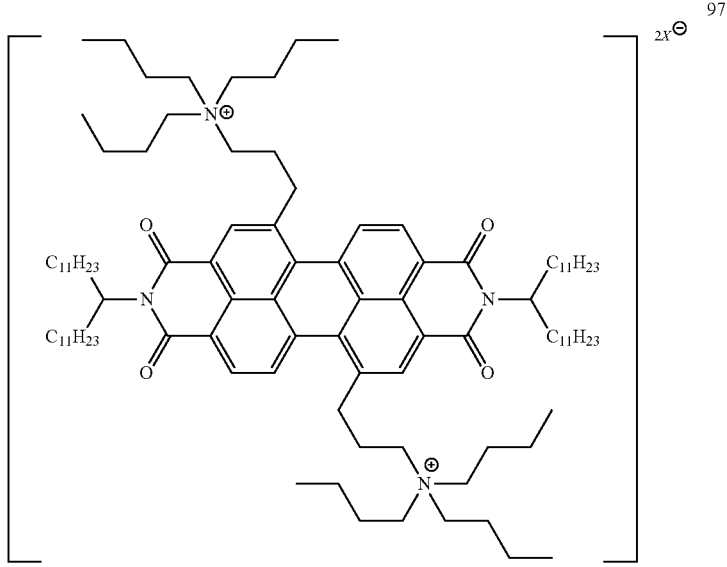
1 donor and acceptor group
97

12. A solution comprising an organic solvent and at least one type of electro-polarizable compound according to claim 1.

13. The solution according to claim 12, comprising a mixture of different electro-polarizable compounds.

14. The solution according to claim 12, wherein the organic solvent is selected from the list consisting of ketones, carboxylic acids, hydrocarbons, cyclic hydrocarbons, chlorohydrocarbons, alcohols, ethers, esters, acetone, xylene, toluene, ethanol, methylcyclohexane, ethyl acetate, diethyl ether, octane, chloroform, methylene chloride, dichloroethane, trichloroethene, tetrachloroethene, carbon tetrachloride, 1,4-dioxane, tetrahydrofuran, pyridine, triethylamine, nitromethane, acetonitrile, dimethylformamide, dimethyl sulfoxide, and any combination thereof.

15. The solution according claim 12, wherein the solution is a lyotropic liquid crystal solution.

16. A crystal metadielectric layer comprising a mixture of the electro-polarizable compounds according to claim 1, wherein the nonlinearly polarizable fragments comprising an aromatic polycyclic conjugated molecule with at least one dopant group, the electro-conductive oligomers and the ionic groups which have electronic and/or ionic type of polarizability are placed into the resistive dielectric envelope formed by resistive substituents providing solubility of the organic compound in a solvent and electrically insulating the column-like supramolecules from each other.

17. The crystal metadielectric layer according to claim 16, wherein the column-like supramolecules are formed by the electro-polarizable compounds comprising rylene fragments of different length.

18. The crystal metadielectric layer according to claim 16, wherein the layer's relative permittivity is greater than or equal to 1000 and the layer's resistivity is greater than or equal to $10^{13}$ ohm/cm.

19. A meta-capacitor comprising two metal electrodes positioned parallel to each other and which can be rolled or flat and planar and metadielectric layer between this electrodes, wherein the layer comprises the electro-polarizable compounds according to any claim 1, wherein the nonlinearly polarizable fragments comprising an aromatic polycyclic conjugated molecule with at least one dopant group, the electro-conductive oligomers and the ionic groups which have electronic and/or ionic type of polarizability are placed into the resistive dielectric envelope formed by resistive substituents providing solubility of the organic compound in a solvent and electrically insulating the column-like supramolecules from each other.

* * * * *